US012065668B2

(12) United States Patent
Joung et al.

(10) Patent No.: US 12,065,668 B2
(45) Date of Patent: *Aug. 20, 2024

(54) RNA-GUIDED TARGETING OF GENETIC AND EPIGENOMIC REGULATORY PROTEINS TO SPECIFIC GENOMIC LOCI

(71) Applicant: The General Hospital Corporation, Boston, MA (US)

(72) Inventors: J. Keith Joung, Winchester, MA (US); Morgan Maeder, Brookline, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/450,135

(22) Filed: Oct. 6, 2021

(65) Prior Publication Data

US 2022/0090145 A1 Mar. 24, 2022

Related U.S. Application Data

(60) Division of application No. 16/535,199, filed on Aug. 8, 2019, now Pat. No. 11,168,338, which is a continuation of application No. 14/775,869, filed as application No. PCT/US2014/027335 on Mar. 14, 2014, now Pat. No. 10,378,027.

(60) Provisional application No. 61/921,007, filed on Dec. 26, 2013, provisional application No. 61/838,178, filed on Jun. 21, 2013, provisional application No. 61/838,148, filed on Jun. 21, 2013, provisional application No. 61/799,647, filed on Mar. 15, 2013.

(51) Int. Cl.

| | |
|---|---|
| ***C12N 15/90*** | (2006.01) |
| ***C07K 14/005*** | (2006.01) |
| ***C07K 14/195*** | (2006.01) |
| ***C12N 9/02*** | (2006.01) |
| ***C12N 9/10*** | (2006.01) |
| ***C12N 9/16*** | (2006.01) |
| ***C12N 9/22*** | (2006.01) |
| ***C12N 9/96*** | (2006.01) |
| ***C12N 15/01*** | (2006.01) |
| ***C12N 15/10*** | (2006.01) |
| ***C12N 15/11*** | (2006.01) |
| ***C12N 15/63*** | (2006.01) |
| ***C12N 15/85*** | (2006.01) |

(52) U.S. Cl.

CPC .......... *C12N 15/907* (2013.01); *C07K 14/005* (2013.01); *C07K 14/195* (2013.01); *C12N 9/0071* (2013.01); *C12N 9/1007* (2013.01); *C12N 9/16* (2013.01); *C12N 9/22* (2013.01); *C12N 9/96* (2013.01); *C12N 15/01* (2013.01); *C12N 15/102* (2013.01); *C12N 15/1031* (2013.01); *C12N 15/11* (2013.01); *C12N 15/63* (2013.01); *C12N 15/85* (2013.01); *C12Y 301/21004* (2013.01); *C07K 2319/00* (2013.01); *C07K 2319/01* (2013.01); *C07K 2319/80* (2013.01); *C12N 2310/20* (2017.05); *C12N 2710/00033* (2013.01); *C12N 2770/00033* (2013.01); *C12N 2800/80* (2013.01); *C12Y 114/11* (2013.01); *C12Y 201/01* (2013.01); *C12Y 301/00* (2013.01)

(58) Field of Classification Search

None

See application file for complete search history.

(56) References Cited

U.S. PATENT DOCUMENTS

| | | | |
|---|---|---|---|
| 4,603,044 | A | 7/1986 | Geho et al. |
| 4,957,773 | A | 9/1990 | Spencer et al. |
| 5,436,150 | A | 7/1995 | Candrasegaran |
| 6,007,988 | A | 12/1999 | Choo et al. |
| 6,013,453 | A | 1/2000 | Choo et al. |
| 6,503,717 | B2 | 1/2003 | Case et al. |
| 6,511,808 | B2 | 1/2003 | Wolffe et al. |
| 7,021,555 | B2 | 4/2006 | Bagnall |
| 7,220,719 | B2 | 5/2007 | Case |
| 7,914,796 | B2 | 3/2011 | Miller |
| 7,919,277 | B2 | 4/2011 | Russell et al. |
| 8,034,598 | B2 | 10/2011 | Miller |
| 8,071,370 | B2 | 12/2011 | Wolffe |
| 8,252,535 | B2 | 8/2012 | Biekle et al. |
| 8,282,920 | B2 | 10/2012 | Heo et al. |
| 8,361,725 | B2 | 1/2013 | Russell et al. |
| 8,697,359 | B1 | 4/2014 | Zhang |
| 8,771,986 | B2 | 7/2014 | Miller |
| 8,865,406 | B2 | 10/2014 | Zhang et al. |
| 8,962,281 | B2 | 2/2015 | Doyon |
| 8,993,233 | B2 | 3/2015 | Zhang et al. |
| 9,023,649 | B2 | 5/2015 | Mali et al. |
| 9,074,199 | B1 | 7/2015 | Chavez et al. |
| 9,322,037 | B2 | 4/2016 | Liu et al. |
| 9,512,446 | B1 | 12/2016 | Joung et al. |
| 9,567,603 | B2 | 2/2017 | Joung et al. |

(Continued)

FOREIGN PATENT DOCUMENTS

| | | |
|---|---|---|
| CN | 103224947 | 7/2013 |
| CN | 103233028 | 8/2013 |

(Continued)

OTHER PUBLICATIONS

Food Proteins and their Applications, 1st ed., Damodaran and Paraf (eds.), Mar. 1997, Chapter 14, 2 pages.

(Continued)

*Primary Examiner* — Suzanne M Noakes

(74) *Attorney, Agent, or Firm* — Fish & Richardson P.C.

(57) ABSTRACT

Methods and constructs for RNA-guided targeting of heterologous functional domains such as transcriptional activators to specific genomic loci.

7 Claims, 21 Drawing Sheets

Specification includes a Sequence Listing.

(56) References Cited

U.S. PATENT DOCUMENTS 9,567,604 B2 2/2017 Joung et al.
9,771,601 B2 9/2017 May et al.
9,885,033 B2 2/2018 Joung
9,926,546 B2 3/2018 Joung et al.
10,011,850 B2 7/2018 Joung et al.
10,093,910 B2 10/2018 Joung et al.
10,119,133 B2 11/2018 Joung et al.
10,138,476 B2 11/2018 Joung et al.
10,266,850 B2 4/2019 Doudna et al.
10,415,059 B2 9/2019 Joung et al.
10,526,589 B2 1/2020 Tsai et al.
10,526,591 B2 1/2020 Joung et al.
10,544,433 B2 1/2020 Joung et al.
10,633,642 B2 4/2020 Joung et al.
10,676,726 B2 6/2020 Gersbach et al.
10,767,168 B2 9/2020 Joung et al.
11,168,338 B2 11/2021 Joung et al.
11,220,678 B2 7/2022 Joung et al.
2002/0160940 A1 10/2002 Case et al.
2002/0164575 A1 11/2002 Case et al.
2003/0017149 A1 1/2003 Hoeffler et al.
2005/0214851 A1 9/2005 Arts et al.
2006/0199190 A1 9/2006 Russell et al.
2007/0020627 A1 1/2007 Barbas, III
2007/0213269 A1 9/2007 Barbas, III et al.
2008/0124725 A1 5/2008 Barrangou et al.
2008/0193470 A1 8/2008 Masignani et al.
2010/0034924 A1 2/2010 Fremaux et al.
2010/0055793 A1 3/2010 Chandrasegaran
2010/0076057 A1 3/2010 Sontheimer et al.
2010/0093617 A1 4/2010 Barrangou et al.
2010/0104690 A1 4/2010 Barrangou et al.
2010/0120043 A1 5/2010 Sood et al.
2010/0183559 A1 7/2010 Van Sinderen et al.
2010/0184624 A1 7/2010 Samuel et al.
2010/0209998 A1 8/2010 Attwood et al.
2010/0209999 A1 8/2010 Altermann et al.
2010/0221185 A1 9/2010 Altermann et al.
2010/0311061 A1 12/2010 Korlach et al.
2010/0317116 A1 12/2010 Flusberg et al.
2011/0002889 A1 1/2011 Barrangou et al.
2011/0092381 A1 4/2011 Sood et al.
2011/0143348 A1 6/2011 Tomigahara et al.
2011/0150852 A1 6/2011 Chambaud et al.
2011/0171647 A1 7/2011 Tomigahara et al.
2011/0189674 A1 8/2011 Tomigahara et al.
2011/0189776 A1 8/2011 Terns et al.
2011/0201007 A1 8/2011 Waller et al.
2011/0201118 A1 8/2011 Yang et al.
2011/0217739 A1 9/2011 Terns et al.
2011/0217791 A1 9/2011 Tomigahara et al.
2011/0223638 A1 9/2011 Wiedenheft et al.
2011/0236530 A1 9/2011 Manoury et al.
2011/0236894 A1 9/2011 Rao et al.
2011/0269119 A1 11/2011 Hutchison et al.
2011/0294873 A1 12/2011 Mermod et al.
2011/0300528 A1 12/2011 Jassim et al.
2011/0300538 A1 12/2011 Barrangou et al.
2012/0027786 A1 2/2012 Gupta et al.
2012/0088676 A1 4/2012 Weill et al.
2012/0115227 A1 5/2012 Cohen-Haguenauer et al.
2012/0151635 A1 6/2012 Coruzzi et al.
2012/0214160 A1 8/2012 Deng et al.
2013/0011516 A1 1/2013 Griffin et al.
2013/0011828 A1 1/2013 Barrangou et al.
2013/0130248 A1 5/2013 Haurwitz et al.
2013/0145497 A1 6/2013 Choi et al.
2013/0150240 A1 6/2013 Newman et al.
2013/0158245 A1 6/2013 Russell et al.
2013/0253040 A1 9/2013 Miller et al.
2013/0288251 A1 10/2013 Horvath et al.
2013/0326645 A1 12/2013 Cost et al.
2013/0326725 A1 12/2013 Shukla et al.
2013/0330778 A1 12/2013 Zeiner et al.
2013/0337454 A1 12/2013 Duchateau et al.
2014/0068797 A1 3/2014 Doudna et al.
2014/0093941 A1 4/2014 Terns et al.
2014/0113376 A1 4/2014 Sorek et al.
2014/0170753 A1 6/2014 Zhang
2014/0179006 A1 6/2014 Zhang
2014/0179770 A1 6/2014 Zhang et al.
2014/0186843 A1 7/2014 Zhang et al.
2014/0186919 A1 7/2014 Zhang et al.
2014/0186958 A1 7/2014 Zhang et al.
2014/0189896 A1 7/2014 Zhang et al.
2014/0199767 A1 7/2014 Barrangou et al.
2014/0201857 A1 7/2014 Fahrenkrug et al.
2014/0212869 A1 7/2014 Sampas et al.
2014/0227787 A1 8/2014 Zhang
2014/0234972 A1 8/2014 Zhang
2014/0242664 A1 8/2014 Zhang et al.
2014/0242699 A1 8/2014 Zhang
2014/0242700 A1 8/2014 Zhang et al.
2014/0242702 A1 8/2014 Chen et al.
2014/0248702 A1 9/2014 Zhang et al.
2014/0256046 A1 9/2014 Zhang et al.
2014/0271987 A1 9/2014 Manoury et al.
2014/0273037 A1 9/2014 Wu
2014/0273226 A1 9/2014 Wu
2014/0273230 A1 9/2014 Chen et al.
2014/0273231 A1 9/2014 Zhang et al.
2014/0273232 A1 9/2014 Zhang et al.
2014/0273234 A1 9/2014 Zhang et al.
2014/0273235 A1 9/2014 Voytas et al.
2014/0287938 A1 9/2014 Zhang et al.
2014/0294773 A1 10/2014 Brouns et al.
2014/0295556 A1 10/2014 Joung et al.
2014/0295557 A1 10/2014 Joung et al.
2014/0298547 A1 10/2014 Sastry-Dent et al.
2014/0304853 A1 10/2014 Ainley et al.
2014/0309487 A1 10/2014 Lee et al.
2014/0310828 A1 10/2014 Lee et al.
2014/0310830 A1 10/2014 Zhang et al.
2014/0315985 A1 10/2014 May et al.
2014/0335063 A1 11/2014 Cannon et al.
2014/0335620 A1 11/2014 Zhang et al.
2014/0349400 A1 11/2014 Jakimo et al.
2014/0356867 A1 12/2014 Peter et al.
2014/0356958 A1 12/2014 Mali et al.
2014/0357530 A1 12/2014 Zhang et al.
2014/0377868 A1 12/2014 Joung et al.
2015/0020223 A1 1/2015 Zhang et al.
2015/0024499 A1 1/2015 Brouns et al.
2015/0024500 A1 1/2015 Yu et al.
2015/0031134 A1 1/2015 Zhang et al.
2015/0044772 A1 2/2015 Zhao
2015/0045546 A1 2/2015 Siksnys et al.
2015/0050699 A1 2/2015 Siksnys et al.
2015/0056629 A1 2/2015 Guthrie-Honea
2015/0067922 A1 3/2015 Yang et al.
2015/0071899 A1 3/2015 Liu et al.
2015/0079681 A1 3/2015 Zhang
2015/0093473 A1 4/2015 Barrangou et al.
2015/0159174 A1 6/2015 Frendeway et al.
2015/0159175 A1 6/2015 Frendeway et al.
2015/0166969 A1 6/2015 Takeuchi et al.
2015/0167000 A1 6/2015 Voytas et al.
2015/0176064 A1 6/2015 Fach et al.
2015/0184139 A1 7/2015 Zhang et al.
2015/0191744 A1 7/2015 Wolfe et al.
2015/0203872 A1 7/2015 Zhang
2015/0232882 A1 8/2015 Zhang et al.
2015/0232883 A1 8/2015 Dahlman et al.
2015/0247150 A1 9/2015 Zhang et al.
2015/0252358 A1 9/2015 Maeder et al.
2015/0291965 A1 10/2015 Zhang et al.
2015/0291966 A1 10/2015 Zhang et al.
2015/0315252 A1 11/2015 Haugwitz et al.
2015/0315576 A1 11/2015 Caliando et al.
2015/0356239 A1 12/2015 Zhang et al.
2015/0376652 A1 12/2015 Kuhn et al.
2016/0010076 A1 1/2016 Joung et al.
2016/0010147 A1 1/2016 Heron
2016/0017301 A1 1/2016 Khalili et al.

(56) References Cited

U.S. PATENT DOCUMENTS

| | | | |
|---|---|---|---|
| 2016/0017366 | A1 | 1/2016 | Chen et al. |
| 2016/0024510 | A1 | 1/2016 | Bikard et al. |
| 2016/0024523 | A1 | 1/2016 | Joung et al. |
| 2016/0024524 | A1 | 1/2016 | Joung et al. |
| 2016/0024529 | A1 | 1/2016 | Carstens et al. |
| 2016/0153003 | A1 | 6/2016 | Joung et al. |
| 2016/0208243 | A1 | 7/2016 | Zhang et al. |
| 2016/0215280 | A1 | 7/2016 | Fanucchi et al. |
| 2016/0312198 | A1 | 10/2016 | Joung et al. |
| 2016/0319281 | A1 | 11/2016 | Tsai et al. |
| 2016/0362688 | A1 | 12/2016 | May et al. |
| 2017/0058271 | A1 | 3/2017 | Joung et al. |
| 2017/0081650 | A1 | 3/2017 | Joung et al. |
| 2017/0152508 | A1 | 6/2017 | Joung et al. |
| 2017/0175136 | A1 | 6/2017 | Stamatoyannopoulos et al. |
| 2017/0327805 | A1 | 11/2017 | Joung et al. |
| 2018/0208921 | A1 | 7/2018 | Joung et al. |
| 2018/0216088 | A1 | 8/2018 | Joung et al. |
| 2018/0340189 | A1 | 11/2018 | Joung et al. |
| 2019/0071657 | A1 | 3/2019 | Joung et al. |
| 2019/0351074 | A1 | 11/2019 | Ahituv et al. |
| 2019/0376090 | A1 | 12/2019 | Joung et al. |
| 2020/0071730 | A1 | 3/2020 | Joung et al. |
| 2020/0149024 | A1 | 5/2020 | Joung et al. |
| 2020/0165587 | A1 | 5/2020 | Tsai et al. |
| 2020/0172899 | A1 | 6/2020 | Joung et al. |
| 2020/0224222 | A1 | 7/2020 | Joung et al. |

FOREIGN PATENT DOCUMENTS

| | | |
|---|---|---|
| CN | 103343120 | 10/2013 |
| CN | 104854241 | 8/2015 |
| EP | 2325332 | 5/2011 |
| JP | 2015-523384 | 8/2015 |
| JP | 2015-527081 | 9/2015 |
| KR | 10-2015-0043540 | 4/2015 |
| WO | WO 2003/072788 | 9/2003 |
| WO | WO 2004/099366 | 11/2004 |
| WO | WO 2007/014275 | 2/2007 |
| WO | WO 2007/025097 | 3/2007 |
| WO | WO 2008/108989 | 9/2008 |
| WO | WO 2010/054108 | 5/2010 |
| WO | WO 2011/017293 | 2/2011 |
| WO | WO 2011/143124 | 11/2011 |
| WO | WO 2012/047726 | 4/2012 |
| WO | WO 2012/093833 | 7/2012 |
| WO | WO 2012/164565 | 12/2012 |
| WO | WO 2013/012674 | 1/2013 |
| WO | WO 2013/098244 | 7/2013 |
| WO | WO 2013/141680 | 9/2013 |
| WO | WO 2013/142578 | 9/2013 |
| WO | WO 2013/169398 | 11/2013 |
| WO | WO 2013/176772 | 11/2013 |
| WO | WO 2014/059255 | 4/2014 |
| WO | WO 2014/089290 | 6/2014 |
| WO | WO 2014/093622 | 6/2014 |
| WO | WO 2014/093655 | 6/2014 |
| WO | WO 2014/093712 | 6/2014 |
| WO | WO 2014/099744 | 6/2014 |
| WO | WO 2014/124284 | 8/2014 |
| WO | WO 2014/127287 | 8/2014 |
| WO | WO 2014/144288 | 9/2014 |
| WO | WO 2014/144592 | 9/2014 |
| WO | WO 2014/144761 | 9/2014 |
| WO | WO 2014/152432 | 9/2014 |
| WO | WO 2014/204578 | 12/2014 |
| WO | WO 2014/204724 | 12/2014 |
| WO | WO 2015/035162 | 3/2015 |
| WO | WO 2015/089364 | 6/2015 |
| WO | WO 2015/099850 | 7/2015 |
| WO | WO 2015/139139 | 9/2015 |
| WO | WO 2015/153940 | 10/2015 |
| WO | WO 2016/073990 | 5/2016 |
| WO | WO 2016/115355 | 7/2016 |
| WO | WO 2016/123578 | 8/2016 |
| WO | WO 2016/141224 | 9/2016 |
| WO | WO 2016/191684 | 12/2016 |
| WO | WO 2016/205759 | 12/2016 |
| WO | WO 2017/031370 | 2/2017 |
| WO | WO 2017/040348 | 3/2017 |
| WO | WO 2018/195540 | 10/2018 |
| WO | WO 2019/222670 | 11/2019 |
| WO | WO 2021/108501 | 6/2021 |
| WO | WO 2021/243289 | 12/2021 |

OTHER PUBLICATIONS

Huang et al., "Design of protein function leaps by directed domain interface evolution," Proceedings of the National Academy of Sciences, USA, May 2008, 105(18):6578-6583.
Makarova et al., "An updated evolutionary classification of CRISPR-Cas systems," Nature Reviews Microbiology, 2015, 13:722-736.
Purcell et al., "Rule-based design of synthetic transcription factors in eukaryotes," ACS Synthetic Biology, Dec. 2013, 3:737-744.
U.S. Appl. No. 61/799,647, filed Mar. 15, 2013, Joung et al.
U.S. Appl. No. 61/838,148, filed Jun. 21, 2013, Joung et al.
Addgene.org [Online]. CRISPR/Cas9 Guide on the web, Jan. 2016, [retrieved on Sep. 13, 2016]. Retrieved from the internet: URL<http://www.addgene.org/CRISPR/guide>/. 146 pages.
Al-Attar et al., "Clustered regularly interspaced short palindromic repeats (CRISPRs): the hallmark of an ingenious antiviral defense mechanism in prokaryotes," Biol Chem., Apr. 2011, 392:277-289.
Alexopoulou et al., "The CMV early enhancer/chicken β actin (CAG) promoter can be used to drive transgene expression during the differentiation of murine embryonic stem cells into vascular progenitors," BMC Cell Biology, 2008, 9:2.
Anders et al., "Structural basis of PAM-dependent target DNA recognition by the Cas9 endonuclease," Nature, 2014, 513:569-573.
Andersson et al., "A Unified Architecture of Transcriptional Regulatory Elements," Trends in Genetics, Aug. 2015, 31(8):426-433.
Anonymous, "2013 Runners-Up. Genetic microsurgery for the masses," Science. Dec. 20, 2013;342(6165):1434-5.
Appela., "Non-natural nucleic acids for synthetic biology", Current Opinion in Chemical Biology, Dec. 2009,13(5-6): 687-696.
Arimondo et al., "Exploring the Cellular Activity of Camptothecin—Triple-Helix-Forming Oligonucleotide Conjugates," Mol. Cell. Biol., 26(1):324-33 (2006).
Arnould et al., "Engineering of large numbers of highly specific homing endonucleases that induce recombination on novel DNA targets," J Mol Biol., 355(3):443-458, Epub Nov. 15, 2005.
Arnould et al., "The I-CreI meganuclease and its engineered derivatives: applications from cell modification to gene therapy," Protein Eng Des Sel., 24(1-2):27-31, Epub Nov. 3, 2010.
Arora et al., "Residues 1-254 of anthrax toxin lethal factor are sufficient to cause cellular uptake of fused polypeptides," J. Biol. Chem., Feb. 1993, 268:3334-41.
AU Office Action in Australian Application No. 2014227653, dated Nov. 18, 2016, 3 pages.
AU Office Action in Australian Application No. 2017204909, dated Aug. 8, 2018, 8 pages.
AU Office Action in Australian Appln. No. 2014239665, dated Sep. 5, 2019, 4 pages.
AU Office Action in Australian Appln. No. 2014370416, dated Apr. 6, 2020, 3 pages.
AU Office Action in Australian Appln. No. 2019204675, dated Aug. 17, 2020, 4 pages.
AU Office Action in Australian Appln. No. 2020207840, dated Nov. 5, 2021, 4 pages.
Auer et al., "Highly efficient CRISPR/Case9-mediated known-in in zebrafish by homology-independent DNA repair," Genome Res., 2014, 24:142-153.
Bae et al., "Cas-OFFinder: a fast and versatile algorithm that searches for potential off-target sites of Cas9 RNA-guided endonucleases," Bioinformatics, 2014, 30:1473-1475.
Bae et al., "Human zinc fingers as building blocks in the construction of artificial transcription factors," Nat Biotechnol., 21(3):275-280, Epub Feb. 18, 2003.

(56) References Cited

OTHER PUBLICATIONS

Barker et al., "Increased DNA microarray hybridization specificity using sscDNA targets," BMC Genomics, Apr. 2005, 6:57, 8 pages.
Baron-Benhamou et al., "Using the λN Peptide to Tether Proteins to RNAs," Methods Mole Biol., Jan. 2004, 257:135-153.
Barrangou & May, "Unraveling the potential of CRISPR-Cas9 for gene therapy," Expert Opin. Biol. Ther., 2015, 15:311-314.
Barrangou et al., "CRISPR Provides Acquired Resistance Against Viruses in Prokaryotes," Sci., 2007, 315:1709-1712.
Barrangou, "RNA-mediated programmable DNA cleavage," Nature Biotechnol., 2012, 30(9):836-838.
Bassett et al., "Highly efficient targeted mutagenesis of *Drosophila* with the CRISPR/Cas9 system," Cell Reports, 2013, 4:220-228.
Beerli and Barbas, "Engineering polydactyl zinc-finger transcription factors," Nat Biotechnol., 20(2):135-141, Feb. 2002.
Beerli et al., "Toward controlling gene expression at will: specific regulation of the erbB-2/HER-2 promoter by using polydactyl zinc finger proteins constructed from modular building blocks," PNAS USA, 1998, 95:14628-14633.
Belhaj et al., "Plant genome editing made easy: targeted mutagenesis in model and crop plants using the CRISPR/Cas system," Plant Methods, 2013, 9:39, 10 pages.
Bello et al., "Hypermethylation of the DNA repair gene MGMT: association with TP53 G:C to A:T transitions in a series of 469 nervous system tumors," Mutat. Res., Oct. 2004, 554:23-32.
Berg, "Proposed structure for the zinc-binding domains from transcription factor IIIA and related proteins," Proc Natl Acad Sci U S A., 85(1):99-102, Jan. 1988.
Bikard et al., "Programmable repression and activation of bacterial gene expression using an engineered CRISPR-Cas system," Nucleic Acid Res., Jun. 4, 20131(15):7429-7437.
Binz et al. "Designing repeat proteins: well-expressed, soluble and stable proteins from combinatorial libraries of consensus ankyrin repeat proteins," Journal of Molecular Biology, 2003, 332(2): 489-503.
Bird et al. "A dual role for zinc fingers in both DNA binding and zinc sensing by the Zap1 transcriptional activator," The EMBO Journal, 2000, 19(14), 3704-3713.
Bitinaite et al., "FoκI dimerization is required for DNA cleavage," Proc. Natl. Acad. Sci. USA, 1998, 95:10570-10575.
Blackburn et al., "The CRISPR System—Keeping Zebrafish Gene Targeting Fresh," Zebrafish, 2013, 10(1):116-118.
Blaese et al., "T lymphocyte-directed gene therapy for ADA-SCID: initial trial results after 4 years," Science, Oct. 1995, 270:475-480.
BLAST sequence alignment: Query = Applicants SEQ ID No. 26 and Sbjct = Jinek et al.'s SEQ ID No. 8 from W02013176772 (Retrieved from the Internet <https://blast.ncbi.nlm.nih.gov/Blast.cgi>, retrieved on Feb. 1, 2018, 3 pages.
Boch et al., "Breaking the code of DNA binding specificity of TAL-type III effectors," Science, Dec. 11, 2009;326(5959):1509-12.
Bogdanove & Voytas, "TAL Effectors: Customizable Proteins for DNA Targeting," Science, 333:1843-1846 (2011).
Bogdanove et al., "TAL effectors: finding plant genes for disease and defense," Curr. Opin. Plant Biol., 13:394-401 (2010).
Bolukbasi et al. "DNA-binding-domain fusions enhance the targeting range and precision of Cas9," Nature Methods, 2015, 12.12 : 1150-1156.
BR Office Action in Brazilian Appln. No. BR112015023489-5, dated Oct. 3, 2019, 6 pages (with English abstract).
Burgess, "A CRISPR genome-editing tool," Nature Reviews Genetics 14, 80-81 (Feb. 2013).
Burnett et al., "Conditional macrophage ablation in transgenic mice expressing a Fas-based suicide gene," J. Leukoc. Biol., Apr. 2004, 75(4):612-623.
Butler and Kadonaga, "The RNA polymerase II core promoter: a key component in the regulation of gene expression," Genes & Dev., 2002, 16:2583-2592.
CA Office Action in Canadian Application No. 2907198, dated May 14, 2018, 3 pages.
CA Office Action in Canadian Application No. 2907198, dated Aug. 24, 2017, 10 pages.
CA Office Action in Canadian Appln. No. 2,906,553, dated Jan. 27, 2020, 4 pages.
CA Office Action in Canadian Appln. No. 2,906,553, dated May 28, 2021, 3 pages.
CA Office Action in Canadian Appln. No. 2,906,724, dated Feb. 5, 2020, 4 pages.
CA Office Action in Canadian Appln. No. 2,935,032, dated Sep. 10, 2020, 5 pages.
Carbonetti et al., "Use of pertussis toxin vaccine molecule PT19K/129G to deliver peptide epitopes for stimulation of a cytotoxic T lymphocyte response," Abstr. Annu. Meet. Am. Soc. Microbiol., 1995, 95:295.
Carroll et al., "Design, construction and in vitro testing of zinc finger nucleases," Nat Protoc., 1(3):1329-1341, 2006.
Carroll, "A CRISPR Approach to Gene Targeting," Molecular Therapy, 2012, 20(9):1658-1660.
Carroll, "Progress and prospects: zinc-finger nucleases as gene therapy agents," Gene Ther., 15(22):1463-1468, Epub Sep. 11, 2008.
Carroll, "Staying on target with CRISPR-Case," Nat Biotechnol., 2013, 31(9):807-809.
Castellano et al., "Inducible recruitment of Cdc42 or WASP to a cell-surface receptor triggers actin polymerization and filopodium formation," Curr. Biol., 1999, 9(7): 351-360.
Cathomen and Joung, "Zinc-finger nucleases: the next generation emerges," Mol. Ther., 2008, 16:1200-1207.
Cermak et al., "Efficient design and assembly of custom TALEN and other TAL effector-based constructs for DNA targeting," Nucleic Acids Res., 39:e82, p. 1-11 (2011).
Chaikind et al., "Targeted DNA Methylation Using an Artificially Bisected M.Hhal Fused to Zinc Fingers," PLoS ONE, 7(9):E44852 pp. 1-11 (2012).
Chang et al., "Genome editing with RNA-guided Cas9 nuclease in zebrafish embryos," Cell Res., 2013, 23:465-472.
Chen & Zhao, "A highly sensitive selection method for directed evolution of homing endonucleases," Nucleic Acids Res., 2005, 33(18):e154.
Chen et al., "Cut Site Selection by the Two Nuclease Domains of the Cas9 RNA-guided Endonuclease," J Biol Chem. May 9, 2014; 289(19):13284-94.
Chen et al., "Dynamic imaging of genomic loci in living human cells by an optimized CRISPR/Cas system," Cell, 2013, 155(7):1479-1491.
Chen et al., "Efficient genome editing in Caenorhabditis elegans by CRISPR-targeted homologous recombination," Nucleic Acids Res., 2013, 41(20):e193, 6 pages.
Chen et al., "Induced DNA demethylation by targeting Ten-Eleven Translocation 2 to the human ICAM-1 promoter," Nucleic Acids Res., 42(3):1563-1574, Epub Nov. 4, 2013.
Cheng et al., "Multiplexed activation of endogenous genes by CRISPR-on, an RNA-guided transcriptional activator system," Cell Res., Oct. 2013, 23(10):1163-71.
Chim et al., "Methylation profiling in multiple myeloma," Leuk. Res., Apr. 2004, 28:379-85.
Chiu et al., "Transgene-free genome editing in Caenorhabditis elegans using CRISPR-Cas," Genetics, Nov. 2013, 195(3):1167-71.
Cho et al., "Analysis of off-target effects of CRISPR/Case-derived RNA-guided endonucleases and nickases," Genome Res., 2014, 24:132-141.
Cho et al., "Targeted genome engineering in human cells with the Cas9 RNA-guided endonuclease," Nat Biotechnol., 2013, 31:230-232.
Choo and Klug, "Toward a code for the interactions of zinc fingers with DNA: selection of randomized fingers displayed on phage," Proc Natl Acad Sci U S A., 91(23):11163-11167, Nov. 8, 1994.
Chothia et al. "Domain association in immunoglobulin molecules: the packing of variable domains," Journal of Molecular Biology, 1985, 186(3): 651-663.
Choudhury et al., "CRISPR-dCas9 mediated TET1 targeting for selective DNA demethylation at BRCA1 promoter," Oncotarget, 2016, 7(29):46545-46556.

(56) References Cited

OTHER PUBLICATIONS

Christian et al., "Targeting DNA Double-Strand Breaks with TAL Effector Nucleases," Genetics, 2010, 186:757-761 (2010).
Chylinski et al., "Classification and evolution of type II CRISPR-Cas systems," Nucleic Acids Res. 2014;42(10):6091-105.
Chylinski et al., "The tracrRNA and Cas9 families of type II CRISPR-Cas immunity systems," RNA Biol., 2013, 10(5):726-737.
Clark-Curtiss and Curtiss, "[23] Analysis of recombinant DNA using *Escherichia coli* minicells," Methods in Enzymology, 1983, 101:347-362.
CN Action in Chinese Appln. No. 201480026276.5, dated Nov. 1, 2019, 19 pages (with English translation).
CN Action in Chinese Appln. No. 201480027950.1, dated Sep. 20, 2019, 9 pages (with English translation).
CN Office Action in Canadian Application No. 2907198, dated Jul. 8, 2016, 4 pages.
CN Office Action in Chinese Application No. 2014800261133.4, dated May 31, 2017.
CN Office Action in Chinese Application No. 201480026133.4, dated Feb. 12, 2018, 22 pages (with English translation).
CN Office Action in Chinese Application No. 201480026276.5, dated Apr. 17, 2018, 12 pages (with English translation).
CN Office Action in Chinese Application No. 201480027950.1, dated Mar. 23, 2018, 13 pages (with English translation).
CN Office Action in Chinese Application No. 201480027950.1, dated Oct. 18, 2018, 6 pages.
CN Office Action in Chinese Application No. 201480076396.6, dated Feb. 19, 2019, 16 pages (with English translation).
CN Office Action in Chinese Appln. No. 201480026276.5, dated Mar. 26, 2020, 10 pages (with English translation).
CN Office Action in Chinese Appln. No. 201480026276.5, dated Mar. 1, 2021, 9 pages (with English translation).
CN Office Action in Chinese Appln. No. 201480026276.5, dated Nov. 13, 2020, 9 pages (with English translation).
CN Office Action in Chinese Appln. No. 201480076396.6, dated May 21, 2020, 14 pages (with English translation).
CN Office Action in Chinese Appln. No. 201480076396.6, dated Jan. 5, 2021, 7 pages (with English translation).
CN Office Action in Chinese Appln. No. 201680063266.8, dated Dec. 11, 2020, 15 pages (with English translation).
Colley et al., "Conversion of a Golgi Apparatus Sialyltransferase to a Secretory Protein by Replacement of the NH2-terminall Signal Anchor with a Signal Peptide," J. Biol. Chem., 1989, 264:17619-22.
Cong et al., "Multiplex genome engineering using CRISPR/Cas systems," Science, 2013, 339:819-823 (Author Manuscript).
Conklin, "Sculpting genomes with a hammer and chisel," Nature Methods, 2013, 10(9):839-840.
Costa et al., "REELIN and schizophrenia: a disease at the interface of the genome and the epigenome," Mol. Interv., Feb. 2002, 2:47-57.
Crabtree and Schreiber, "Three-part inventions: intracellular signaling and induced proximity," Trends Biochem. Sci., Nov. 1996, 21(11):418-422.
Cradick et al., "CRISPR/Cas9 systems targeting beta-globin and CCR5 genes have substantial off-target activity," Nucleic Acids Res., 2013, 41(20):9584-92.
D'Avignon et al., "Site-specific experiments on folding/unfolding of Jun coiled coils: thermodynamic and kinetic parameters from spin inversion transfer nuclear magnetic resonance at leucine-18," Biopolymers, 83(3):255-267, Oct. 15, 2006.
De Souza, "RNA-guided gene editing," Nat Methods, Mar. 2013, 10(3):189.
De Zhu, "The altered DNA methylation pattern and its implications in liver cancer," Cell. Res., 2005, 15:272-80.
Deltcheva et al., "CRISPR RNA maturation by trans-encoded small RNA and host factor Rnase III," Nature, 2011, 471(7340):602-607 (Author Manuscript).
Demidov et al., "Two sides of the coin: affinity and specificity of nucleic acid interactions," Trends Biochem. Sci., Feb. 2004, 29(2):62-71.
Deveau et al., "Phage response to CRISPR-encoded resistance in Streptococcus thermophilus," J Bacteriol., Feb. 2008, 190(4):1390-400.
Dicarlo et al., "Genome engineering in *Saccharomyces cerevisiae* using CRISPR-Cas systems," Nucleic Acids Res., 2013, 41(7):4336-43.
Dickinson et al., "Engineering the Caenorhabditis elegans genome using Cas9-triggered homologous recombination," Nat Methods., Oct. 2013, 10(10):1028-34.
Ding et al., "Enhanced efficiency of human pluripotent stem cell genome editing through replacing TALENs with CRISPRs," Cell Stem Cell., Apr. 4, 2013, 12(4):393-4 (Author Manuscript).
Donnelly et al., "Targeted delivery of peptide epitopes to class I major histocompatibility molecules by a modified Pseudomonas exotoxin," PNAS, Apr. 1993, 90:3530-34.
Doudna and Charpentier, "Genome editing. The new frontier of genome engineering with CRISPR-Cas9," Science, Nov. 2014, 346:1258096, 11 pages.
Doyon et al., "Directed Evolution and Substrate Specificity Profile of Homing Endonuclease I-SceI," J. Am. Chem. Soc., 2006, 128:2477-2484.
Doyon et al., "Heritable targeted gene disruption in zebrafish using designed zinc-finger nucleases," Nat Biotechnol., Jun. 2008, 26:702-708.
Dranoff et al., "A phase I study of vaccination with autologous, irradiated melanoma cells engineered to secrete human granulocyte-macrophage colony stimulating factor," Hum. Gene Ther., Jan. 1997, 8(1):111-23.
Dunbar et al., "Retrovirally Marked CD34-Enriched Peripheral Blood and Bone Marrow Cells Contribute to Long-Term Engraftment After Autologous Transplantation ," Blood, Jun. 1995, 85:3048-3057.
Eisenschmidt et al., "Developing a programmed restriction endonuclease for highly specific DNA cleavage," Nucleic Acids Res., 33(22):7039-47 (2005).
Ellem et al., "A case report: immune responses and clinical course of the first human use of granulocyte/macrophage-colony-stimulating-factor-transduced autologous melanoma cells for immunotherapy," Immunol Immunother., Mar. 1997, 44:10-20.
Elrod-Erickson et al., "High-resolution structures of variant Zif268-DNA complexes: implications for understanding zinc finger-DNA recognition," Structure, 6(4):451-464, Apr. 15, 1998.
EP Brief Communcation in European Appln. No. 14763916.5, dated Feb. 9, 2021, 68 pages.
EP Extended European Search Report in European Appln. No. 16842722.7, dated Jun. 7, 2019, 10 pages.
EP Extended European Search Report in European Appln. No. 20172393.9, dated Oct. 8, 2020, 12 pages.
EP Office Action in European Application No. 14763916.5, dated Mar. 27, 2017, 6 pages.
EP Office Action in European Application No. 14763916.5, dated Oct. 26, 2017, 5 pages.
EP Office Action in European Application No. 14764117.9, dated Jan. 4, 2018, 4 pages.
EP Office Action in European Application No. 14764159.1, dated Jun. 16, 2017, 4 pages.
EP Office Action in European Application No. 14764159.1, dated Nov. 21, 2017.
EP Office Action in European Application No. 14768877.4, dated Jan. 8, 2018, 4 pages.
EP Office Action in European Application No. 14768877.4, dated Jul. 14, 2017, 4 pages.
EP Office Action in European Application No. 14875819.6, dated Jun. 19, 2018.
EP Office Action in European Appln. No. 14764117.9, dated Nov. 7, 2019, 6 pages.
EP Office Action in European Appln. No. 14764117.9, dated Jul. 9, 2020, 4 pages.
EP Office Action in European Appln. No. 14875819.6 dated Dec. 2, 2019, 4 pages.
EP Office Action in European Appln. No. 16842722, dated Sep. 30, 2020, 4 pages.

(56) References Cited

OTHER PUBLICATIONS

EP Office Action in European Appln. No. 16842722.7, dated Mar. 5, 2020, 5 pages.
EP Office Action in European Appln. No. 18208105.9, dated Nov. 14, 2019, 3 pages.
EP Office Action in European Appln. No. 18208105.9, dated Jul. 16, 2020, 4 pages.
EP Office Action in European Appln. No. 20171165.2, dated Sep. 8, 2021, 4 pages.
EP Supplementary European Search Report in EP Appln. No. EP 17859458, dated Mar. 31, 2020, 7 pages.
Esteller et al., "A Gene Hypermethylation Profile of Human Cancer," Cancer Res., Apr. 2001, 61:3225-9.
Esteller et al., "Promoter Hypermethylation and BRCA1 Inactivation in Sporadic Breast and Ovarian Tumors," J. Natl. Cancer Inst., Apr. 2000, 92:564-9.
Esvelt et al., "Orthogonal Cas9 proteins for RNA-guided gene regulation and editing," Nat Methods, Nov. 2013, 10(11):1116-21.
European Partial Supplementary Search Report in European Application No. 14764117.9, dated Aug. 11, 2016, 7 pages.
European Search Report in European Application No. 14763916.5, dated Jul. 27, 2016, 10 pages.
Extended European Search Report in Application No. 14875819.6, dated Jun. 8, 2017.
Extended European Search Report in Application No. 18208105.9, dated Jan. 15, 2019, 5 pages.
Extended European Search Report in European Application No. 14764159.1, dated Aug. 10, 2016, 7 pages.
Extended European Search Report in European Application No. 14768877.4, dated Aug. 10, 2016.
Farboud and Meyer, "Dramatic Enhancement of Genome Editing by CRISPR/Cas9 Through Improved Guide RNA Design," Genetics, 2015, 199:959-971.
Fisher et al., "A scalable, fully automated process for construction of sequence-ready human exome targeted capture libraries," Genome Biol., 2011, 12-R1.
Fonfara et al., "Phylogeny of Cas9 determines functional exchangeability of dual-RNA and Cas9 among orthologous type II CRISPR-Cas systems." Nucleic Acids Res., Feb. 2014, 42(4):2577-90.
Freeman et al., "Inducible Prostate Intraepithelial Neoplasia with Reversible Hyperplasia in Conditional FGFR1-Expressing Mice," Cancer Res., Dec. 2003, 63(23):8256-8563.
Friedland et al., "Heritable genome editing in C. elegans via a CRISPR-Cas9 system," Nature Methods 10(8): 741-743, 2013 (Author Manuscript).
Fu et al, Targeted genome editing in human cells using CRISPR/Cas nucleases and truncated guide RNAs, Methods in Enzymology, Nov. 2014, 546: 21-45.
Fu et al., "High-frequency off-target mutagenesis induced by CRISPR-Cas nucleases in human cells," Nat Biotechnol., 2013, 31:822-826 (Author Manuscript).
Fu et al., "Improving CRISPR-Cas nuclease specificity using truncated guide RNAs," Nat. Biotechnol. Mar. 2014, 32:279-284.
Gabriel et al., "An unbiased genome-wide analysis of zinc-finger nuclease specificity," Nat Biotechnol., 2011, 29:816-823.
Gagnon et al., "Efficient mutagenesis by Cas9 protein-mediated oligonucleotide insertion and large-scale assessment of single-guide RNAs," PLoS One, May 2014, 9, e98186.
Gaj et al., "ZFN, TALEN, and CRISPR/Cas-based methods for genome engineering," Trends in Biotechnology, Jul. 2013, 31(7):397-405.
Gao et al., "Hypermethylation of the RASSF1A gene in gliomas," Clin. Chim. Acta., Nov. 2004, 349:173-9.
Garcia-Bustos et al., "Nuclear protein localization," Biochim. Biophys. Acta, Mar. 1991, 1071:83-101.
Garneau et al., "The CRISPR/Cas bacterial immune system cleaves bacteriophage and plasmid DNA," Nature, Nov. 4, 2010, 468(7320):67-71.
Gasiunas and Siksnys,"RNA-dependent DNA endonuclease Cas9 of the CRISPR system: Holy Grail of genome editing?" Trends Microbiol., 2013, 21(11):562-567.
Gasiunas,"Cas9-crRNA ribonucleoprotein complex mediates specific DNA cleavage for adaptive immunity in bacteria," Proc Natl Acad Sci U S A, Sep. 25, 2012, 109(39):E2579-86.
Gehrke et al., "An APOBEC3A-Cas9 base editor with minimized bystander and off-target activities," Nature Biotechnology, Oct. 2018, 36(10):977, 10 pages.
Geibler et al., "Transcriptional Activators of Human Genes with Programmable DNA-Specificity ," PLoS ONE, 6:e19509 (2011).
GenBank Accession No. AKS40380.1, "Cas9 [Synthetic plasmid pFC330]," Aug. 2, 2015, 1 page.
Gilbert et al., "CRISPR-mediated modular RNA-guided regulation of transcription in eukaryotes," Cell, 2013, 154(2):442-51.
Gossen et al., "Tight control of gene expression in mammalian cells by tetracycline-responsive promoters," Proc. Natl. Acad. Sci., Jun. 1992, 89:5547-5551.
Graef et al., "Proximity and orientation underlie signaling by the non-receptor tyrosine kinase ZAP70," Embo. J., 1997, 16(18):5618-5628.
Gratz et al., "CRISPR/Cas9-mediated genome engineering and the promise of designer flies on demand," Fly (Austin), Oct.-Dec. 2013, 7(4):249-55.
Gratz et al., "Genome engineering of *Drosophila* with the CRISPR RNA-guided Cas9 nuclease," Genetics, 2013, 194(4):1029-35.
Grizot et al., "Generation of redesigned homing endonucleases comprising DNA-binding domains derived from two different scaffolds," Nucleic Acids Res., 38(6):2006-2018, Epub Dec. 21, 2009.
Gross and Garrard, "Nuclease Hypersensitive Sites in Chromatin," Annu. Rev. Biochem., Jul. 1988, 57:159-97.
Guilinger et al. "Broad specificity profiling of TALENs results in engineered nucleases with improved DNA-cleavage specificity," Nature Methods, 2014, 11(4), 429-435.
Guilinger et al., "Fusion of catalytically inactive Cas9 to Fokl nuclease improves the specificity of genome modification," Nat Biotechnol., Apr. 2014, 32(6):577-583.
Guo et el., "Hydroxylation of 5-Methylcytosine by TET1 Promotes Active DNA Demethylation in the Adult Brain ," Cell, 145:423-434 (2011).
Haft et al., "A Guild of 45 CRISPR-Associated (Cas) Protein Families and multiple CRISPER/cas Subtypes Exist in Prokaryotic Genomes," PLOS, 2005, 1(6):0474-0483.
Hale et al., "Essential features and rational design of CRISPR RNAs that function with the Case RAMP modlule complex to cleave RNAs," Mol Cell., 2012, 45(3):292-302 (Author Manuscript).
Hamers-Casterman et al. "Naturally occurring antibodies devoid of light chains," Nature, 1993, 363(6428): 446-448.
Hammond et al., "A CRISPR-Cas9 gene drive system targeting female reproduction in the malaria mosquito vector *Anopheles gambiae*," Nature Biotechnology, 2016, 34:78-83.
Han et al., "CTCF Is the Master Organizer of Domain-Wide Allele-Specific Chromatin at the H19/Igf2 Imprinted Region," Mol Cell Biol., Feb. 2008, 28(3):1124-35.
Han et al., "Ligand-directed retroviral targeting of human breast cancer cells, " PNAS, Oct. 1995, 92:9747-51.
Harikrishna et al., "Construction and function of fusion enzymes of the human cytochrome P450scc system," DNA Cell Biol., 12(5):371-379, Jun. 1993.
Harrison, "A structural taxonomy of DNA-binding domains, " Nature, 353(6346): 715-719, Oct. 24, 1991.
Haurwitz et al., "Sequence- and Structure-Specific RNA Processing by a CRISPR Endonuclease," Science, Sep. 2010, 329(5997):1355-8.
Haurwitz, "The CRISPR endoribonuclease Csy4 utilizes unusual sequence and structures pecific mechanisms to recognize and process crRNAs," Thesis. May 8, 2012 (May 8, 2012), University of California, Berkeley, pp. 1-120. Retrieved from the Internet:<http://escholarship.org/uc/item/0rh5940p> on Dec. 26, 2014 (Dec. 26, 2014). entire document.
He et al., "Tet-Mediated Formation of 5-Carboxylcytosine and Its Excision by TDG in Mammalian DNA," Science, 333:1303-1307 (2011).

(56) References Cited

OTHER PUBLICATIONS

Hockemeyer et al., "Genetic engineering of human ES and iPS cells using TALE nucleases," Nat Biotechnol., 2011, 29:731-734 (Author Manuscript).
Horii et al., "Generation of an ICF Syndrome Model by Efficient Genome Editing of Human Induced Pluripotent Stem Cells using the CRISPR System," Int J Mol Sci., 2013, 14:19774-19781.
Horvath and Barrangou, "CRISPR/Cas, the immune system of bacteria and archaea," Science, 2010, 327:167-170.
Horvath et al., "Diversity, activity, and evolution of CRISPR loci in *Streptococcus thermophilus*," J. Bacteriol., Feb. 2008, 190:1401-1412.
Hou et al., "Efficient genome engineering in human pluripotent stem cells using Cas9 from Neisseria meningitidis," Proc Natl Acad Sci U S A, Sep. 24, 2013, 110(39):15644-9.
Hsu et al., "Development and Applications of CRISPR-Cas9 for Genome Engineering," Cell, 2014, 157(6):1262-1278.
Hsu et al., "DNA targeting specificity of RNA-guided Cas9 nucleases," Nat Biotechnol., 2013, 31:827-832.
Huang et al., "Heritable gene targeting in zebrafish using customized TALENs," Nat. Biotechnol., 29:699-700 (2011).
Hwang et al., "Efficient In Vivo Genome Editing Using RNA-Guided Nucleases," Nat Biotechnol., 2013, 31:227-229 (Author Manuscript).
Hwang et al., "Heritable and Precise Zebrafish Genome Editing Using a CRISPR-Cas System," PLoS One, 2013, 8(7):e68708, 9 pages.
IL Office Action in Israeli Application No. 241671, dated Sep. 13, 2018, 8 pages (with English translation).
IL Office Action in Israeli Appln. No. 241671, dated May 21, 2020, 6 pages (with English translation).
IL Office Action in Israeli Appln. No. 241671, dated Aug. 1, 2019, 5 pages (with English translation).
IN Office Action in Indian Appln. No. 8445/DELNP/2015, dated Nov. 18, 2019, 7 pages.
International Preliminary Report on Patentability in International Application No. PCT/US2013/043075, dated Dec. 2, 2014, 7 pages.
International Preliminary Report on Patentability in International Application No. PCT/US2014/028630, mailed Sep. 15, 2015, 8 pages.
International Preliminary Report on Patentability in International Application No. PCT/US2014/056416, dated Jun. 28, 2016, 7 pages.
International Preliminary Report on Patentability in International Application No. PCT/US2016/49147, dated Mar. 6, 2018, 8 pages.
International Search Report and Written Opinion in International Application No. PCT/US16/49147, mailed on Dec. 23, 2016, 12 pages.
International Search Report and Written Opinion in International Application No. PCT/US2013/043075, dated Sep. 26, 2013, 10 pages.
International Search Report and Written Opinion in International Application No. PCT/US2014/028630, mailed Jul. 24, 2014, 9 pages.
International Search Report and Written Opinion in International Application No. PCT/US2014/029068, mailed Nov. 5, 2014, 15 pages.
International Search Report and Written Opinion in International Application No. PCT/US2014/029304, mailed Nov. 14, 2014, 17 pages.
International Search Report and Written Opinion in International Application No. PCT/US2014/035162, mailed Oct. 14, 2014, 10 pages.
International Search Report and Written Opinion in International Application No. PCT/US2014/056416, dated Apr. 3, 2015, 11 pages.
International Search Report and Written Opinion in International Appln. No. PCT/US2021/034996, dated Sep. 16, 2021, 12 pages.
International Search Report in International Application No. PCT/US2014/054291, mailed on Mar. 27, 2015, 6 pages.
Invitation to Pay Additional Fees and, Where Applicable, Protest Fee in International Application No. PCT/US2014/029068, mailed Aug. 20, 2014, 3 pages.
Invitation to Pay Additional Fees and, Where Applicable, Protest Fee in International Application No. PCT/US2014/029304, mailed Jul. 30, 2014, 3 pages.
Invitation to Pay Additional Fees and, Where Applicable, Protest Fee in International application No. PCT/US2016/49147, mailed on Oct. 31, 2016, 2 pages.
Isalan et al., "A rapid, generally applicable method to engineer zinc fingers illustrated by targeting the HIV-1 promoter," Nat. Biotechnol., 19(7):656-660, Jul. 2001.
Ishino et al., "Nucleotide sequence of the iap gene, responsible for alkaline phosphatase isozyme conversion in *Escherichia coli*, and identification of the gene product," J Bacteriol., Dec. 1987, 169(12):5429-33.
Ito et al., "Tet proteins can convert 5-methylcytosine to 5-formylcytosine and 5-carboxylcytosine," Science, 333(6047):1300-1303, Sep. 2, 2011.
Iyer et al., "Prediction of novel families of enzymes involved in oxidative and other complex modifications of bases in nucleic acids," Cell Cycle, Jun. 1, 2009, 8(11):1698-710.
Iyer et al., Supplementary Material for "Prediction of novel families of enzymes involved in oxidative and other complex modifications of bases in nucleic acids," Cell Cycle, Jun. 1, 2009, 8(11):1698-710, [retrieved on Dec. 22, 2015]. Retrieved from the Internet: URL <ftp://ftp.ncbi.nih.gov/pub/aravind/DONS/supplementary_material_DONS.html>.
Jamieson et al., "In vitro selection of zinc fingers with altered DNA-binding specificity," Biochemistry, 33(19):5689-5695, May 17, 1994.
Jansen et al., "Identification of genes that are associated with DNA repeats in prokaryotes," Mol Microbiol., Mar. 2002, 43(6):1565-75.
Jiang et al., "CRISPR-assisted editing of bacterial genomes," Nat Biotechnol., 2013, 31:233-239 (Author Manuscript).
Jiang et al., "RNA-guided editing of bacterial genomes using CRISPR-Cas systems," Nature Biotechnology, Mar. 2013, 31: 233-239.
Jiang et al., "Structural Biology. A Cas9-guide RNA complex preorganized for target DNA recognition," Science, Jun. 2015, 348:1477-1481.
Jinek et al., "A programmable dual-RNA-guided DNA endonuclease in adaptive bacterial immunity," Science, 2012, 337:816-821.
Jinek et al., "RNA-programmed genome editing in human cells," Elife, 2013, 2:e00471, 9 pages.
Jinek et al., "Structures of Cas9 Endonucleases Reveal RNA-Mediated Conformational Activation," Science. Mar. 14, 2014; 343(6176):1247997.
Jinek et al., "Supplementary Materials for a Programmable Dual-RNA-Guided DNA Endonuclease in Adaptive Bacterial Immunity," Science Express, 2012, 37 pages.
Josephs et al., "Structure and specificity of the RNA-guided endonuclease Cas9 during DNA interrogation, target binding and cleavage," Nucleic Acids Res., Sep. 2015, 43:8924-8941.
Joung and Sander, "TALENs: a widely applicable technology for targeted genome editing," Nat Rev Mol Cell Biol., 14(1):49-55, Epub Nov. 21, 2012.
Joung et al., "Reply to "Successful genome editing with modularly assembled zinc finger nucleases"," Nat. Methods, Jan. 2010, 7:91-92.
JP Office Action in Japanese Application No. 2016-502406, dated Jun. 12, 2018, 23 pages (with English translation).
JP Office Action In Japanese Application No. 2016-502853, dated Jun. 12, 2018, 15 pages (with English translation).
JP Office Action in Japanese Application No. 2016-502976, dated Apr. 2, 2019, 16 pages (with English translation).
JP Office Action in Japanese Application No. 2016-502976, dated May 8, 2018, 16 pages (with English translation).
JP Office Action in Japanese Application No. 2016-542968, dated Sep. 18, 2018 (with English translation).
JP Office Action in Japanese Application No. 2019-210428, dated Dec. 8, 2020, 12 pages (with English translation).

(56) References Cited

OTHER PUBLICATIONS

JP Office Action in Japanese Appln. No. 2016-502406, dated May 31, 2019, 24 pages (with English translation).
JP Office Action in Japanese Appln. No. 2016-502853, dated May 29, 2019, 7 pages (with English translation).
JP Office Action in Japanese Appln. No. 2016-502976, dated Nov. 26, 2019, 9 pages (with English translation).
JP Office Action in Japanese Appln. No. 2016-542968, dated Jul. 30, 2019, 8 pages (with English translation).
JP Office Action in Japanese Appln. No. 2018-510914, dated Jan. 21, 2020, 11 pages (with English translation).
JP Office Action in Japanese Appln. No. 2018-510914, dated Jul. 14, 2020, 7 pages (with English translation).
JP Office Action in Japanese Appln. No. 2019-153881, dated Jan. 21, 2020, 8 pages (with English translation).
JP Office Action in Japanese Appln. No. 2019-176599, dated Jul. 27, 2021, 6 pages (with English translation).
JP Office Action in Japanese Appln. No. 2019-176599, dated Sep. 8, 2020, 4 pages (with English translation).
JP Office Action in Japanese Appln. No. 2019-218086, dated Feb. 2, 2021, 4 pages (with English translation).
JP Pretrial Reexamination Report in Japanese Appln. No. 2016-502976, dated Jun. 23, 2020, 11 pages (with English translation).
Karkare and Bhatnagar, "Promising nucleic acid analogs and mimics: characteristic features and applications of PNA, LNA, and morpholino", Applied Microbiology and Biotechnology, May 2006, 71(5): 575-586.
Karmirantzou and Harnodrakas, "A Web-based classification system of DNA-binding protein families," Protein Eng. 14(7):465-472, Jul. 2001.
Karvelis et al., "crRNA and tracrRNA guide Cas9-mediated DNA interference in *Streptococcus thermophilus*," RNA Biol., 2013, 10(5):841-851.
Katic and Groβhans, "Targeted heritable mutation and gene conversion by Cas9-CRISPR in Caenorhabditis elegans," Genetics, Nov. 2013, 195(3):1173-6.
Kearns et al., "Recombinant adeno-associated virus (AAV-CFTR) vectors do not integrate in a site-specific fashion in an immortalized epithelial cell line," Gene Ther., Sep. 1996, 9:748-55.
Keryer-Bibens et al., "Tethering of proteins to RNAs by bacteriophage proteins," Biol Cell, 2008, 100:125-138.
Khalil et al., "A Synthetic Biology Framework for Programming Eukaryotic Transcription Functions," Cell, Aug. 3, 2012, 150(3):647-58.
Kiani et al., "Cas9 gRNA engineering for genome editing, activation and repression," Nat. Methods, 2015, 12:1051-1054.
Kim and Kim, "A guide to genome engineering with programmable nucleases," Nature Rev Genetics 15, 321-334 (2014).
Kim et al., "Genome-wide analysis reveals specificities of Cpfl endonucleases in human cells", Nature Biotechnology, Aug. 2016, 34(8):863-868.
Kim et al., "Highly efficient RNA-guided genome editing in human cells via delivery of purified Cas9 ribonucleoproteins," Genome Res. Jun. 2014; 24(6):1012-9.
Kim et al., "Hybrid restriction enzymes: zinc finger fusions to Fok I cleavage domain," PNAS, Feb. 1996, 93:1156-1160.
Kim et al., "Targeted genome editing in human cells with zinc finger nucleases constructed via modular assembly," Genome Res., 19(7):1279-1288, Epub May 21, 2009.
Kim et al., "Genome editing with modularly assembled zinc-finger nucleases," Nat. Methods, 7(2):91-92, Feb. 2010.
Kleinstiver et al., "A unified genetic, computational and experimental framework identifies functionally relevant residues of the homing endonuclease I-BmoI," Nucleic Acids Res., 2010, 38:2411-2427.
Kleinstiver et al., "Broadening the targeting range of *Staphylococcus aureus* CRISPR-Cas9 by modifying PAM recognition," Nature Biotechnology, Dec. 2015, 33(12):1293-1298.
Kleinstiver et al., "Engineered CRISPR-Cas9 nucleases with altered PAM specificities," Nature, Jul. 2015, 523(7561):481-5.
Kleinstiver et al., "Genome-wide specificities of CRISPR-Cas Cpfl nucleases in human cells", Nature Biotechnology, Jun. 2016, 34(8):869-874.
Kleinstiver et al., "High-fidelity CRISPR-Cas9 nucleases with no detectable genome-wide offtarget effects," Nature, Jan. 2016, 529: 490-495.
Klimpel et al., "Anthrax toxin protective antigen is activated by a cell surface protease with the sequence specificity and catalytic properties of furin," PNAS, Nov. 1992, 89:10277-81.
Klug, "Co-chairman's remarks: protein designs for the specific recognition of DNA," Gene, 135(1-2):83-92, Dec. 15, 1993.
Koide et al. "The fibronectin type III domain as a scaffold for novel binding proteins," Journal of Molecular Biology, 1998, 284(4): 1141-1151.
Koike-Yusa et al., "Genome-wide recessive genetic screening in mammalian cells with a lentiviral CRISPR-guide RNA library," Nat Biotechnol., Mar. 2014, 32(3):267-73.
Kondo and Ueda, "Highly improved gene targeting by germline-specific Cas9 expression in *Drosophila*," Genetics, Nov. 2013, 195(3):715-21.
Konermann et al., "Optical control of mammalian endogenous transcription and epigenetic states," Nature. Aug. 22, 2013; 500(7463):472-6. (Author Manuscript).
KR Office Action in Korean Appln. No. 10-2015-7029170, dated Jan. 14, 2020, 12 pages (with English translation).
KR Office Action in KR Appln. No. 10-2015-7029171, dated Jan. 14, 2020, 16 pages (with English translation).
KR Office Action in KR Appln. No. 10-2015-7029177, dated Jan. 14, 2020, 6 pages (with English translation).
Kumar et al., "DNA-Prot: identification of DNA binding proteins from protein sequence information using random forest," J Biomol Struct Dyn., 2009, 26(6):679-686.
Kumar et al., "Identification of DNA-binding proteins using support vector machines and evolutionary profiles," BMC Bioinformatics, 8:463, Nov. 27, 2007.
Kummerfeld and Teichmann, "DBD: a transcription factor prediction database," Nucleic Acids Res., 34 (Database issue): D74-D81, Jan. 1, 2006.
Kurmasheva et al., "Upstream CpG island methylation of the PAX3 gene in human rhabdomyosarcomas," Pediatr. Blood Cancer, Apr. 2005, 44:328-37.
Lea et al., "Aberrant p16 methylation is a biomarker for tobacco exposure in cervical squamous cell carcinogenesis," Am. J. Obstet. Gynecol., 2004, 190:674-9.
Lee et al., "Three-dimensional solution structure of a single zinc finger DNA-binding domain," Science., 245(4918):635-637, Aug. 11, 1989.
Lehninger's Principles of Biochemistry, 5th edition, Ahr (ed.), 2008, Chapter 8.3, pp. 287 and 288.
Li et al., "DNA methylation in prostate cancer," Biochim. Biophys. Acta., Sep. 2004, 1704:87-102.
Li et al., "Heritable gene targeting in the mouse and rat using a CRISPR-Cas system," Nat Biotechnol, 2013, 31(8):681-3.
Li et al., "Identification of critical base pairs required for CTCF binding in motif M1 and M2," Protein & Cell, Mar. 2017, 8(7):544-549.
Li et al., "Modularly assembled designer TAL effector nucleases for targeted gene knockout and gene replacement in eukaryotes," Nucleic Acids Res., 39(14):6315-6325, Epub Mar. 31, 2011.
Li et al., "Protein trans-splicing as a means for viral vector-mediated in vivo gene therapy," Hum Gene Ther., 19(9):958-964, Sep. 2008.
Li et al., "Simultaneous generation and germline transmission of multiple gene mutations in rat using CRISPR-Cas systems," Nat Biotechnol., Aug. 2013, 31(8):684-6.
Li et al., "TAL nucleases (TALNs): hybrid proteins composed of TAL effectors and FokI DNA-cleavage domain," Nucleic Acids Res., 2011, 39(1): 359-372.
Lin et al., "A CRISPR Approach for Reactivating Latent HIV-1," Molecular Therapy, Mar. 2016, 24(3):416-418.
Lin et al., "CRISPR/Cas9 systems have off-target activity with insertions or deletions between target DNA and guide RNA sequences," Nucleic Acids Res., 2014, 42:7473-7485.

(56) References Cited

OTHER PUBLICATIONS

Lin et al., "iDNA-Prot: identification of DNA binding proteins using random forest with grey model," PLoS One., 2011, 6(9):e24756, 7 pages.
Lino et al, "Delivering CRISPR: a review of the challenges and approaches," Drug Delivery, 2018, 25:1234-1257.
Liu et al, "Delivery strategies of the CRISPR-Cas9 gene-editing system for therapeutic applications," Journal of Controlled Release, 2017, 266:17-26.
Liu et al., "Editing DNA Methylation in the Mammalian Genome," Cell, Sep. 2016, 167(1):233-247.
Liu et al., "Regulation of an Endogenous Locus Using a Panel of Designed Zinc Finger Proteins Targeted to Accessible Chromatin Regions," J. Biol. Chem., Apr. 2001, 276(14):11323-34.
Liu et al., "Validated zinc finger protein designs for all 16 GNN DNA triplet targets," J. Biol. Chem., 277(6):3850-3856, Epub Nov. 28, 2001.
Lo et al., "Precise and Heritable Genome Editing in Evolutionarily Diverse Nematodes Using TALENs and CRISPR/Cas9 to Engineer Insertions and Delections," Genetics, 2013, 195:331-348.
Lund et al., "DNA Methylation Polymorphisms Precede Any Histological Sign of Atherosclerosis in Mice Lacking Apolipoprotein E," J. Biol. Chem., Jul. 2004, 279:29147-54.
Ma et al., "A Guide RNA Sequence Design Platform for the CRISPR/Cas9 System for Model Organism Genomes," BioMed Research International, 2013, 2013: 270805, 4 pages.
Mabaera et al., "Developmental- and differentiation-specific patterns of human γ- and β-globin promoter DNA methylation," Blood, 110(4):1343-52 (2007).
Maeder et al., "CRISPR RNA-guided activation of endogenous human genes," Nat Methods, 2013, 10:977-979 (Author Manuscript).
Maeder et al., "Rapid 'open-source' engineering of customized zinc-finger nucleases for highly efficient gene modification," Mol Cell, 2008, 31(2):294-301.
Maeder et al., "Robust, synergistic regulation of human gene expression using TALE activators," Nat. Methods, 2013, 10:243-245.
Maeder et al., "Targeted DNA demethylation and activation of endogenous genes using programmable TALE-TET1 fusion proteins," Nat Biotechnol., 31(12):1137-1142, [author manuscript] Epub Oct. 9, 2013.
Mahfouz et al., "De novo-engineered transcription activator-like effector (TALE) hybrid nuclease with novel DNA binding specificity creates double-strand breaks," Proc Natl Acad Sci U S A, 108:2623-2628 (2011).
Maiti and Drohat, "Thymine DNA glycosylase can rapidly excise 5-formylcytosine and 5-carboxylcytosine: potential implications for active demethylation of CpG sites," J Biol Chem., 286(41):35334-35338, Epub Aug. 23, 2011.
Majumdar et al., "Targeted Gene Knock in and Sequence Modulation Mediated by a Psoralen-linked Triplex-forming Oligonucleotide," J Biol Chem., 283(17):11244-52 (2008).
Makarova et al., "A putative RNA-interference-based immune system in prokaryotes: computational analysis of the predicted enzymatic machinery, functional analogies with eukaryotic RNAi, and hypothetical mechanisms of action," Biol. Direct, 2006, 1:7, 26 pages.
Makarova et al., "Evolution and classification of the CRISPR-Cas systems," Nat. Rev. Microbiol., 2011, 9(6):467-77 (Author Manuscript).
Makarova et al., "Unification of Cas protein families and a simple scenario for the origin and evolution of CRISPR-Cas systems," Biol. Direct, 2011, 6:38, 27 pages.
Malech et al., "Prolonged production of NADPH oxidase-corrected granulocytes after gene therapy of chronic granulomatous disease," PNAS, Oct. 1997, 94:12133-38.
Mali et al., "Cas9 as a versatile tool for engineering biology," Nature Methods, 2013, 10(10):957-963.
Mali et al., "CAS9 transcriptional activators for target specificity screening and paired nickases for cooperative genome engineering," Nat Biotechnol., 2013, 31:833-838.
Mali et al., "RNA-guided human genome engineering via Cas9," Science, 2013, 339(6121):823-826, Supplemental Material, 38 pages.
Mali et al., "RNA-guided human genome engineering via Cas9," Science, Feb. 2013, 339:823-826.
Mancini et al. "CpG methylation within the 5' regulatory region of the BRCA1 gene is tumor specific and includes a putative CREB binding site," Oncogene, 1998, 16:1161-9.
Mandell and Barbas et al., "Zinc Finger Tools: custom DNA-binding domains for transcription factors and nucleases," Nucleic Acids Res., 34(Web Server issue): W516-W523, Jul. 1, 2006.
Marraffini and Sontheimer, "CRISPR Interference Limits Horizontal Gene Transfer in Staphylococci by Targeting DNA," Sci., 2008, 322(5909):1843-1845.
Marraffini and Sontheimer, "Self vs. non-self discrimination during CRISPR RNA-directed immunity," Nature, 2010, 463(7280):568-571 (Author Manuscript).
Mashiko et al., "Generation of mutant mice by pronuclear injection of circular plasmid expressing Cas9 and single guided RNA," Sci Reports, 2013, 3(3355):1-6.
McGarty, "CRISPRs and Cancer," White Paper No. 111, Apr. 2014, 22 pages.
Melo et al., "eRNAs Are Required for p53-Dependent Enhancer Activity and Gene Transcription," Mol Cell, Feb. 2013, 49:524-535.
Mendenhall et al., "Locus-specific editing of histone modifications at endogenous enhancers," Nat Biotechnol., 31(12):1133-1136, Epub Sep. 8, 2013.
Miller et al., "A TALE nuclease architecture for efficient genome editing," Nat Biotechnol., Feb. 2011, 29:143-148.
Miller et al., "An improved zinc-finger nuclease architecture for highly specific genome editing," Nat Biotechnol., 2007, 25:778-785.
Miller et al., "Repetitive zinc-binding domains in the protein transcription factor IIIA from Xenopus oocytes," EMBO J., 4(6):1609-1614, Jun. 1985.
Mino et al., "Efficient double-strand DNA cleavage by artificial zinc-finger nucleases composed of one zinc-finger protein and a single-chain FokI dimer," J Biotechnol., 2009, 140:156-161.
Miyazaki et al., "Expression vector system based on the chicken beta-actin promoter directs efficient production of interleukin-5," Gene, Jul. 1989, 79(2):269-77.
Mojica et al., "Biological significance of a family of regularly spaced repeats in the genomes of Archaea, Bacteria and mitochondria," Mol Microbiol., Apr. 2000, 36(1):244-6.
Mojica et al., "Short motif sequences determine the targets of the prokaryotic CRISPR defense system," Microbiology, 2009, 155:733-740.
Moore et al., "Design of polyzinc finger peptides with structured linkers," Proc Natl Acad Sci USA, Feb. 2001, 98:1432-1436.
Morbitzer et al., "Regulation of selected genome loci using de novo-engineered transcription activator-like effector (TALE)-type transcription factors," Proc Natl Acad Sci USA, 2010, 107(50):21617-21622.
Morbitzer et al., "Assembly of custom TALE-type DNA binding domains by modular cloning," Nucl Acids Res., 2011, 39:5790-5799.
Morita et al., "Targeted DNA demethylation in vivo using dCas9-peptide repeat and scFv-TET1 catalytic domain fusions," Nature Biotechnology, Oct. 2016, 34(10):1060-1065.
Morrison, "Transformation in *Escherichia coli*: Cryogenic Preservation of Competent Cells," J. Bacteriol., Oct. 1977, 132:349-351.
Moscou and Bogdanove, "A simple cipher governs DNA recognition by TAL effectors," Science, 326(5959):1501, Dec. 11, 2009.
Mussolino and Cathomen, "RNA guides genome engineering," Nat Biotechnol., 2013, 31(3):208-209.
Mussolino et al., "A novel TALE nuclease scaffold enables high genome editing activity in combination with low toxicity," Nucleic Acids Res., 2011, 39:9283-93.
Muthuswamy et al., "Controlled Dimerization of ErbB Receptors Provides Evidence for Differential Signaling by Homo- and Heterodimers," Mol. Cell. Biol., Oct. 1999, 19(10):6845-6857.

(56) References Cited

OTHER PUBLICATIONS

Needleman and Wunsch, "A General Method Applicable to the Search for Similarities in the Amino Acid Sequence of Two Proteins," J. Mol. Biol., 1970, 48:444-453.
Neering et al., "Transduction of Primitive Human Hematopoietic Cells With Recombinant Adenovirus Vectors," Blood, Aug. 1996, 88:1147-55.
Nielsen et al., "Interaction with members of the heterochromatin protein 1 (HP1) family and histone deacetylation are differentially involved in transcriptional silencing by members of the TIFI family," EMBO J., 1999, 18:6385-6395.
Nishimasu et al. "Crystal Structure of Cas9 in Complex with Guide RNA and Target DNA," Cell, 2014, 156, 935-949.
Nissim et al., "Multiplexed and Programmable Regulation of Gene Networks with an Integrated RNA and CRISPR/Cas Toolkit in Human Cells," Molecular Cell, May 2014, 54:698-710.
Niu et al., "Generation of gene-modified cynomolgus monkey via Cas9/RNA-mediated gene targeting in one-cell embryos," Cell, 2014, 156:836-843.
Niwa et al., "Efficient selection for high-expression transfectants with a novel eukaryotic vector," Gene, 1991, 108(2):193-9.
Nord et al. "Binding proteins selected from combinatorial libraries of an α-helical bacterial receptor domain," Nature Biotechnology, 1997, 15(8): 772-777.
Novak et al., "Functional Characterization of Protease-treated Bacillus anthracis Protective Antigen," J. Biol. Chem., Aug. 1992, 267:17186-93.
Office Action in European Application No. 14764117.9, dated Jul. 6, 2017, 4 pages.
Office Action in European Application No. 14764117.9, dated Oct. 5, 2018, 6 pages.
Office Action in U.S. Appl. No. 14/211,117, dated Jan. 9, 2017, 12 pages.
Office Action in U.S. Appl. No. 14/211,117, dated Nov. 3, 2017, 11 pages.
Office Action in U.S. Appl. No. 14/211,117, dated Sep. 8, 2015, 20 pages.
Office Action in U.S. Appl. No. 14/775,869, dated Sep. 11, 2017, 43 pages.
Office Action in U.S. Appl. No. 14/775,930, dated Feb. 27, 2017, 55 pages.
Office Action in U.S. Appl. No. 14/775,930, dated Sep. 21, 2017, 23 pages.
Office Action in U.S. Appl. No. 14/776,620, dated Mar. 31, 2017.
Office Action in U.S. Appl. No. 14/776,620, dated Sep. 28, 2017, 8 pages.
Office Action in U.S. Appl. No. 15/107,550, dated Mar. 9, 2018, 21 pages.
Oligino et al., "Drug inducible transgene expression in brain using a herpes simplex virus vector," Gene Ther., 1998, 5:491-496.
Palva et al., "Secretion of interferon by Bacillus subtilis," Gene, 1983, 22:229-235.
Partial Supplementary Search Report in European Application No. 16842722.7, dated Mar. 7, 2019, 13 pages.
Pattanayak et al., "High-throughput profiling of off-target DNA cleavage reveals RNA-programmed Cas9 nuclease specificity," Nat Biotechnol., 2013, 31:839-843 (Author Manuscript).
Pattanayak et al., "Revealing off-target cleavage specificities of zinc-finger nucleases by in vitro selection," Nat Methods, 2011, 8:765-770 (Author Manuscript).
Pavletich and Pabo, "Zinc finger-DNA recognition: crystal structure of a Zif268-DNA complex at 2.1 A," Science, 252(5007):809-817, May 10, 1991.
PCT International Preliminary Report on Patentability in International Application No. PCT/US2014/029068, mailed Sep. 15, 2015, 10 pages.
PCT International Preliminary Report on Patentability in International Application No. PCT/US2014/029304, mailed Sep. 22, 2015, 12 pages.
PCT International Preliminary Report on Patentability in International Appln. No. PCT/US2014/027335, dated Sep. 24, 2015, 9 pages.
PCT International Preliminary Report on Patentability in International Appln. No. PCT/US2017/056738, dated Apr. 16, 2019, 10 pages.
PCT International Search Report and Written Opinion in International Application No. PCT/US2013/074736, mailed on Sep. 17, 2014, 4 pages.
PCT International Search Report and Written Opinion in International Appln. No. PCT/US2014/027335, dated Jul. 16, 2014, 13 pages.
PCT International Search Report and Written Opinion in International Appln. No. PCT/US2017/056738, dated Apr. 19, 2018, 15 pages.
PCT International Search Report and Written Opinion in International Appln. No. PCT/US2018/028898, dated Jul. 23, 2018, 12 pages.
PCT International Search Report and Written Opinion in International Appln. No. PCT/US2019/032937, dated Oct. 17, 2019, 17 pages.
PCT International Search Report and Written Opinion in International Appln. No. PCT/US2020/062166, dated May 4, 2021, 13 pages.
Perelle et al., "Characterization of Clostridium perfringens Iota-Toxin Genes and Expression in *Eschenichia coli*," Infect. Immun., Dec. 1993, 61:5147-56.
Perez et al., "Establishment of HIV-1 resistance in CD4+ T cells by genome editing using zinc-finger nucleases," Nat Biotechnol., 2008, 26:808-816.
Perez-Pinera et al., "RNA-guided gene activation by CRISPR-Case9-based transcription factors," Nat Methods, 2013, 10(10):973-976 (Author Manuscript).
Pingoud and Silva, "Precision genome surgery," Nat Biotechnol., 25(7):743-744, Jul. 2007.
Puchta and Fauser et al., "Synthetic nucleases for genome engineering in plants: prospects for a bright future," Plant J. Jun. 2014; 78(5):727-41.
Qi et al., "Repurposing CRISPR as an RNA-Guided Platform for Sequence-Specific Control of Gene Expression," Cell, Feb. 2013, 152:1173-1183.
Ramakrishna et al., "Gene disruption by cell-penetrating peptide-mediated delivery of Cas9 protein and guide RNA," Genome Res. Jun. 2014; 24(6): 1020-1027.
Ramakrishna et al., "Surrogate reporter-based enrichment of cells containing RNA-guided Cas9 nuclease-induced mutations," Nat Commun. Feb. 26, 2014; 5:3378.
Ramalingam et al., "A CRISPR way to engineer the human genome," Genome Biol., 2013, 14:107, 4 pages.
Ramirez et al., "Unexpected failure rates for modular assembly of engineered zinc fingers," Nat Methods., 5(5):374-375, May 2008.
Ran et al., "Double nicking by RNA-guided CRISPR Cas9 for enhanced genome editing specificity," Cell, 2013, 154:1380-1389.
Ran et al., "Genome engineering using the CRISPR-Cas9 system," Nature Protocols, 2013, 8(11):2281-2308.
Ran et al., "In vivo genome editing using *Staphylococcus aureus* Cas9," Nature, 2015, 520:186-191.
Rebar et al., "Zinc finger phage: affinity selection of fingers with new DNA-binding specificities," Science, 1994 263(5147):671-673.
Ren et al., "Optimized gene editing technology for *Drosophila melanogaster* using germ line-specific Cas9," Proc Natl Acad Sci U S A, Nov. 19, 2013, 110(47):19012-7.
Rendahl et al., "Regulation of gene expression in vivo following transduction by two separate rAAV vectors," Nat. Biotechnol., Aug. 1998, 16:757-761.
Reyon et al., "FLASH assembly of TALENs for high-throughput genome editing," Nat Biotech, 2012, 30:460-465 (Author Manuscript).
Ro et al., "Adenovirus-based short hairpin RNA vectors containing an EGFP marker and mouse U6, human H1, or human U6 promoter," BioTechniques, 2005, 38(4):625-627.

(56) References Cited

OTHER PUBLICATIONS

Rodenhiser and Mann, "Epigenetics and human disease: translating basic biology into clinical applications," CMAJ, 174(3):341-348 (2006).
Rohde et al., "BISMA—Fast and accurate bisulfite sequencing data analysis of individual clones from unique and repetitive sequences," BMC Bioinformatics, 11:230 12 pages (2010).
Rojano et al., "Regulatory variants: from detection to predicting impact," Briefings in Bioinformatics, Sep. 2019, 20(5):1639-1654.
Rothman, "Mechanisms of intracellular protein transport," Nature, 372(6501):55-63, Nov. 3, 1994.
Rusk, "CRISPRs and epigenome editing," Nature Methods, 2014, 11(1):28.
Sander and Joung et al., "CRISPR-Cas systems for editing, regulating and targeting genomes," Nat Biotechnol., Apr. 2014, 32(4):347-55.
Sander et al., "In silico abstraction of zinc finger nuclease cleavage profiles reveals an expanded landscape of off-target sites," Nucleic Acids Res., 2013, 41:e181.
Sander et al., "ZiFiT (Zinc Finger Targeter): an updated zinc finger engineering tool," Nucleic Acids Res., 2010, 38:W462-468.
Sander et al., "Zinc Finger Targeter (ZiFiT): an engineered zinc finger/target site design tool," Nucleic Acids Res., 2007, 35:W599-605.
Sander et al., "Targeted gene disruption in somatic zebrafish cells using engineered TALENs," Nat. Biotechnol., 29:697-698 (2011).
Sanjana et al., "A transcription activator-like effector toolbox for genome engineering," Nature Protocols, 2012, 7:171-192.
Sapranauskas et al., "The *Streptococcus thermophilus* CRISPR/Cas system provides immunity in *Escherichia coli*," Nucleic Acids Res., 2011, 39(21):9275-9282.
Schleifman et al., "Triplex-mediated gene modification," Methods Mol. Biol., 435:175-190, 2008.
Scholze & Boch, "TAL effectors are remote controls for gene activation," J. Curr. Opin. Microbiol, 14:47-53 (2011).
Schwank et al., "Functional repair of CFTR by CRISPR/Cas9 in intestinal stem cell organoids of cystic fibrosis patients," Cell Stem Cell, Dec. 5, 2013, 13(6):653-8.
Sebo et al., "Cell-invasive activity of epitope-tagged adenylate cyclase of Bordetella pertussis allows in vitro presentation of a foreign epitope to CD8+ cytotoxic T cells," Infect. Immun., Oct. 1995, 63:3851-57.
Segal et al., "Evaluation of a modular strategy for the construction of novel polydactyl zinc finger DNA-binding proteins," Biochemistry, 42(7):2137-2148, Feb. 25, 2003.
Sequence Alignment of SEQ ID No. 1 of U.S. Appl. No. 15/107,550 with SEQ ID No. 103 of US2013/0130248A1. Search conducted on Feb. 15, 2018, 1 page as part of Office Action in U.S. Appl. No. 15/107,550.
Shah et al., "Protospacer recognition motifs," RNA Biol., 2013, 10:891-899.
Sharma, "Schizophrenia, epigenetics and ligand-activated nuclear receptors: a framework for chromatin therapeutics," Schizophr. Res., Jan. 2005, 72:79-90.
Shen et al., "Efficient genome modification by CRISPR-Cas9 nickase with minimal off-target effects," Nat Methods, 2014, 11(4):399-402.
Shen et al., "Generation of gene-modified mice via Cas9/RNA-mediated gene targeting," Cell Res., 2013, 23(5):720-3.
Shmakov et al., "Discovery and Functional Characterization of Diverse Class 2 CRISPR-Cas Systems," Molecular Cell, 2015 60:385-397.
Silva et al., "Meganucleases and other tools for targeted genome engineering: perspectives and challenges for gene therapy," Curr Gene Ther., 11(1):11-27, Feb. 2011.
Silver, "How Proteins Enter the Nucleus," Cell, 64(3):489-497, Feb. 8, 1991.
Simon et al., "Sequence-specific DNA cleavage mediated by bipyridine polyamide conjugates," Nucl. Acids Res., 36(11):3531-8 (2008).
Slaymaker et al. 2016; Rationally engineered Cas9 nucleases with improved specificity. Science 351(6268): 84-88.
Stenmark et al., "Peptides fused to the amino-terminal end of diphtheria toxin are translocated to the cytosol," J. Cell Biol., Jun. 1991, 113:1025-32.
Sterman et al., "Adenovirus-mediated herpes simplex virus thymidine kinase/ganciclovir gene therapy in patients with localized malignancy: results of a phase I clinical trial in malignant mesothelioma," Hum. Gene Ther., May 1998, 7:1083-89.
Sternberg et al., "Conformational control of DNA target cleavage by CRISPR-Cas9" Nature, 2015, 527:110-113.
Sternberg et al., "DNA interrogation by the CRISPR RNA-guided endonuclease Cas9," Nature, 2014, 507:62-67.
Sternberg et al., "Mechanism of substrate selection by a highly specific CRISPR endoribonuclease," RNA, 2012, 18:661-672.
Stoddard, "Homing endonuclease structure and function," Q. Rev. Biophys., 38(1): 49-95, Epub Dec. 9, 2005.
Storrs, "A CRISPR Fore-Cas-t: A newcomer's guide to the hottest gene-editing tool on the block," Scientist Magazine, Mar. 2014, 4 pages.
Sugimoto et al., "Thermodynamic parameters to predict stability of RNA/DNA hybrid duplexes," Biochemistry, 1995, 34:11211-11216.
Sugimoto et al., "Thermodynamics-structure relationship of single mismatches in RNA/DNA duplexes," Biochemistry, Sep. 19, 2000, 39(37):11270-81.
Swarts el al., "CRISPR Interference Directed Strand Specific Spacer Acquisition," PLOS, 2012, 7(4):1-7.
Szczepek et al., "Structure-based redesign of the dimerization interface reduces the toxicity of zinc-finger nucleases," Nat Biotechnol., 2007, 25:786-793.
Szyf et al., "DNA methylation and breast cancer," Biochem. Pharmacol., Sep. 2004, 68:1187-97.
Tahiliani et al., "Conversion of 5-Methylcytosine to 5-Hydroxymethylcytosine in Mammalian DNA by MLL Partner TET1," Science, 324:930-935 (2009).
Tan et al., "Efficient nonmeiotic allele introgression in livestock using custom endonucleases," Proc Natl Acad Sci USA, 2013, 110(41):16526-31.
Tan et al., "Zinc-finger protein-targeted gene regulation: genomewide single-gene specificity," Proc Natl Acad Sci U S A., 100(21):11997-2002, Epub Sep. 26, 2003.
Terns and Terns, "CRISPR-based adaptive immune systems," Curr Opin Microbiol., 2011, 14:321-327.
Tesson et al., "Knockout rats generated by embryo microinjection of TALENs," Nat. Biotechnol., 29:695-696 (2011).
Tjong and Zhou, "DISPLAR: an accurate method for predicting DNA-binding sites on protein surfaces," Nucleic Acids Res., 35(5):1465-1477, Epub Feb. 6, 2007.
Tsai et al., "Dimeric CRISPR RNA-guided FokI nucleases for highly specific genome editing," Nat Biotechnol., Apr. 2014, 32(6):569-576.
Tsai et al., "GUIDE-Seq enables genome-wide profiling of off-target cleavage by CRISPR-Cas nucleases," Nat Biotechnol, Feb. 2015, 33:187-197.
Tzur et al., "Heritable Custom Genomic Modifications in Caenorhabditis elegans via a CRISPR-Cas9 System," Genetics, 2013, 195:1181-1185.
Uhlmann et al., "Distinct methylation profiles of glioma subtypes," Int. J. Cancer, Aug. 2003, 106:52-9.
Ui-Tei et al., "Functional dissection of siRNA sequence by systematic DNA substitution: modified siRNA with a DNA seed arm is a powerful tool for mammalian gene silencing with significantly reduced off-target effect," Nucleic Acids Research, 2008, 36: 2136-2151.
US Final Office Action in U.S. Appl. No. 13/838,520, dated Jul. 15, 2015, 35 pages.
US Final Office Action in U.S. Appl. No. 14/211,117, dated Jun. 30, 2016, 26 pages.
US Non-Final Office Action in U.S. Appl. No. 14/211,117, dated Sep. 8, 2015, 20 pages.
US Non-Final Office Action in U.S. Appl. No. 14/213,479, dated Dec. 9, 2015, 39 pages.
US Non-Final Office Action in U.S. Appl. No. 14/213,723, dated Mar. 2, 2016, 39 pages.

(56) References Cited

OTHER PUBLICATIONS

US Non-Final Office Action in U.S. Appl. No. 13/838,520, dated Oct. 6, 2014, 38 pages.
Van der Oost et al., "Unravelling the Structural and Mechanistic Basis of CRISPR-Cas Systems," Nature Reviews Microbiology, 2014, 12:479-492.
Ventura et al., "Cre-lox-regulated conditional RNA interference from transgenes," PNAS, Jul. 2004, 101:10380-10385.
Waaijers et al., "CRISPR/Cas9-Targeted Mutagenesis in Caenorhabditis elegans," Genetics, 2013, 195:1187-1191.
Wagner et al., "Efficient and persistent gene transfer of AAV-CFTR in maxillary sinus," Lancet, Jun. 1998, 351:1702-1703.
Wang et al., "One-Step Generation of Mice Carrying Mutations in Multiple Genes by CRISPR/Cas-Mediated Genome Engineering," Cell, 2013, 153:910-918.
Wang et al., "Positive and negative regulation of gene expression in eukaryotic cells with an inducible transcriptional regulator," Gene Ther., May 1997, 4:432-441.
Wang et al., "The CRISPR/Cas system mediates efficient genome engineering in Bombyx mori," Cell Res., Dec. 2013, 23(12):1414-6.
Weber et al., "Assembly of Designer TAL Effectors by Golden Gate Cloning," PLoS ONE, 6:e19722 (2011).
Widschwendter and Jones, "DNA methylation and breast carcinogenesis," Oncogene, Aug. 2002, 21:5462-82.
Wiedenheft et al., "RNA-guided genetic silencing systems in bacteria and archaea," Nature, 2012, 482:331-338.
Williams et al., "Tet1 and hydroxymethylcytosine in transcription and DNA methylation fidelity," Nature, May 2011, 473:343-349.
Wolfe et al., "DNA recognition by Cys2His2 zinc finger proteins," Annu Rev Biophys Biomol Struct. 29:183-212 (2000).
Wong et al., "Detection of aberrant p16 methylation in the plasma and serum of liver cancer patients," Cancer Res., 59(1):71-73 Jan. 1, 1999.
Wood et al., "Targeted Genome Editing Across Species Using ZFNs and TALENs," Science, 333:307 (2011).
Wright et al., "Standardized reagents and protocols for engineering zinc finger nucleases by modular assembly," Nat Protoc., 2006, 1(3):1637-1652.
Wu et al., "Building zinc fingers by selection: toward a therapeutic application," Proc Natl Acad Sci U S A., 92(2):344-348, Jan. 17, 1995.
Wu et al., "Correction of a genetic disease in mouse via use of CRISPR-Cas9," Cell Stem Cell, 2013, 13(6):659-62.
Wu et al., "Custom-designed zinc finger nucleases: what is next?" Cell Mol Life Sci., 64(22):2933-2944, Nov. 2007.
Wu et al., "Genome-wide binding of the CRISPR endonuclease Cas9 in mammalian cells," Nat Biotechnol. Jul. 2014; 32(7):670-6.
Xu et al., "Optimization of transcriptional regulatory elements for constructing plasmid vectors," Gene. Jul. 2001, 272(1-2):149-56.
Xu et al., "Genome-wide regulation of 5hmC, 5mC, and gene expression by Tet1 hydroxylase in mouse embryonic stem cells," Mol Cell., 42(4):451-464, Epub Apr. 21, 2011.
Yang et al., "One-step generation of mice carrying reporter and conditional alleles by CRISPR/Cas-mediated genome engineering," Cell, Sep. 12, 2013; 154(6):1370-9.
Yang et al., "Optimization of scarless human stem cell genome editing," Nucleic Acids Res., 2013, 41:9049-9061.
Yin et al., "Genome editing with Cas9 in adult mice corrects a disease mutation and phenotype," Nature Biotechnology 32, 551-553 (2014).
Yin et al., "Partial DNA-guided Cas9 enables genome editing with reduced off-target activity," Nature Chemical Biology, Mar. 2018, 14(3)311-316.
Zetsche et al., "Cpf1 Is a Single RNA-Guided Endonuclease of a Class 2 CRISPR-Cas System," Cell, 2015, 163:759-771.
Zhang et al., "Efficient construction of sequence-specific TAL effectors for modulating mammalian transcription," Nat Biotechnol., 29(2):149-153, Epub Jan. 19, 2011.
Zhang et al., "TET1 is a DNA-binding protein that modulates DNA methylation and gene transcription via hydroxylation of 5-methylcytosine," Cell Res., 2010, 20(12):1390-1393.
Zhou et al., "High-throughput screening of a CRISPR/Cas9 library for functional genomics in human cells," Nature. May 22, 2014; 509(7501):487-91.
Zitzewitz et al., "Probing the folding mechanism of a leucine zipper peptide by stopped-flA4:A48ism spectroscopy," Biochemistry, 34(39):12812-12819, Oct. 3, 1995.
Office Action in Japanese Appln. No. 2021-138479, dated Aug. 30, 2022, 23 pages (with English translation).
Eguchi et al., "Controlling gene networks and cell fate with precision-targeted DNA-binding proteins and small-molecule-based genome readers," The Biochemical Journal, Sep. 2014, 432(3):397-413.
Li et al., "Ankyrin Repeat: A unique motif mediating protein-protein interactions," Biochemistry, Dec. 2006, 45(51):15168-15178.
Office Action in Japanese Appln. No. 2021-138479, dated Apr. 18, 2023, 11 pages (with English translation).
Office Action in Canadian Appln. No. 3,161,835, dated Jun. 5, 2023, 3 pages.
Office Action in Japanese Appln. No. 2023-011473, dated Feb. 6, 2024, 21 pages (with English translation).
Fu et al., "Supplemental Information: Improving CRISPR-Cas nuclease specificity using truncated guide RNAs," Nat. Biotechnol. Mar. 2014, 22 pages.
Molecular Biology (Chinese Edition), 1st ed., Yu et al. (eds.), Jul. 2007, pp. 100-105, 17 pages (with English translation).
Office Action in Chinese Appln. No. 202110709688.0, dated Aug. 10, 2023, 17 pages (with English translation).

FIG. 4

| Guide RNA expression vector sequence |
| --- |
| GACGTCGCTAGCTGTACAAAAAAGCAGGCTTTAAAGGAACCAATTCAGTCGACTGGATCCGGTACCAAGG<br>TCGGGCAGGAAGAGGGCCTATTTCCCATGATTCCTTCATATTTGCATATACGATACAAGGCTGTTAGAGA<br>GATAATTAGAATTAATTTGACTGTAAACACAAAGATATTAGTACAAAATACGTGACGTAGAAAGTAATAA<br>TTTCTTGGGTAGTTTGCAGTTTTAAAATTATGTTTTAAAATGGACTATCATATGCTTACCGTAACTTGAA<br>AGTATTTCGATTTCTTGGCTTTATATATCTTGTGGAAAGGACGAAACACCNNNNNNNNNNNNNNNNNNNN<br>GTTTTAGAGCTAGAAATAGCAAGTTAAAATAAGGCTAGTCCGTTATCAACTTGAAAAAGTGGCACCGAGT<br>CGGTGCTTTTTTTAAGCTTGGGCCGCTCGAGGTACCTCTCTACATATGACATGTGAGCAAAAGGCCAGCA<br>AAAGGCCAGGAACCGTAAAAAGGCCGCGTTGCTGGCGTTTTTCCATAGGCTCCGCCCCCCTGACGAGCAT<br>CACAAAAATCGACGCTCAAGTCAGAGGTGGCGAAACCCGACAGGACTATAAAGATACCAGGCGTTTCCCC<br>CTGGAAGCTCCCTCGTGCGCTCTCCTGTTCCGACCCTGCCGCTTACCGGATACCTGTCCGCCTTTCTCCC<br>TTCGGGAAGCGTGGCGCTTTCTCATAGCTCACGCTGTAGGTATCTCAGTTCGGTGTAGGTCGTTCGCTCC<br>AAGCTGGGCTGTGTGCACGAACCCCCCGTTCAGCCCGACCGCTGCGCCTTATCCGGTAACTATCGTCTTG<br>AGTCCAACCCGGTAAGACACGACTTATCGCCACTGGCAGCAGCCACTGGTAACAGGATTAGCAGAGCGAG<br>GTATGTAGGCGGTGCTACAGAGTTCTTGAAGTGGTGGCCTAACTACGGCTACACTAGAAGAACAGTATTT<br>GGTATCTGCGCTCTGCTGAAGCCAGTTACCTTCGGAAAAAGAGTTGGTAGCTCTTGATCCGGCAAACAAA<br>CCACCGCTGGTAGCGGTGGTTTTTTTGTTTGCAAGCAGCAGATTACGCGCAGAAAAAAAGGATCTCAAGA<br>AGATCCTTTGATCTTTTCTACGGGGTCTGACGCTCAGTGGAACGAAAACTCACGTTAAGGGATTTTGGTC<br>ATGAGATTATCAAAAAGGATCTTCACCTAGATCCTTTTAAATTAAAAATGAAGTTTTAAATCAATCTAAA<br>GTATATATGAGTAAACTTGGTCTGACAGTTACCAATGCTTAATCAGTGAGGCACCTATCTCAGCGATCTG<br>TCTATTTCGTTCATCCATAGTTGCCTGACTCCCCGTCGTGTAGATAACTACGATACGGGAGGGCTTACCA<br>TCTGGCCCCAGTGCTGCAATGATACCGCGAGACCCACGCTCACCGGCTCCAGATTTATCAGCAATAAACC<br>AGCCAGCCGGAAGGGCCGAGCGCAGAAGTGGTCCTGCAACTTTATCCGCCTCCATCCAGTCTATTAATTG<br>TTGCCGGGAAGCTAGAGTAAGTAGTTCGCCAGTTAATAGTTTGCGCAACGTTGTTGCCATTGCTACAGGC<br>ATCGTGGTGTCACGCTCGTCGTTTGGTATGGCTTCATTCAGCTCCGGTTCCCAACGATCAAGGCGAGTTA<br>CATGATCCCCCATGTTGTGCAAAAAAGCGGTTAGCTCCTTCGGTCCTCCGATCGTTGTCAGAAGTAAGTT<br>GGCCGCAGTGTTATCACTCATGGTTATGGCAGCACTGCATAATTCTCTTACTGTCATGCCATCCGTAAGA<br>TGCTTTTCTGTGACTGGTGAGTACTCAACCAAGTCATTCTGAGAATAGTGTATGCGGCGACCGAGTTGCT<br>CTTGCCCGGCGTCAATACGGGATAATACCGCGCCACATAGCAGAACTTTAAAAGTGCTCATCATTGGAAA<br>ACGTTCTTCGGGGCGAAAACTCTCAAGGATCTTACCGCTGTTGAGATCCAGTTCGATGTAACCCACTCGT<br>GCACCCAACTGATCTTCAGCATCTTTTACTTTCACCAGCGTTTCTGGGTGAGCAAAAACAGGAAGGCAAA<br>ATGCCGCAAAAAAGGGAATAAGGGCGACACGGAAATGTTGAATACTCATACTCTTCCTTTTTCAATATTA<br>TTGAAGCATTTATCAGGGTTATTGTCTCATGAGCGGATACATATTTGAATGTATTTAGAAAAATAAACAA<br>ATAGGGGTTCCGCGCACATTTCCCCGAAAAGTGCCACCT (SEQ ID NO:107) |

FIG. 5

| CMV-T7-Cas9 D10A/H840A-3XFLAG-VP64: |
| --- |
| ATATGCCAAGTACGCCCCCTATTGACGTCAATGACGGTAAATGGCCCGCCTGGCATTATGCCCAGTACATGACCTT<br>ATGGGACTTTCCTACTTGGCAGTACATCTACGTATTAGTCATCGCTATTACCATGGTGATGCGGTTTTGGCAGTACA<br>TCAATGGGCGTGGATAGCGGTTTGACTCACGGGGATTTCCAAGTCTCCACCCCATTGACGTCAATGGGAGTTTGTT<br>TTGGCACCAAAATCAACGGGACTTTCCAAAATGTCGTAACAACTCCGCCCCATTGACGCAAATGGGCGGTAGGCG<br>TGTACGGTGGGAGGTCTATATAAGCAGAGCTGGTTTAGTGAACCGTCAGATCCGCTAGAGATCCGCGGCCGCTAA<br>TACGACTCACTATAGGGAGAGCCGCCACCATGGATAAGAAATACTCAATAGGCTTAGcTATCGGCACAAATAGCG<br>TCGGATGGGCGGTGATCACTGATGAATATAAGGTTCCGTCTAAAAAGTTCAAGGTTCTGGGAAATACAGACCGCC<br>ACAGTATCAAAAAAAATCTTATAGGGGCTCTTTTATTTGACAGTGGAGAGACAGCGGAAGCGACTCGTCTCAAAC<br>GGACAGCTCGTAGAAGGTATACACGTCGGAAGAATCGTATTTGTTATCTACAGGAGATTTTTTCAAATGAGATGGC<br>GAAAGTAGATGATAGTTTCTTTCATCGACTTGAAGAGTCTTTTTTGGTGGAAGAAGACAAGAAGCATGAACGTCAT<br>CCTATTTTTGGAAATATAGTAGATGAAGTTGCTTATCATGAGAAATATCCAACTATCTATCATCTGCGAAAAAAATT<br>GGTAGATTCTACTGATAAAGCGGATTTGCGCTTAATCTATTTGGCCTTAGCGCATATGATTAAGTTTCGTGGTCATT<br>TTTTGATTGAGGGAGATTTAAATCCTGATAATAGTGATGTGGACAAACTATTTATCCAGTTGGTACAAACCTACAAT<br>CAATTATTTGAAGAAAACCCTATTAACGCAAGTGGAGTAGATGCTAAAGCGATTCTTTCTGCACGATTGAGTAAAT<br>CAAGACGATTAGAAAATCTCATTGCTCAGCTCCCCGGTGAGAAGAAAAATGGCTTATTTGGGAATCTCATTGCTTT<br>GTCATTGGGTTTGACCCCTAATTTTAAATCAAATTTTGATTTGGCAGAAGATGCTAAATTACAGCTTTCAAAAGATA<br>CTTACGATGATGATTTAGATAATTTATTGGCGCAAATTGGAGATCAATATGCTGATTTGTTTTTGGCAGCTAAGAAT<br>TTATCAGATGCTATTTTACTTTCAGATATCCTAAGAGTAAATACTGAAATAACTAAGGCTCCCCTATCAGCTTCAAT<br>GATTAAACGCTACGATGAACATCATCAAGACTTGACTCTTTTAAAAGCTTTAGTTCGACAACAACTTCCAGAAAAGT<br>ATAAAGAAATCTTTTTTGATCAATCAAAAAACGGATATGCAGGTTATATTGATGGGGGAGCTAGCCAAGAAGAAT<br>TTTATAAATTTATCAAACCAATTTTAGAAAAAATGGATGGTACTGAGGAATTATTGGTGAAACTAAATCGTGAAGA<br>TTTGCTGCGCAAGCAACGGACCTTTGACAACGGCTCTATTCCCCATCAAATTCACTTGGGTGAGCTGCATGCTATTT<br>TGAGAAGACAAGAAGACTTTTATCCATTTTTAAAAGACAATCGTGAGAAGATTGAAAAAATCTTGACTTTTCGAAT<br>TCCTTATTATGTTGGTCCATTGGCGCGTGGCAATAGTCGTTTTGCATGGATGACTCGGAAGTCTGAAGAAACAATT<br>ACCCCATGGAATTTTGAAGAAGTTGTCGATAAAGGTGCTTCAGCTCAATCATTTATTGAACGCATGACAAACTTTG<br>ATAAAAATCTTCCAAATGAAAAAGTACTACCAAAACATAGTTTGCTTTATGAGTATTTTACGGTTTATAACGAATTG<br>ACAAAGGTCAAATATGTTACTGAAGGAATGCGAAAACCAGCATTTCTTTCAGGTGAACAGAAGAAAGCCATTGTT<br>GATTTACTCTTCAAAACAAATCGAAAAGTAACCGTTAAGCAATTAAAAGAAGATTATTTCAAAAAAATAGAATGTT<br>TTGATAGTGTTGAAATTTCAGGAGTTGAAGATAGATTTAATGCTTCATTAGGTACCTACCATGATTTGCTAAAAATT<br>ATTAAAGATAAAGATTTTTTGGATAATGAAGAAAATGAAGATATCTTAGAGGATATTGTTTTAACATTGACCTTATT<br>TGAAGATAGGGAGATGATTGAGGAAAGACTTAAAACATATGCTCACCTCTTTGATGATAAGGTGATGAAACAGCT<br>TAAACGTCGCCGTTATACTGGTTGGGGACGTTTGTCTCGAAAATTGATTAATGGTATTAGGGATAAGCAATCTGGC<br>AAAACAATATTAGATTTTTTGAAATCAGATGGTTTTGCCAATCGCAATTTTATGCAGCTGATCCATGATGATAGTTT<br>GACATTTAAAGAAGACATTCAAAAAGCACAAGTGTCTGGACAAGGCGATAGTTTACATGAACATATTGCAAATTTA<br>GCTGGTAGCCCTGCTATTAAAAAAGGTATTTTACAGACTGTAAAAGTTGTTGATGAATTGGTCAAAGTAATGGGGC<br>GGCATAAGCCAGAAAATATCGTTATTGAAATGGCACGTGAAAATCAGACAACTCAAAAGGGCCAGAAAAATTCGC<br>GAGAGCGTATGAAACGAATCGAAGAAGGTATCAAAGAATTAGGAAGTCAGATTCTTAAAGAGCATCCTGTTGAAA<br>ATACTCAATTGCAAAATGAAAAGCTCTATCTCTATTATCTCCAAAATGGAAGAGACATGTATGTGGACCAAGAATT<br>AGATATTAATCGTTTAAGTGATTATGATGTCGATgcCATTGTTCCACAAAGTTTCCTTAAAGACGATTCAATAGACA<br>ATAAGGTCTTAACGCGTTCTGATAAAAATCGTGGTAAATCGGATAACGTTCCAAGTGAAGAAGTAGTCAAAAAGA<br>TGAAAAACTATTGGAGACAACTTCTAAACGCCAAGTTAATCACTCAACGTAAGTTTGATAATTTAACGAAAGCTGA<br>ACGTGGAGGTTTGAGTGAACTTGATAAAGCTGGTTTTATCAAACGCCAATTGGTTGAAACTCGCCAAATCACTAAG<br>CATGTGGCACAAATTTTGGATAGTCGCATGAATACTAAATACGATGAAAATGATAAACTTATTCGAGAGGTTAAAG<br>TGATTACCTTAAAATCTAAATTAGTTTCTGACTTCCGAAAAGATTTCCAATTCTATAAAGTACGTGAGATTAACAATT |

FIG. 5 (continued)

CMV-T7-Cas9 D10A/H840A-3XFLAG-VP64:

ACCATCATGCCCATGATGCGTATCTAAATGCCGTCGTTGGAACTGCTTTGATTAAGAAATATCCAAAACTTGAATCG
GAGTTTGTCTATGGTGATTATAAAGTTTATGATGTTCGTAAAATGATTGCTAAGTCTGAGCAAGAAATAGGCAAAG
CAACCGCAAAATATTTCTTTTACTCTAATATCATGAACTTCTTCAAAACAGAAATTACACTTGCAAATGGAGAGATT
CGCAAACGCCCTCTAATCGAAACTAATGGGGAAACTGGAGAAATTGTCTGGGATAAAGGGCGAGATTTTGCCACA
GTGCGCAAAGTATTGTCCATGCCCCAAGTCAATATTGTCAAGAAAACAGAAGTACAGACAGGCGGATTCTCCAAG
GAGTCAATTTTACCAAAAAGAAATTCGGACAAGCTTATTGCTCGTAAAAAAGACTGGGATCCAAAAAAATATGGT
GGTTTTGATAGTCCAACGGTAGCTTATTCAGTCCTAGTGGTTGCTAAGGTGGAAAAAGGGAAATCGAAGAAGTTA
AAATCCGTTAAAGAGTTACTAGGGATCACAATTATGGAAAGAAGTTCCTTTGAAAAAAATCCGATTGACTTTTTAG
AAGCTAAAGGATATAAGGAAGTTAAAAAAGACTTAATCATTAAACTACCTAAATATAGTCTTTTTGAGTTAGAAAA
CGGTCGTAAACGGATGCTGGCTAGTGCCGGAGAATTACAAAAAGGAAATGAGCTGGCTCTGCCAAGCAAATATGT
GAATTTTTTATATTTAGCTAGTCATTATGAAAAGTTGAAGGGTAGTCCAGAAGATAACGAACAAAAACAATTGTTT
GTGGAGCAGCATAAGCATTATTTAGATGAGATTATTGAGCAAATCAGTGAATTTTCTAAGCGTGTTATTTTAGCAG
ATGCCAATTTAGATAAAGTTCTTAGTGCATATAACAAACATAGAGACAAACCAATACGTGAACAAGCAGAAAATAT
TATTCATTTATTTACGTTGACGAATCTTGGAGCTCCCGCTGCTTTTAAATATTTTGATACAACAATTGATCGTAAACG
ATATACGTCTACAAAAGAAGTTTTAGATGCCACTCTTATCCATCAATCCATCACTGGTCTTTATGAAACACGCATTG
ATTTGAGTCAGCTAGGAGGTGACGGTTCTCCCAAGAAGAAGAGGAAAGTCTCGAGCGACTACAAAGACCATGAC
GGTGATTATAAAGATCATGACATCGATTACAAGGATGACGATGACAAGGctgcaggaggcggtggaagcGGGCGCGCC
GACGCGCTGGACGATTTCGATCTCGACATGCTGGGTTCTGATGCCCTCGATGACTTTGACCTGGATATGTTGGGAA
GCGACGCATTGGATGACTTTGATCTGGACATGCTCGGCTCCGATGCTCTGGACGATTTCGATCTCGATATGTTATA
AccggtCATCATCACCATCACCATTGAGTTTAAACCCGCTGATCAGCCTCGACTGTGCCTTCTAGTTGCCAGCCATCT
GTTGTTTGCCCCTCCCCCGTGCCTTCCTTGACCCTGGAAGGTGCCACTCCCACTGTCCTTTCCTAATAAAATGAGGA
AATTGCATCGCATTGTCTGAGTAGGTGTCATTCTATTCTGGGGGGTGGGGTGGGGCAGGACAGCAAGGGGGAGG
ATTGGGAAGACAATAGCAGGCATGCTGGGGATGCGGTGGGCTCTATGGCTTCTGAGGCGGAAAGAACCAGCTGG
GGCTCGATACCGTCGACCTCTAGCTAGAGCTTGGCGTAATCATGGTCATAGCTGTTTCCTGTGTGAAATTGTTATCC
GCTCACAATTCCACACAACATACGAGCCGGAAGCATAAAGTGTAAAGCCTAGGGTGCCTAATGAGTGAGCTAACT
CACATTAATTGCGTTGCGCTCACTGCCCGCTTTCCAGTCGGGAAACCTGTCGTGCCAGCTGCATTAATGAATCGGC
CAACGCGCGGGGAGAGGCGGTTTGCGTATTGGGCGCTCTTCCGCTTCCTCGCTCACTGACTCGCTGCGCTCGGTC
GTTCGGCTGCGGCGAGCGGTATCAGCTCACTCAAAGGCGGTAATACGGTTATCCACAGAATCAGGGGATAACGCA
GGAAAGAACATGTGAGCAAAAGGCCAGCAAAAGGCCAGGAACCGTAAAAAGGCCGCGTTGCTGGCGTTTTTCCA
TAGGCTCCGCCCCCCTGACGAGCATCACAAAAATCGACGCTCAAGTCAGAGGTGGCGAAACCCGACAGGACTATA
AAGATACCAGGCGTTTCCCCCTGGAAGCTCCCTCGTGCGCTCTCCTGTTCCGACCCTGCCGCTTACCGGATACCTGT
CCGCCTTTCTCCCTTCGGGAAGCGTGGCGCTTTCTCAATGCTCACGCTGTAGGTATCTCAGTTCGGTGTAGGTCGTT
CGCTCCAAGCTGGGCTGTGTGCACGAACCCCCCGTTCAGCCCGACCGCTGCGCCTTATCCGGTAACTATCGTCTTG
AGTCCAACCCGGTAAGACACGACTTATCGCCACTGGCAGCAGCCACTGGTAACAGGATTAGCAGAGCGAGGTATG
TAGGCGGTGCTACAGAGTTCTTGAAGTGGTGGCCTAACTACGGCTACACTAGAAGGACAGTATTTGGTATCTGCG
CTCTGCTGAAGCCAGTTACCTTCGGAAAAAGAGTTGGTAGCTCTTGATCCGGCAAACAAACCACCGCTGGTAGCG
GTGGTTTTTTTGTTTGCAAGCAGCAGATTACGCGCAGAAAAAAAGGATCTCAAGAAGATCCTTTGATCTTTTCTAC
GGGGTCTGACGCTCAGTGGAACGAAAACTCACGTTAAGGGATTTTGGTCATGAGATTATCAAAAAGGATCTTCAC
CTAGATCCTTTTAAATTAAAAATGAAGTTTTAAATCAATCTAAAGTATATATGAGTAAACTTGGTCTGACAGTTACC
AATGCTTAATCAGTGAGGCACCTATCTCAGCGATCTGTCTATTTCGTTCATCCATAGTTGCCTGACTCCCCGTCGTGT
AGATAACTACGATACGGGAGGGCTTACCATCTGGCCCCAGTGCTGCAATGATACCGCGAGACCCACGCTCACCGG
CTCCAGATTTATCAGCAATAAACCAGCCAGCCGGAAGGGCCGAGCGCAGAAGTGGTCCTGCAACTTTATCCGCCT
CCATCCAGTCTATTAATTGTTGCCGGGAAGCTAGAGTAAGTAGTTCGCCAGTTAATAGTTTGCGCAACGTTGTTGC
CATTGCTACAGGCATCGTGGTGTCACGCTCGTCGTTTGGTATGGCTTCATTCAGCTCCGGTTCCCAACGATCAAGG
CGAGTTACATGATCCCCCATGTTGTGCAAAAAAGCGGTTAGCTCCTTCGGTCCTCCGATCGTTGTCAGAAGTAAGT
TGGCCGCAGTGTTATCACTCATGGTTATGGCAGCACTGCATAATTCTCTTACTGTCATGCCATCCGTAAGATGCTTT

FIG. 5 (continued)

| CMV-T7-Cas9 D10A/H840A-3XFLAG-VP64: |
| --- |
| TCTGTGACTGGTGAGTACTCAACCAAGTCATTCTGAGAATAGTGTATGCGGCGACCGAGTTGCTCTTGCCCGGCGT<br>CAATACGGGATAATACCGCGCCACATAGCAGAACTTTAAAAGTGCTCATCATTGGAAAACGTTCTTCGGGGCGAA<br>AACTCTCAAGGATCTTACCGCTGTTGAGATCCAGTTCGATGTAACCCACTCGTGCACCCAACTGATCTTCAGCATCT<br>TTTACTTTCACCAGCGTTTCTGGGTGAGCAAAAACAGGAAGGCAAAATGCCGCAAAAAAGGGAATAAGGGCGAC<br>ACGGAAATGTTGAATACTCATACTCTTCCTTTTTCAATATTATTGAAGCATTTATCAGGGTTATTGTCTCATGAGCGG<br>ATACATATTTGAATGTATTTAGAAAAATAAACAAATAGGGGTTCCGCGCACATTTCCCCGAAAAGTGCCACCTGAC<br>GTCGACGGATCGGGAGATCGATCTCCCGATCCCCTAGGGTCGACTCTCAGTACAATCTGCTCTGATGCCGCATAGT<br>TAAGCCAGTATCTGCTCCCTGCTTGTGTGTTGGAGGTCGCTGAGTAGTGCGCGAGCAAAATTTAAGCTACAACAAG<br>GCAAGGCTTGACCGACAATTGCATGAAGAATCTGCTTAGGGTTAGGCGTTTTGCGCTGCTTCGCGATGTACGGGC<br>CAGATATACGCGTTGACATTGATTATTGACTAGTTATTAATAGTAATCAATTACGGGGTCATTAGTTCATAGCCCAT<br>ATATGGAGTTCCGCGTTACATAACTTACGGTAAATGGCCCGCCTGGCTGACCGCCCAACGACCCCCGCCCATTGAC<br>GTCAATAATGACGTATGTTCCCATAGTAACGCCAATAGGGACTTTCCATTGACGTCAATGGGTGGACTATTTACGG<br>TAAACTGCCCACTTGGCAGTACATCAAGTGTATCC **(SEQ ID NO:108)** |

FIG. 6

| MV-T7-Cas9 recoded D10A/H840A-3XFLAG-VP64 |
| --- |
| ATATGCCAAGTACGCCCCCTATTGACGTCAATGACGGTAAATGGCCCGCCTGGCATTATGCCCAGTACATGACCTT<br>ATGGGACTTTCCTACTTGGCAGTACATCTACGTATTAGTCATCGCTATTACCATGGTGATGCGGTTTTGGCAGTACA<br>TCAATGGGCGTGGATAGCGGTTTGACTCACGGGGATTTCCAAGTCTCCACCCCATTGACGTCAATGGGAGTTTGTT<br>TTGGCACCAAAATCAACGGGACTTTCCAAAATGTCGTAACAACTCCGCCCCATTGACGCAAATGGGCGGTAGGCG<br>TGTACGGTGGGAGGTCTATATAAGCAGAGCTGGTTTAGTGAACCGTCAGATCCGCTAGAGATCCGCGGCCGCTAA<br>TACGACTCACTATAGGGAGAGCCGCCACCATGGATAAAAAGTATTCTATTGGTTTAGcCATCGGCACTAATTCCGTT<br>GGATGGGCTGTCATAACCGATGAATACAAAGTACCTTCAAAGAAATTTAAGGTGTTGGGGAACACAGACCGTCAT<br>TCGATTAAAAAGAATCTTATCGGTGCCCTCCTATTCGATAGTGGCGAAACGGCAGAGGCGACTCGCCTGAAACGA<br>ACCGCTCGGAGAAGGTATACACGTCGCAAGAACCGAATATGTTACTTACAAGAAATTTTTAGCAATGAGATGGCC<br>AAAGTTGACGATTCTTTCTTTCACCGTTTGGAAGAGTCCTTCCTTGTCGAAGAGGACAAGAAACATGAACGGCACC<br>CCATCTTTGGAAACATAGTAGATGAGGTGGCATATCATGAAAAGTACCCAACGATTTATCACCTCAGAAAAAAGCT<br>AGTTGACTCAACTGATAAAGCGGACCTGAGGTTAATCTACTTGGCTCTTGCCCATATGATAAAGTTCCGTGGGCAC<br>TTTCTCATTGAGGGTGATCTAAATCCGGACAACTCGGATGTCGACAAACTGTTCATCCAGTTAGTACAAACCTATAA<br>TCAGTTGTTTGAAGAGAACCCTATAAATGCAAGTGGCGTGGATGCGAAGGCTATTCTTAGCGCCCGCCTCTCTAAA<br>TCCCGACGGCTAGAAAACCTGATCGCACAATTACCCGGAGAGAAGAAAAATGGGTTGTTCGGTAACCTTATAGCG<br>CTCTCACTAGGCCTGACACCAAATTTTAAGTCGAACTTCGACTTAGCTGAAGATGCCAAATTGCAGCTTAGTAAGG<br>ACACGTACGATGACGATCTCGACAATCTACTGGCACAAATTGGAGATCAGTATGCGGACTTATTTTTGGCTGCCAA<br>AAACCTTAGCGATGCAATCCTCCTATCTGACATACTGAGAGTTAATACTGAGATTACCAAGGCGCCGTTATCCGCTT<br>CAATGATCAAAAGGTACGATGAACATCACCAAGACTTGACACTTCTCAAGGCCCTAGTCCGTCAGCAACTGCCTGA<br>GAAATATAAGGAAATATTCTTTGATCAGTCGAAAAACGGGTACGCAGGTTATATTGACGGCGGAGCGAGTCAAGA<br>GGAATTCTACAAGTTTATCAAACCCATATTAGAGAAGATGGATGGGACGGAAGAGTTGCTTGTAAAACTCAATCG<br>CGAAGATCTACTGCGAAAGCAGCGGACTTTCGACAACGGTAGCATTCCACATCAAATCCACTTAGGCGAATTGCAT<br>GCTATACTTAGAAGGCAGGAGGATTTTTATCCGTTCCTCAAAGACAATCGTGAAAAGATTGAGAAAATCCTAACCT<br>TTCGCATACCTTACTATGTGGGACCCCTGGCCCGAGGGAACTCTCGGTTCGCATGGATGACAAGAAAGTCCGAAG<br>AAACGATTACTCCATGGAATTTTGAGGAAGTTGTCGATAAAGGTGCGTCAGCTCAATCGTTCATCGAGAGGATGA<br>CCAACTTTGACAAGAATTTACCGAACGAAAAAGTATTGCCTAAGCACAGTTTACTTTACGAGTATTTCACAGTGTAC<br>AATGAACTCACGAAAGTTAAGTATGTCACTGAGGGCATGCGTAAACCCGCCTTTCTAAGCGGAGAACAGAAGAAA<br>GCAATAGTAGATCTGTTATTCAAGACCAACCGCAAAGTGACAGTTAAGCAATTGAAAGAGGACTACTTTAAGAAA<br>ATTGAATGCTTCGATTCTGTCGAGATCTCCGGGGTAGAAGATCGATTTAATGCGTCACTTGGTACGTATCATGACC<br>TCCTAAAGATAATTAAAGATAAGGACTTCCTGGATAACGAAGAGAATGAAGATATCTTAGAAGATATAGTGTTGA<br>CTCTTACCCTCTTTGAAGATCGGGAAATGATTGAGGAAAGACTAAAAACATACGCTCACCTGTTCGACGATAAGGT<br>TATGAAACAGTTAAAGAGGCGTCGCTATACGGGCTGGGGACGATTGTCGCGGAAACTTATCAACGGGATAAGAG<br>ACAAGCAAAGTGGTAAAACTATTCTCGATTTTCTAAAGAGCGACGGCTTCGCCAATAGGAACTTTATGCAGCTGAT<br>CCATGATGACTCTTTAACCTTCAAAGAGGATATACAAAAGGCACAGGTTTCCGGACAAGGGGACTCATTGCACGA<br>ACATATTGCGAATCTTGCTGGTTCGCCAGCCATCAAAAAGGGCATACTCCAGACAGTCAAAGTAGTGGATGAGCT<br>AGTTAAGGTCATGGGACGTCACAAACCGGAAAACATTGTAATCGAGATGGCACGCGAAAATCAAACGACTCAGA<br>AGGGGCAAAAAAACAGTCGAGAGCGGATGAAGAGAATAGAAGAGGGTATTAAAGAACTGGGCAGCCAGATCTT<br>AAAGGAGCATCCTGTGGAAAATACCCAATTGCAGAACGAGAAACTTTACCTCTATTACCTACAAAATGGAAGGGA<br>CATGTATGTTGATCAGGAACTGGACATAAACCGTTTATCTGATTACGACGTCGATgcCATTGTACCCCAATCCTTTTT<br>GAAGGACGATTCAATCGACAATAAAGTGCTTACACGCTCGGATAAGAACCGAGGGAAAAGTGACAATGTTCCAA<br>GCGAGGAAGTCGTAAAGAAAATGAAGAACTATTGGCGGCAGCTCCTAAATGCGAAACTGATAACGCAAAGAAAG<br>TTCGATAACTTAACTAAAGCTGAGAGGGGTGGCTTGTCTGAACTTGACAAGGCCGGATTTATTAAACGTCAGCTCG<br>TGGAAACCCGCCAAATCACAAAGCATGTTGCACAGATACTAGATTCCCGAATGAATACGAAATACGACGAGAACG<br>ATAAGCTGATTCGGGAAGTCAAAGTAATCACTTTAAAGTCAAAATTGGTGTCGGACTTCAGAAAGGATTTTCAATT |

FIG. 6 (continued)

MV-T7-Cas9 recoded D10A/H840A-3XFLAG-VP64

CTATAAAGTTAGGGAGATAAATAACTACCACCATGCGCACGACGCTTATCTTAATGCCGTCGTAGGGACCGCACTC
ATTAAGAAATACCCGAAGCTAGAAAGTGAGTTTGTGTATGGTGATTACAAAGTTTATGACGTCCGTAAGATGATC
GCGAAAAGCGAACAGGAGATAGGCAAGGCTACAGCCAAATACTTCTTTTATTCTAACATTATGAATTTCTTTAAGA
CGGAAATCACTCTGGCAAACGGAGAGATACGCAAACGACCTTTAATTGAAACCAATGGGGAGACAGGTGAAATC
GTATGGGATAAGGGCCGGGACTTCGCGACGGTGAGAAAAGTTTTGTCCATGCCCCAAGTCAACATAGTAAAGAAA
ACTGAGGTGCAGACCGGAGGGTTTTCAAAGGAATCGATTCTTCCAAAAAGGAATAGTGATAAGCTCATCGCTCGT
AAAAAGGACTGGGACCCGAAAAAGTACGGTGGCTTCGATAGCCCTACAGTTGCCTATTCTGTCCTAGTAGTGGCA
AAAGTTGAGAAGGGAAAATCCAAGAAACTGAAGTCAGTCAAAGAATTATTGGGGATAACGATTATGGAGCGCTC
GTCTTTTGAAAAGAACCCCATCGACTTCCTTGAGGCGAAAGGTTACAAGGAAGTAAAAAAGGATCTCATAATTAAA
CTACCAAAGTATAGTCTGTTTGAGTTAGAAAATGGCCGAAAACGGATGTTGGCTAGCGCCGGAGAGCTTCAAAAG
GGGAACGAACTCGCACTACCGTCTAAATACGTGAATTTCCTGTATTTAGCGTCCCATTACGAGAAGTTGAAAGGTT
CACCTGAAGATAACGAACAGAAGCAACTTTTTGTTGAGCAGCACAAACATTATCTCGACGAAATCATAGAGCAAAT
TTCGGAATTCAGTAAGAGAGTCATCCTAGCTGATGCCAATCTGGACAAAGTATTAAGCGCATACAACAAGCACAG
GGATAAACCCATACGTGAGCAGGCGGAAAATATTATCCATTTGTTTACTCTTACCAACCTCGGCGCTCCAGCCGCA
TTCAAGTATTTTGACACAACGATAGATCGCAAACGATACACTTCTACCAAGGAGGTGCTAGACGCGACACTGATTC
ACCAATCCATCACGGGATTATATGAAACTCGGATAGATTTGTCACAGCTTGGGGGTGACGGATCCCCCAAGAAGA
AGAGGAAAGTCTCGAGCGACTACAAAGACCATGACGGTGATTATAAAGATCATGACATCGATTACAAGGATGACG
ATGACAAGGctgcaggaggcggtggaagcGGGCGCGCCGACGCGCTGGACGATTTCGATCTCGACATGCTGGGTTCTGA
TGCCCTCGATGACTTTGACCTGGATATGTTGGGAAGCGACGCATTGGATGACTTTGATCTGGACATGCTCGGCTCC
GATGCTCTGGACGATTTCGATCTCGATATGTTATAAccggtCATCATCACCATCACCATTGAGTTTAAACCCGCTGAT
CAGCCTCGACTGTGCCTTCTAGTTGCCAGCCATCTGTTGTTTGCCCCTCCCCCGTGCCTTCCTTGACCCTGGAAGGT
GCCACTCCCACTGTCCTTTCCTAATAAAATGAGGAAATTGCATCGCATTGTCTGAGTAGGTGTCATTCTATTCTGGG
GGGTGGGGTGGGGCAGGACAGCAAGGGGGAGGATTGGGAAGACAATAGCAGGCATGCTGGGGATGCGGTGGG
CTCTATGGCTTCTGAGGCGGAAAGAACCAGCTGGGGCTCGATACCGTCGACCTCTAGCTAGAGCTTGGCGTAATC
ATGGTCATAGCTGTTTCCTGTGTGAAATTGTTATCCGCTCACAATTCCACACAACATACGAGCCGGAAGCATAAAG
TGTAAAGCCTAGGGTGCCTAATGAGTGAGCTAACTCACATTAATTGCGTTGCGCTCACTGCCCGCTTTCCAGTCGG
GAAACCTGTCGTGCCAGCTGCATTAATGAATCGGCCAACGCGCGGGGAGAGGCGGTTTGCGTATTGGGCGCTCTT
CCGCTTCCTCGCTCACTGACTCGCTGCGCTCGGTCGTTCGGCTGCGGCGAGCGGTATCAGCTCACTCAAAGGCGGT
AATACGGTTATCCACAGAATCAGGGGATAACGCAGGAAAGAACATGTGAGCAAAAGGCCAGCAAAAGGCCAGG
AACCGTAAAAAGGCCGCGTTGCTGGCGTTTTTCCATAGGCTCCGCCCCCCTGACGAGCATCACAAAAATCGACGCT
CAAGTCAGAGGTGGCGAAACCCGACAGGACTATAAAGATACCAGGCGTTTCCCCCTGGAAGCTCCCTCGTGCGCT
CTCCTGTTCCGACCCTGCCGCTTACCGGATACCTGTCCGCCTTTCTCCCTTCGGGAAGCGTGGCGCTTTCTCAATGC
TCACGCTGTAGGTATCTCAGTTCGGTGTAGGTCGTTCGCTCCAAGCTGGGCTGTGTGCACGAACCCCCCGTTCAGC
CCGACCGCTGCGCCTTATCCGGTAACTATCGTCTTGAGTCCAACCCGGTAAGACACGACTTATCGCCACTGGCAGC
AGCCACTGGTAACAGGATTAGCAGAGCGAGGTATGTAGGCGGTGCTACAGAGTTCTTGAAGTGGTGGCCTAACT
ACGGCTACACTAGAAGGACAGTATTTGGTATCTGCGCTCTGCTGAAGCCAGTTACCTTCGGAAAAAGAGTTGGTA
GCTCTTGATCCGGCAAACAAACCACCGCTGGTAGCGGTGGTTTTTTTGTTTGCAAGCAGCAGATTACGCGCAGAAA
AAAAGGATCTCAAGAAGATCCTTTGATCTTTTCTACGGGGTCTGACGCTCAGTGGAACGAAAACTCACGTTAAGG
GATTTTGGTCATGAGATTATCAAAAAGGATCTTCACCTAGATCCTTTTAAATTAAAAATGAAGTTTTAAATCAATCT
AAAGTATATATGAGTAAACTTGGTCTGACAGTTACCAATGCTTAATCAGTGAGGCACCTATCTCAGCGATCTGTCT
ATTTCGTTCATCCATAGTTGCCTGACTCCCCGTCGTGTAGATAACTACGATACGGGAGGGCTTACCATCTGGCCCCA
GTGCTGCAATGATACCGCGAGACCCACGCTCACCGGCTCCAGATTTATCAGCAATAAACCAGCCAGCCGGAAGGG
CCGAGCGCAGAAGTGGTCCTGCAACTTTATCCGCCTCCATCCAGTCTATTAATTGTTGCCGGGAAGCTAGAGTAAG
TAGTTCGCCAGTTAATAGTTTGCGCAACGTTGTTGCCATTGCTACAGGCATCGTGGTGTCACGCTCGTCGTTTGGTA
TGGCTTCATTCAGCTCCGGTTCCCAACGATCAAGGCGAGTTACATGATCCCCCATGTTGTGCAAAAAAGCGGTTAG
CTCCTTCGGTCCTCCGATCGTTGTCAGAAGTAAGTTGGCCGCAGTGTTATCACTCATGGTTATGGCAGCACTGCATA

FIG. 6 (continued)

| MV-T7-Cas9 recoded D10A/H840A-3XFLAG-VP64 |
| --- |
| ATTCTCTTACTGTCATGCCATCCGTAAGATGCTTTTCTGTGACTGGTGAGTACTCAACCAAGTCATTCTGAGAATAG TGTATGCGGCGACCGAGTTGCTCTTGCCCGGCGTCAATACGGGATAATACCGCGCCACATAGCAGAACTTTAAAA GTGCTCATCATTGGAAAACGTTCTTCGGGGCGAAAACTCTCAAGGATCTTACCGCTGTTGAGATCCAGTTCGATGT AACCCACTCGTGCACCCAACTGATCTTCAGCATCTTTTACTTTCACCAGCGTTTCTGGGTGAGCAAAAACAGGAAG GCAAAATGCCGCAAAAAAGGGAATAAGGGCGACACGGAAATGTTGAATACTCATACTCTTCCTTTTTCAATATTAT TGAAGCATTTATCAGGGTTATTGTCTCATGAGCGGATACATATTTGAATGTATTTAGAAAAATAAACAAATAGGGG TTCCGCGCACATTTCCCCGAAAAGTGCCACCTGACGTCGACGGATCGGGAGATCGATCTCCCGATCCCCTAGGGTC GACTCTCAGTACAATCTGCTCTGATGCCGCATAGTTAAGCCAGTATCTGCTCCCTGCTTGTGTGTTGGAGGTCGCTG AGTAGTGCGCGAGCAAAATTTAAGCTACAACAAGGCAAGGCTTGACCGACAATTGCATGAAGAATCTGCTTAGGG TTAGGCGTTTTGCGCTGCTTCGCGATGTACGGGCCAGATATACGCGTTGACATTGATTATTGACTAGTTATTAATAG TAATCAATTACGGGGTCATTAGTTCATAGCCCATATATGGAGTTCCGCGTTACATAACTTACGGTAAATGGCCCGC CTGGCTGACCGCCCAACGACCCCCGCCCATTGACGTCAATAATGACGTATGTTCCCATAGTAACGCCAATAGGGAC TTTCCATTGACGTCAATGGGTGGACTATTTACGGTAAACTGCCCACTTGGCAGTACATCAAGTGTATC (SEQ ID NO:109) |

FIG. 7

Cas9-activator protein

MDKKYSIGLAIGTNSVGWAVITDEYKVPSKKFKVLGNTDRHSIKKNLIGALLFDSGETAEATRL
KRTARRRYTRRKNRICYLQEIFSNEMAKVDDSFFHRLEESFLVEEDKKHERHPIFGNIVDEVAY
HEKYPTIYHLRKKLVDSTDKADLRLIYLALAHMIKFRGHFLIEGDLNPDNSDVDKLFIQLVQTY
NQLFEENPINASGVDAKAILSARLSKSRRLENLIAQLPGEKKNGLFGNLIALSLGLTPNFKSNF
DLAEDAKLQLSKDTYDDDLDNLLAQIGDQYADLFLAAKNLSDAILLSDILRVNTEITKAPLSAS
MIKRYDEHHQDLTLLKALVRQQLPEKYKEIFFDQSKNGYAGYIDGGASQEEFYKFIKPILEKMD
GTEELLVKLNREDLLRKQRTFDNGSIPHQIHLGELHAILRRQEDFYPFLKDNREKIEKILTFRI
PYYVGPLARGNSRFAWMTRKSEETITPWNFEEVVDKGASAQSFIERMTNFDKNLPNEKVLPKHS
LLYEYFTVYNELTKVKYVTEGMRKPAFLSGEQKKAIVDLLFKTNRKVTVKQLKEDYFKKIECFD
SVEISGVEDRFNASLGTYHDLLKIIKDKDFLDNEENEDILEDIVLTLTLFEDREMIEERLKTYA
HLFDDKVMKQLKRRRYTGWGRLSRKLINGIRDKQSGKTILDFLKSDGFANRNFMQLIHDDSLTF
KEDIQKAQVSGQGDSLHEHIANLAGSPAIKKGILQTVKVVDELVKVMGRHKPENIVIEMARENQ
TTQKGQKNSRERMKRIEEGIKELGSQILKEHPVENTQLQNEKLYLYYLQNGRDMYVDQELDINR
LSDYDVDAIVPQSFLKDDSIDNKVLTRSDKNRGKSDNVPSEEVVKKMKNYWRQLLNAKLITQRK
FDNLTKAERGGLSELDKAGFIKRQLVETRQITKHVAQILDSRMNTKYDENDKLIREVKVITLKS
KLVSDFRKDFQFYKVREINNYHHAHDAYLNAVVGTALIKKYPKLESEFVYGDYKVYDVRKMIAK
SEQEIGKATAKYFFYSNIMNFFKTEITLANGEIRKRPLIETNGETGEIVWDKGRDFATVRKVLS
MPQVNIVKKTEVQTGGFSKESILPKRNSDKLIARKKDWDPKKYGGFDSPTVAYSVLVVAKVEKG
KSKKLKSVKELLGITIMERSSFEKNPIDFLEAKGYKEVKKDLIIKLPKYSLFELENGRKRMLAS
AGELQKGNELALPSKYVNFLYLASHYEKLKGSPEDNEQKQLFVEQHKHYLDEIIEQISEFSKRV
ILADANLDKVLSAYNKHRDKPIREQAENIIHLFTLTNLGAPAAFKYFDTTIDRKRYTSTKEVLD
ATLIHQSITGLYETRIDLSQLGGDGSpkkkrkvssDYKDHDGDYKDHDIDYKDDDDKAAGGGGS
GRADALDDFDLDMLGSDALDDFDLDMLGSDALDDFDLDMLGSDALDDFDLDML (SEQ ID NO:110)

FIG. 8A

| dCas9-NLS-3XFLAG-HP1alpha |
| --- |
| MDKKYSIGLAIGTNSVGWAVITDEYKVPSKKFKVLGNTDRHSIKKNLIGALLFDSGETAEATRL<br>KRTARRRYTRRKNRICYLQEIFSNEMAKVDDSFFHRLEESFLVEEDKKHERHPIFGNIVDEVAY<br>HEKYPTIYHLRKKLVDSTDKADLRLIYLALAHMIKFRGHFLIEGDLNPDNSDVDKLFIQLVQTY<br>NQLFEENPINASGVDAKAILSARLSKSRRLENLIAQLPGEKKNGLFGNLIALSLGLTPNFKSNF<br>DLAEDAKLQLSKDTYDDDLDNLLAQIGDQYADLFLAAKNLSDAILLSDILRVNTEITKAPLSAS<br>MIKRYDEHHQDLTLLKALVRQQLPEKYKEIFFDQSKNGYAGYIDGGASQEEFYKFIKPILEKMD<br>GTEELLVKLNREDLLRKQRTFDNGSIPHQIHLGELHAILRRQEDFYPFLKDNREKIEKILTFRI<br>PYYVGPLARGNSRFAWMTRKSEETITPWNFEEVVDKGASAQSFIERMTNFDKNLPNEKVLPKHS<br>LLYEYFTVYNELTKVKYVTEGMRKPAFLSGEQKKAIVDLLFKTNRKVTVKQLKEDYFKKIECFD<br>SVEISGVEDRFNASLGTYHDLLKIIKDKDFLDNEENEDILEDIVLTLTLFEDREMIEERLKTYA<br>HLFDDKVMKQLKRRRYTGWGRLSRKLINGIRDKQSGKTILDFLKSDGFANRNFMQLIHDDSLTF<br>KEDIQKAQVSGQGDSLHEHIANLAGSPAIKKGILQTVKVVDELVKVMGRHKPENIVIEMARENQ<br>TTQKGQKNSRERMKRIEEGIKELGSQILKEHPVENTQLQNEKLYLYYLQNGRDMYVDQELDINR<br>LSDYDVDAIVPQSFLKDDSIDNKVLTRSDKNRGKSDNVPSEEVVKKMKNYWRQLLNAKLITQRK<br>FDNLTKAERGGLSELDKAGFIKRQLVETRQITKHVAQILDSRMNTKYDENDKLIREVKVITLKS<br>KLVSDFRKDFQFYKVREINNYHHAHDAYLNAVVGTALIKKYPKLESEFVYGDYKVYDVRKMIAK<br>SEQEIGKATAKYFFYSNIMNFFKTEITLANGEIRKRPLIETNGETGEIVWDKGRDFATVRKVLS<br>MPQVNIVKKTEVQTGGFSKESILPKRNSDKLIARKKDWDPKKYGGFDSPTVAYSVLVVAKVEKG<br>KSKKLKSVKELLGITIMERSSFEKNPIDFLEAKGYKEVKKDLIIKLPKYSLFELENGRKRMLAS<br>AGELQKGNELALPSKYVNFLYLASHYEKLKGSPEDNEQKQLFVEQHKHYLDEIIEQISEFSKRV<br>ILADANLDKVLSAYNKHRDKPIREQAENIIHLFTLTNLGAPAAFKYFDTTIDRKRYTSTKEVLD<br>ATLIHQSITGLYETRIDLSQLGGDGSPKKKRKVSSDYKDHDGDYKDHDIDYKDDDDKAAGGGGS<br>MKEGENNKPREKSESNKRKSNFSNSADDIKSKKKREQSNDIARGFERGLEPEKIIGATDSCGDL<br>MFLMKWKDTDEADLVLAKEANVKCPQIVIAFYEERLTWHAYPEDAENKEKETAKS (SEQ ID<br>NO:111) |

FIG. 8B

| dCas9-NLS-3XFLAG-HP1beta |
| --- |
| MDKKYSIGLAIGTNSVGWAVITDEYKVPSKKFKVLGNTDRHSIKKNLIGALLFDSGETAEATRL<br>KRTARRRYTRRKNRICYLQEIFSNEMAKVDDSFFHRLEESFLVEEDKKHERHPIFGNIVDEVAY<br>HEKYPTIYHLRKKLVDSTDKADLRLIYLALAHMIKFRGHFLIEGDLNPDNSDVDKLFIQLVQTY<br>NQLFEENPINASGVDAKAILSARLSKSRRLENLIAQLPGEKKNGLFGNLIALSLGLTPNFKSNF<br>DLAEDAKLQLSKDTYDDDLDNLLAQIGDQYADLFLAAKNLSDAILLSDILRVNTEITKAPLSAS<br>MIKRYDEHHQDLTLLKALVRQQLPEKYKEIFFDQSKNGYAGYIDGGASQEEFYKFIKPILEKMD<br>GTEELLVKLNREDLLRKQRTFDNGSIPHQIHLGELHAILRRQEDFYPFLKDNREKIEKILTFRI<br>PYYVGPLARGNSRFAWMTRKSEETITPWNFEEVVDKGASAQSFIERMTNFDKNLPNEKVLPKHS<br>LLYEYFTVYNELTKVKYVTEGMRKPAFLSGEQKKAIVDLLFKTNRKVTVKQLKEDYFKKIECFD<br>SVEISGVEDRFNASLGTYHDLLKIIKDKDFLDNEENEDILEDIVLTLTLFEDREMIEERLKTYA<br>HLFDDKVMKQLKRRRYTGWGRLSRKLINGIRDKQSGKTILDFLKSDGFANRNFMQLIHDDSLTF<br>KEDIQKAQVSGQGDSLHEHIANLAGSPAIKKGILQTVKVVDELVKVMGRHKPENIVIEMARENQ<br>TTQKGQKNSRERMKRIEEGIKELGSQILKEHPVENTQLQNEKLYLYYLQNGRDMYVDQELDINR<br>LSDYDVDAIVPQSFLKDDSIDNKVLTRSDKNRGKSDNVPSEEVVKKMKNYWRQLLNAKLITQRK<br>FDNLTKAERGGLSELDKAGFIKRQLVETRQITKHVAQILDSRMNTKYDENDKLIREVKVITLKS<br>KLVSDFRKDFQFYKVREINNYHHAHDAYLNAVVGTALIKKYPKLESEFVYGDYKVYDVRKMIAK<br>SEQEIGKATAKYFFYSNIMNFFKTEITLANGEIRKRPLIETNGETGEIVWDKGRDFATVRKVLS<br>MPQVNIVKKTEVQTGGFSKESILPKRNSDKLIARKKDWDPKKYGGFDSPTVAYSVLVVAKVEKG<br>KSKKLKSVKELLGITIMERSSFEKNPIDFLEAKGYKEVKKDLIIKLPKYSLFELENGRKRMLAS<br>AGELQKGNELALPSKYVNFLYLASHYEKLKGSPEDNEQKQLFVEQHKHYLDEIIEQISEFSKRV<br>ILADANLDKVLSAYNKHRDKPIREQAENIIHLFTLTNLGAPAAFKYFDTTIDRKRYTSTKEVLD<br>ATLIHQSITGLYETRIDLSQLGGDGSPKKKRKVSSDYKDHDGDYKDHDIDYKDDDDKAAGGGGS<br>TAHETDKSEGGKRKADSDSEDKGEESKPKKKKEESEKPRGFARGLEPERIIGATDSSGELMFLM<br>KWKNSDEADLVPAKEANVKCPQVVISFYEERLTWHSYPSEDDDKKDDKN. (SEQ ID NO:112) |

box = nuclear localization signal underline = triple flag tag double underline = HP1alpha hinge and chromoshadow domains

FIG. 9

| dCas9-3XFLAG-TET1CD |
| --- |
| MDKKYSIGLAIGTNSVGWAVITDEYKVPSKKFKVLGNTDRHSIKKNLIGALLFDSGETAEATRL<br>KRTARRRYTRRKNRICYLQEIFSNEMAKVDDSFFHRLEESFLVEEDKKHERHPIFGNIVDEVAY<br>HEKYPTIYHLRKKLVDSTDKADLRLIYLALAHMIKFRGHFLIEGDLNPDNSDVDKLFIQLVQTY<br>NQLFEENPINASGVDAKAILSARLSKSRRLENLIAQLPGEKKNGLFGNLIALSLGLTPNFKSNF<br>DLAEDAKLQLSKDTYDDDLDNLLAQIGDQYADLFLAAKNLSDAILLSDILRVNTEITKAPLSAS<br>MIKRYDEHHQDLTLLKALVRQQLPEKYKEIFFDQSKNGYAGYIDGGASQEEFYKFIKPILEKMD<br>GTEELLVKLNREDLLRKQRTFDNGSIPHQIHLGELHAILRRQEDFYPFLKDNREKIEKILTFRI<br>PYYVGPLARGNSRFAWMTRKSEETITPWNFEEVVDKGASAQSFIERMTNFDKNLPNEKVLPKHS<br>LLYEYFTVYNELTKVKYVTEGMRKPAFLSGEQKKAIVDLLFKTNRKVTVKQLKEDYFKKIECFD<br>SVEISGVEDRFNASLGTYHDLLKIIKDKDFLDNEENEDILEDIVLTLTLFEDREMIEERLKTYA<br>HLFDDKVMKQLKRRRYTGWGRLSRKLINGIRDKQSGKTILDFLKSDGFANRNFMQLIHDDSLTF<br>KEDIQKAQVSGQGDSLHEHIANLAGSPAIKKGILQTVKVVDELVKVMGRHKPENIVIEMARENQ<br>TTQKGQKNSRERMKRIEEGIKELGSQILKEHPVENTQLQNEKLYLYYLQNGRDMYVDQELDINR<br>LSDYDVDAIVPQSFLKDDSIDNKVLTRSDKNRGKSDNVPSEEVVKKMKNYWRQLLNAKLITQRK<br>FDNLTKAERGGLSELDKAGFIKRQLVETRQITKHVAQILDSRMNTKYDENDKLIREVKVITLKS<br>KLVSDFRKDFQFYKVREINNYHHAHDAYLNAVVGTALIKKYPKLESEFVYGDYKVYDVRKMIAK<br>SEQEIGKATAKYFFYSNIMNFFKTEITLANGEIRKRPLIETNGETGEIVWDKGRDFATVRKVLS<br>MPQVNIVKKTEVQTGGFSKESILPKRNSDKLIARKKDWDPKKYGGFDSPTVAYSVLVVAKVEKG<br>KSKKLKSVKELLGITIMERSSFEKNPIDFLEAKGYKEVKKDLIIKLPKYSLFELENGRKRMLAS<br>AGELQKGNELALPSKYVNFLYLASHYEKLKGSPEDNEQKQLFVEQHKHYLDEIIEQISEFSKRV<br>ILADANLDKVLSAYNKHRDKPIREQAENIIHLFTLTNLGAPAAFKYFDTTIDRKRYTSTKEVLD<br>ATLIHQSITGLYETRIDLSQLGGDGSPKKKRKVSSDYKDHDGDYKDHDIDYKDDDDKAAGGGGS<br>LPTCSCLDRVIQKDKGPYYTHLGAGPSVAAVREIMENRYGQKGNAIRIEIVVYTGKEGKSSHGC<br>PIAKWVLRRSSDEEKVLCLVRQRTGHHCPTAVMVVLIMVWDGIPLPMADRLYTELTENLKSYNG<br>HPTDRRCTLNENRTCTCQGIDPETCGASFSFGCSWSMYFNGCKFGRSPSPRRFRIDPSSPLHEK<br>NLEDNLQSLATRLAPIYKQYAPVAYQNQVEYENVARECRLGSKEGRPFSGVTACLDFCAHPHRD<br>IHNMNNGSTVVCTLTREDNRSLGVIPQDEQLHVLPLYKLSDTDEFGSKEGMEAKIKSGAIEVLA<br>PRRKKRTCFTQPVPRSGKKRAAMMTEVLAHKIRAVEKKPIPRIKRKNNSTTTNNSKPSSLPTLG<br>SNTETVQPEVKSETEPHFILKSSDNTKTYSLMPSAPHPVKEASPGFSWSPKTASATPAPLKNDA<br>TASCGFSERSSTPHCTMPSGRLSGANAAAADGPGISQLGEVAPLPTLSAPVMEPLINSEPSTGV<br>TEPLTPHQPNHQPSFLTSPQDLASSPMEEDEQHSEADEPPSDEPLSDDPLSPAEEKLPHIDEYW<br>SDSEHIFLDANIGGVAIAPAHGSVLIECARRELHATTPVEHPNRNHPTRLSLVFYQHKNLNKPQ<br>HGFELNKIKFEAKEAKNKKMKASEQKDQAANEGPEQSSEVNELNQIPSHKALTLTHDNVVTVSP<br>YALTHVAGPYNHWV<br><br>(SEQ ID NO:113) |

box = nuclear localization signal
underline = triple flag tag
double underline = TET1CD

RNA-GUIDED TARGETING OF GENETIC AND EPIGENOMIC REGULATORY PROTEINS TO SPECIFIC GENOMIC LOCI

CLAIM OF PRIORITY

This application is a divisional of U.S. patent application Ser. No. 16/535,199, filed Aug. 8, 2019, which is a continuation of U.S. patent application Ser. No. 14/775,869, filed Sep. 14, 2015, now U.S. Pat. No. 10,378,027, which is a U.S. National Phase Application under 35 U.S.C. § 371 of International Patent Application No. PCT/US2014/027335, filed on Mar. 14, 2014, which claims the benefit of U.S. Patent Application Ser. Nos. 61/799,647, filed on Mar. 15, 2013; 61/838,178, filed on Jun. 21, 2013; 61/838,148, filed on Jun. 21, 2013; and 61/921,007, filed on Dec. 26, 2013. The entire contents of the foregoing are hereby incorporated by reference.

FEDERALLY SPONSORED RESEARCH OR DEVELOPMENT

This invention was made with Government support under Grant No. DP1GM105378 awarded by the National Institutes of Health and W911NF-11-2-0056 awarded by the Defense Advanced Research Projects Agency (DARPA) of the Department of Defense. The Government has certain rights in the invention.

SEQUENCE LISTING

This application contains a Sequence Listing that has been submitted electronically as an ASCII text file named "Sequence_Listing.txt." The ASCII text file, created on Oct. 5, 2021, is 133 KB in size. The material in the ASCII text file is hereby incorporated by reference in its entirety.

TECHNICAL FIELD

This invention relates to methods and constructs for RNA-guided targeting of genetic and epigenomic regulatory proteins, e.g., transcriptional activators, histone modification enzymes, DNA methylation modifiers, to specific genomic loci.

BACKGROUND

Clustered Regulatory Interspaced Short Palindromic Repeats (CRISPR), and CRISPR-associated (cas) genes, referred to as CRISPR/Cas systems, are used by various bacteria and archaea to mediate defense against viruses and other foreign nucleic acid. These systems use small RNAs to detect and silence foreign nucleic acids in a sequence-specific manner.

Three types of CRISPR/Cas systems have been described (Makarova et al., Nat. Rev. Microbiol. 9, 467 (2011); Makarova et al., Biol. Direct 1, 7 (2006); Makarova et al., Biol. Direct 6, 38 (2011)). Recent work has shown that Type II CRISPR/Cas systems can be engineered to direct targeted double-stranded DNA breaks in vitro to specific sequences by using a single "guide RNA" with complementarity to the DNA target site and a Cas9 nuclease (Jinek et al., Science 2012; 337:816-821). This targetable Cas9-based system also works in cultured human cells (Mali et al., Science. 2013 Feb. 15; 339(6121):823-6; Cong et al., Science. 2013 Feb. 15; 339(6121):819-23) and in vivo in zebrafish (Hwang and Fu et al., Nat Biotechnol. 2013 March; 31(3):227-9) for inducing targeted alterations into endogenous genes.

SUMMARY

At least in part, the present invention is based on the development of a fusion protein including a heterologous functional domain (e.g., a transcriptional activation domain) fused to a Cas9 nuclease that has had its nuclease activity inactivated by mutations (also known as "dCas9"). While published studies have used guide RNAs to target catalytically active and inactive Cas9 nuclease proteins to specific genomic loci, no work has yet adapted the use of this system to recruit additional effector domains. This work also provides the first demonstration of an RNA-guided process that results in an increase (rather than a decrease) in the level of expression of a target gene.

In addition, the present disclosure provides the first demonstration that multiplex gRNAs can be used to bring multiple dCas9-VP64 fusions to a single promoter, thereby resulting in synergistic activation of transcription.

Thus, in a first aspect, the invention provides fusion proteins comprising a catalytically inactive CRISPR associated 9 (dCas9) protein linked to a heterologous functional domain (HFD) that modifies gene expression, histones, or DNA, e.g., transcriptional activation domain, transcriptional repressors (e.g., silencers such as Heterochromatin Protein 1 (HP1), e.g., HP1α or HP1β, or a transcriptional repression domain, e.g., Krueppel-associated box (KRAB) domain, ERF repressor domain (ERD), or mSin3A interaction domain (SID)), enzymes that modify the methylation state of DNA (e.g., DNA methyltransferase (DNMT) or Ten-Eleven Translocation (TET) proteins, e.g., TET1, also known as Tet Methylcytosine Dioxygenase 1), or enzymes that modify histone subunit (e.g., histone acetyltransferases (HAT), histone deacetylases (HDAC), or histone demethylases). In some embodiments, the heterologous functional domain is a transcriptional activation domain, e.g., a transcriptional activation domain from VP64 or NF-κB p65; an enzyme that catalyzes DNA demethylation, e.g., a TET; or histone modification (e.g., LSD1, histone methyltransferase, HDACs, or HATs) or a transcription silencing domain, e.g., from Heterochromatin Protein 1 (HP1), e.g., HP1α or HP1β; or a biological tether, e.g., CRISPR/Cas Subtype Ypest protein 4 (Csy4), MS2, or lambda N protein.

In some embodiments, the catalytically inactive Cas9 protein is from *S. pyogenes*.

In some embodiments, the catalytically inactive Cas9 protein comprises mutations at comprises mutations at D10, E762, H983, or D986; and at H840 or N863, e.g., at D10 and H840, e.g., D10A or D10N and H840A or H840N or H840Y.

In some embodiments, the heterologous functional domain is linked to the N terminus or C terminus of the catalytically inactive Cas9 protein, with an optional intervening linker, wherein the linker does not interfere with activity of the fusion protein.

In some embodiments, the fusion protein includes one or both of a nuclear localization sequence and one or more epitope tags, e.g., c-myc, 6His, or FLAG tags, on the N-terminus, C-terminus, or in between the catalytically inactive CRISPR associated 9 (Cas9) protein and the heterologous functional domain, optionally with one or more intervening linkers.

In further aspect, the invention provides nucleic acids encoding the fusion proteins described herein, as well as expression vectors including the nucleic acids, and host cells expressing the fusion proteins.

In an additional aspect, the invention provides methods for increasing expression of a target gene in a cell. The methods include expressing a Cas9-HFD fusion protein as described herein in the cell, e.g., by contacting the cell with an expression vector including a sequence encoding the fusion protein, and also expressing in the cell one or more guide RNAs with complementarity directed to the target gene, e.g., by contacting the cell with one or more expression vectors comprising nucleic acid sequences encoding one or more guide RNAs.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing executed in color. Copies of this patent or patent application publication with color drawing(s) will be provided by the Office upon request and payment of the necessary fee.

FIG. 4 is an exemplary sequence of an sgRNA expression vector.

FIG. 5 is an exemplary sequence of CMV-T7-Cas9 D10A/H840A-3XFLAG-VP64 expression vector.

FIG. 6 is an exemplary sequence of CMV-T7-Cas9 recoded D10A/H840A-3XFLAG-VP64 expression vector.

FIG. 7 is an exemplary sequence of a Cas9-HFD, i.e., a Cas9-activator. An optional 3xFLAG sequence is underlined; the nuclear localization signal PKKKRKVS (SEQ ID NO:11) is in lower case; two linkers are in bold; and the VP64 transcriptional activator sequence, DALDDFDLDMLGSDALDDFDLDMLGS-DALDDFDLDMLGSDALDDFDLDML (SEQ ID NO:12), is boxed.

FIGS. 8A-8B are exemplary sequences of (8A) dCas9-NLS-3XFLAG-HP1alpha and (8B) dCas9-NLS-3XFLAG-HP1beta. Box=nuclear localization signal; underline=triple flag tag; double underline=HP1alpha hinge and chromoshadow domains.

FIG. 9 is an exemplary sequence of dCas9-TET1.

DETAILED DESCRIPTION

Described herein are fusion proteins of a heterologous functional domain (e.g., a transcriptional activation domain) fused to a catalytically inactivated version of the Cas9 protein for the purpose of enabling RNA-guided targeting of these functional domains to specific genomic locations in cells and living organisms.

The CRISPR/Cas system has evolved in bacteria as a defense mechanism to protect against invading plasmids and viruses. Short protospacers, derived from foreign nucleic acid, are incorporated into CRISPR loci and subsequently transcribed and processed into short CRISPR RNAs (crRNAs). These crRNAs, complexed with a second tracrRNA, then use their sequence complementarity to the invading nucleic acid to guide Cas9-mediated cleavage, and consequent destruction of the foreign nucleic acid. In 2012, Doudna and colleagues demonstrated that a single guide RNA (sgRNA) composed of a fusion of a crRNA with tracrRNA can mediate recruitment of Cas9 nuclease to specific DNA sequences in vitro (FIG. 1C; Jinek et al., Science 2012).

Figure 1A:
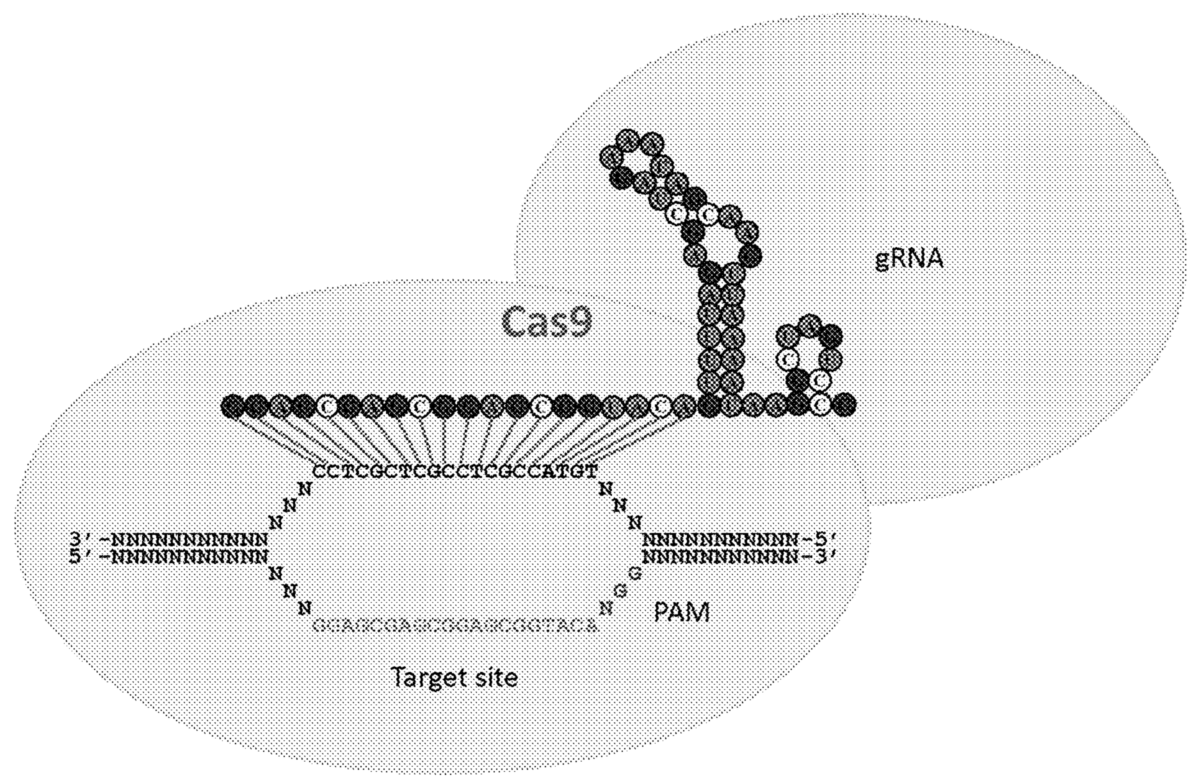
FIG. 1A is a schematic illustration showing a single guide RNA (sgRNA) recruiting Cas9 nuclease to a specific DNA sequence and thereby introducing targeted alterations. The sequence of the guide RNA shown is (SEQ ID NO: 9)
GGAGCGAGCGGAGCGGUACAGUUUUAGAGCUAGAAAUAGCAAGUUAAAA
UAAGGCUAGUCCG
Figure 1B:
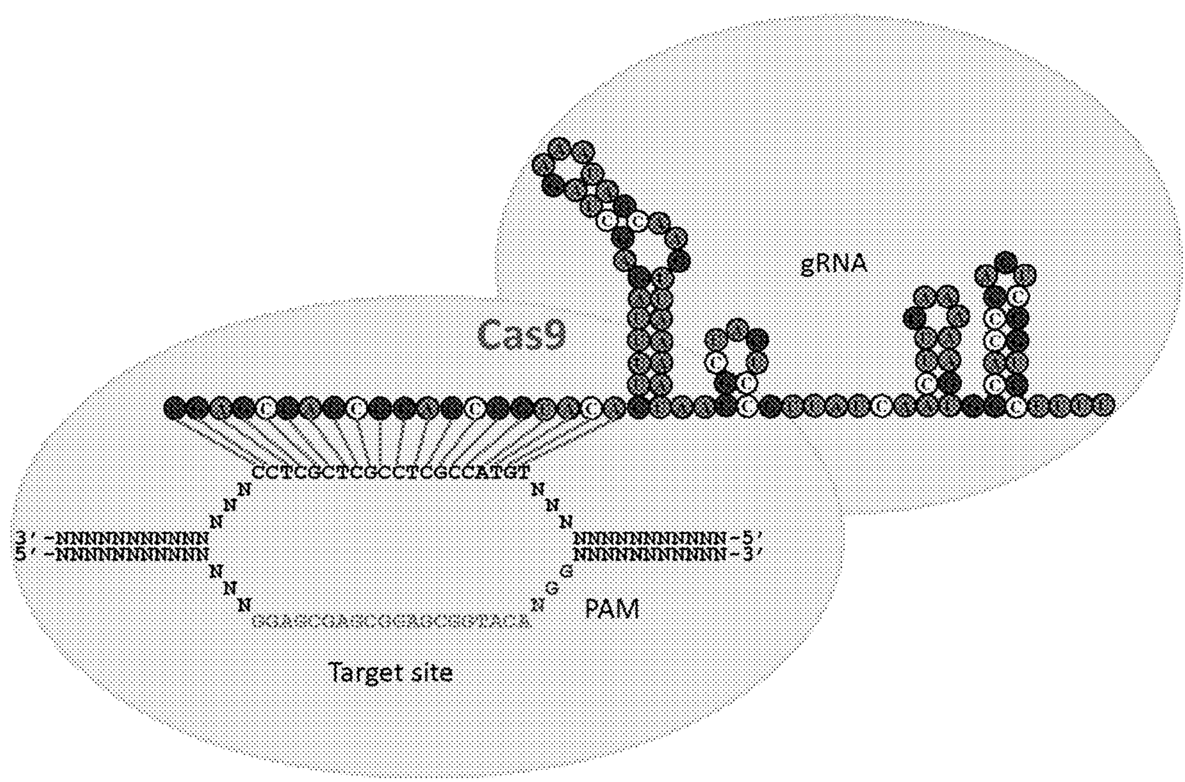
FIG. 1B is a schematic illustration showing a longer version of the sgRNA used to recruit Cas9 nuclease to a specific DNA sequence and to thereby introduce targeted alterations. The sequence of the guide RNA shown is (SEQ ID NO: 10)
GGAGCGAGCGGAGCGGUACAGUUUUAGAGCUAGAAAUAGCAAGUUAAAA
UAAGGCUAGUCCGUUAUCAACUUGAAAAAGUGGCACCGAGUCGGUGCUU
UU.

More recently, a longer version of the sgRNA has been used to introduce targeted alterations in human cells and zebrafish (FIG. 1B; Mali et al. Science 2013, Hwang and Fu et al., Nat Biotechnol. 2013 March; 31(3):227-9). Qi et al. demonstrated that gRNA-mediated recruitment of a catalytically inactive mutant form of Cas9 (referred to as dCas9) could lead to repression of specific endogenous genes in *E. coli* as well as of an EGFP reporter gene in human cells (Qi et al., Cell 152, 1173-1183 (2013)). Although this study demonstrated the potential to adapt RNA-guided Cas9 technology for regulation of gene expression, it did not test or demonstrate whether heterologous functional domains (e.g.—transcriptional activation domains) could be fused to dCas9 without disrupting its ability to be recruited to specific genomic sites by programmable sgRNAs or dual gRNAs (dgRNAs—i.e.—a customized crRNA and a tracrRNA).

Figure 1C:
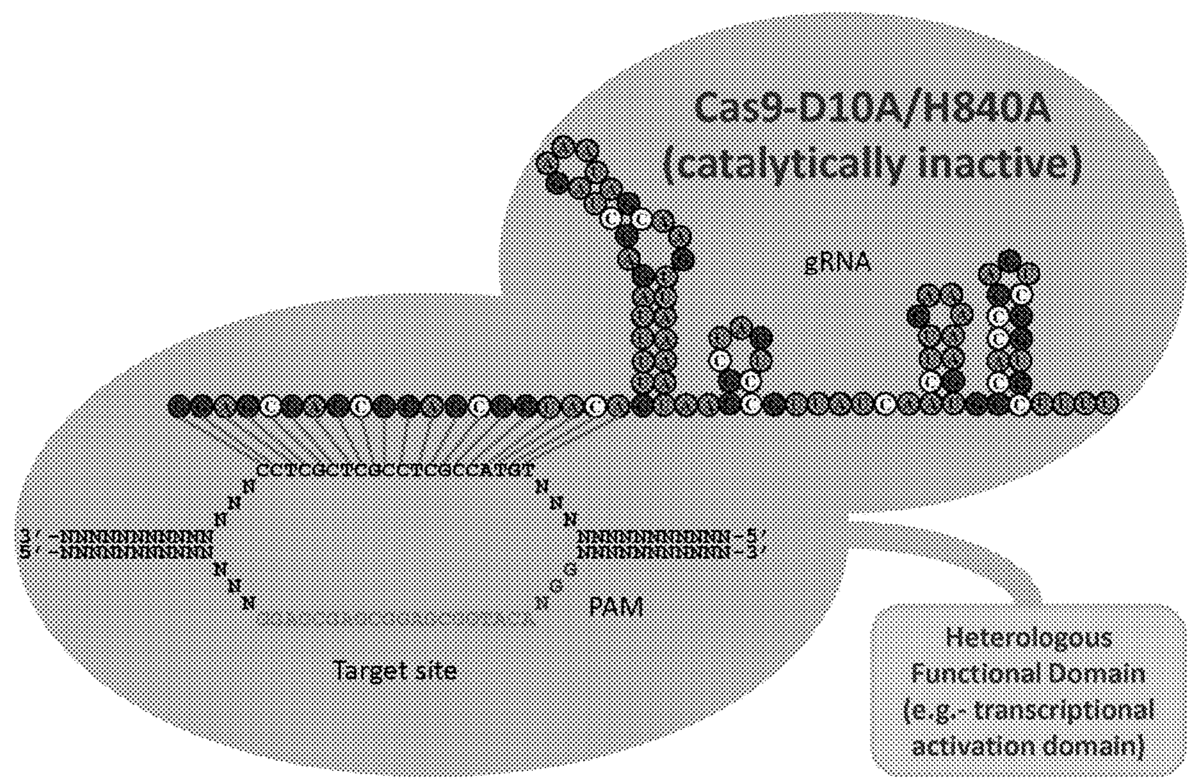
FIG. 1C is a schematic illustration showing a Cas9 protein containing D10A and H840A mutations to render the nuclease portion of the protein catalytically inactive, fused to a transcriptional activation domain and recruited to a specific DNA sequence by a sgRNA. The sequence of the guide RNA shown is (SEQ ID NO: 10)
GGAGCGAGCGGAGCGGUACAGUUUUAGAGCUAGAAAUAGCAAGUUAAAA
UAAGGCUAGUCCGUUAUCAACUUGAAAAAGUGGCACCGAGUCGGUGCUU
UU.

As described herein, in addition to guiding Cas9-mediated nuclease activity, it is possible to use CRISPR-derived RNAs to target heterologous functional domains fused to Cas9 (Cas9-HFD) to specific sites in the genome (FIG. 1C). For example, as described herein, it is possible to use single guide RNAs (sgRNAs) to target Cas9-HFD, e.g., Cas9-transcriptional activators (hereafter referred to as Cas9-activators) to the promoters of specific genes and thereby increase expression of the target gene. Thus Cas9-HFD can be localized to sites in the genome, with target specificity defined by sequence complementarity of the guide RNA. The target sequence also includes a PAM sequence (a 2-5 nucleotide sequence specified by the Cas9 protein which is adjacent to the sequence specified by the RNA).

The Cas9-HFD are created by fusing a heterologous functional domain (e.g., a transcriptional activation domain, e.g., from VP64 or NF-κB p65), to the N-terminus or C-terminus of a catalytically inactive Cas9 protein.

Cas9

A number of bacteria express Cas9 protein variants. The Cas9 from *Streptococcus pyogenes* is presently the most commonly used; some of the other Cas9 proteins have high levels of sequence identity with the *S. pyogenes* Cas9 and use the same guide RNAs. Others are more diverse, use different gRNAs, and recognize different PAM sequences as well (the 2-5 nucleotide sequence specified by the protein which is adjacent to the sequence specified by the RNA). Chylinski et al. classified Cas9 proteins from a large group of bacteria (RNA Biology 10:5, 1-12; 2013), and a large number of Cas9 proteins are listed in supplementary FIG. 1 and supplementary table 1 thereof, which are incorporated by reference herein. Additional Cas9 proteins are described in Esvelt et al., Nat Methods. 2013 November; 10(11):1116-21 and Fonfara et al., "Phylogeny of Cas9 determines functional exchangeability of dual-RNA and Cas9 among orthologous type II CRISPR-Cas systems." Nucleic Acids Res. 2013 Nov. 22. [Epub ahead of print] doi:10.1093/nar/gkt1074.

Cas9 molecules of a variety of species can be used in the methods and compositions described herein. While the *S. pyogenes* and *S. thermophilus* Cas9 molecules are the subject of much of the disclosure herein, Cas9 molecules of, derived from, or based on the Cas9 proteins of other species listed herein can be used as well. In other words, while the much of the description herein uses *S. pyogenes* and *S. thermophilus* Cas9 molecules, Cas9 molecules from the other species can replace them. Such species include those set forth in the following table, which was created based on supplementary FIG. 1 of Chylinski et al., 2013.

Alternative Cas9 proteins

| GenBank Acc No. | Bacterium |
|---|---|
| 303229466 | *Veillonella atypica* ACS-134-V-Col7a |
| 34762592 | *Fusobacterium nucleatum* subsp. *vincentii* |
| 374307738 | *Filifactor alocis* ATCC 35896 |
| 320528778 | *Solobacterium moorei* F0204 |
| 291520705 | *Coprococcus catus* GD-7 |
| 42525843 | *Treponema denticola* ATCC 35405 |
| 304438954 | *Peptoniphilus duerdenii* ATCC BAA-1640 |
| 224543312 | *Catenibacterium mitsuokai* DSM 15897 |
| 24379809 | *Streptococcus mutans* UA159 |
| 15675041 | *Streptococcus pyogenes* SF370 |
| 16801805 | *Listeria innocua* Clip11262 |
| 116628213 | *Streptococcus thermophilus* LMD-9 |
| 323463801 | *Staphylococcus pseudintermedius* ED99 |
| 352684361 | *Acidaminococcus intestini* RyC-MR95 |
| 302336020 | *Olsenella uli* DSM 7084 |
| 366983953 | *Oenococcus kitaharae* DSM 17330 |
| 310286728 | *Bifidobacterium bifidum* S17 |
| 258509199 | *Lactobacillus rhamnosus* GG |
| 300361537 | *Lactobacillus gasseri* JV-V03 |
| 169823755 | *Finegoldia magna* ATCC 29328 |
| 47458868 | *Mycoplasma mobile* 163K |
| 284931710 | *Mycoplasma gallisepticum* str. F |
| 363542550 | *Mycoplasma ovipneumoniae* SC01 |
| 384393286 | *Mycoplasma canis* PG 14 |
| 71894592 | *Mycoplasma synoviae* 53 |
| 238924075 | *Eubacterium rectale* ATCC 33656 |
| 116627542 | *Streptococcus thermophilus* LMD-9 |
| 315149830 | *Enterococcus faecalis* TX0012 |
| 315659848 | *Staphylococcus lugdunensis* M23590 |
| 160915782 | *Eubacterium dolichum* DSM 3991 |
| 336393381 | *Lactobacillus coryniformis* subsp. *torquens* |
| 310780384 | *Ilyobacter polytropus* DSM 2926 |
| 325677756 | *Ruminococcus albus* 8 |
| 187736489 | *Akkermansia muciniphila* ATCC BAA-835 |
| 117929158 | *Acidothermus cellulolyticus* 11B |
| 189440764 | *Bifidobacterium longum* DJO10A |
| 283456135 | *Bifidobacterium dentium* Bd1 |
| 38232678 | *Corynebacterium diphtheriae* NCTC 13129 |
| 187250660 | *Elusimicrobium minutum* Pei191 |
| 319957206 | *Nitratifractor salsuginis* DSM 16511 |
| 325972003 | *Sphaerochaeta globus* str. Buddy |
| 261414553 | *Fibrobacter succinogenes* subsp. *succinogenes* |
| 60683389 | *Bacteroides fragilis* NCTC 9343 |
| 256819408 | *Capnocytophaga ochracea* DSM 7271 |
| 90425961 | *Rhodopseudomonas palustris* BisB18 |
| 373501184 | *Prevotella micans* F0438 |
| 294674019 | *Prevotella ruminicola* 23 |
| 365959402 | *Flavobacterium columnare* ATCC 49512 |
| 312879015 | *Aminomonas paucivorans* DSM 12260 |
| 83591793 | *Rhodospirillum rubrum* ATCC 11170 |
| 294086111 | *Candidatus Puniceispirillum marinum* IMCC1322 |
| 121608211 | *Verminephrobacter eiseniae* EF01-2 |
| 344171927 | *Ralstonia syzygii* R24 |
| 159042956 | *Dinoroseobacter shibae* DFL 12 |
| 288957741 | *Azospirillum* sp- B510 |
| 92109262 | *Nitrobacter hamburgensis* X14 |
| 148255343 | *Bradyrhizobium* sp- BTAi1 |
| 34557790 | *Wolinella succinogenes* DSM 1740 |
| 218563121 | *Campylobacter jejuni* subsp. *jejuni* |
| 291276265 | *Helicobacter mustelae* 12198 |
| 229113166 | *Bacillus cereus* Rock1-15 |
| 222109285 | *Acidovorax ebreus* TPSY |
| 189485225 | uncultured Termite group 1 |
| 182624245 | *Clostridium perfringens* D str. |
| 220930482 | *Clostridium cellulolyticum* H10 |
| 154250555 | *Parvibaculum lavamentivorans* DS-1 |
| 257413184 | *Roseburia intestinalis* L1-82 |
| 218767588 | *Neisseria meningitidis* Z2491 |
| 15602992 | *Pasteurella multocida* subsp. *multocida* |
| 319941583 | *Sutterella wadsworthensis* 3 1 |
| 254447899 | *gamma proteobacterium* HTCC5015 |
| 54296138 | *Legionella pneumophila* str. Paris |
| 331001027 | *Parasutterella excrementihominis* YIT 11859 |
| 34557932 | *Wolinella succinogenes* DSM 1740 |
| 118497352 | *Francisella novicida* U112 |

The constructs and methods described herein can include the use of any of those Cas9 proteins, and their corresponding guide RNAs or other guide RNAs that are compatible. The Cas9 from *Streptococcus thermophilus* LMD-9 CRISPR1 system has been shown to function in human cells in Cong et al (Science 339, 819 (2013)). Additionally, Jinek et al. showed in vitro that Cas9 orthologs from *S. thermophilus* and *L. innocua*, (but not from *N. meningitidis* or *C. jejuni*, which likely use a different guide RNA), can be guided by a dual *S. pyogenes* gRNA to cleave target plasmid DNA, albeit with slightly decreased efficiency.

In some embodiments, the present system utilizes the Cas9 protein from *S. pyogenes*, either as encoded in bacteria or codon-optimized for expression in mammalian cells, containing mutations at D10, E762, H983, or D986 and H840 or N863, e.g., D10A/D10N and H840A/H840N/H840Y, to render the nuclease portion of the protein catalytically inactive; substitutions at these positions could be alanine (as they are in Nishimasu al., Cell 156, 935-949 (2014)) or they could be other residues, e.g., glutamine, asparagine, tyrosine, serine, or aspartate, e.g., E762Q, H983N, H983Y, D986N, N863D, N863S, or N863H (FIG. 1C). The sequence of the catalytically inactive *S. pyogenes* Cas9 that can be used in the methods and compositions described herein is as follows; the exemplary mutations of D10A and H840A are in bold and underlined.

```
                                                    (SEQ ID NO: 13)
         10         20         30         40         50         60
MDKKYSIGLA IGTNSVGWAV ITDEYKVPSK KFKVLGNTDR HSIKKNLIGA LLFDSGETAE

         70         80         90        100        110        120
ATRLKRTARR RYTRRKNRIC YLQEIFSNEM AKVDDSFFHR LEESFLVEED KKHERHPIFG

        130        140        150        160        170        180
NIVDEVAYHE KYPTIYHLRK KLVDSTDKAD LRLIYLALAH MIKFRGHFLI EGDLNPDNSD

        190        200        210        220        230        240
VDKLFIQLVQ TYNQLFEENP INASGVDAKA ILSARLSKSR RLENLIAQLP GEKKNGLFGN

        250        260        270        280        290        300
LIALSLGLTP NFKSNFDLAE DAKLQLSKDT YDDDLDNLLA QIGDQYADLF LAAKNLSDAI
```

-continued

```
       310        320        330        340        350        360
LLSDILRVNT EITKAPLSAS MIKRYDEHHQ DLTLLKALVR QQLPEKYKEI FFDQSKNGYA

       370        380        390        400        410        420
GYIDGGASQE EFYKFIKPIL EKMDGTEELL VKLNREDLLR KQRTFDNGSI PHQIHLGELH

       430        440        450        460        470        480
AILRRQEDFY PFLKDNREKI EKILTFRIPY YVGPLARGNS RFAWMTRKSE ETITPWNFEE

       490        500        510        520        530        540
VVDKGASAQS FIERMTNFDK NLPNEKVLPK HSLLYEYFTV YNELTKVKYV TEGMRKPAFL

       550        560        570        580        590        600
SGEQKKAIVD LLFKTNRKVT VKQLKEDYFK KIECFDSVEI SGVEDRFNAS LGTYHDLLKI

       610        620        630        640        650        660
IKDKDFLDNE ENEDILEDIV LTLTLFEDRE MIEERLKTYA HLFDDKVMKQ LKRRRYTGWG

       670        680        690        700        710        720
RLSRKLINGI RDKQSGKTIL DFLKSDGFAN RNFMQLIHDD SLTFKEDIQK AQVSGQGDSL

       730        740        750        760        770        780
HEHIANLAGS PAIKKGILQT VKVVDELVKV MGRHKPENIV IEMARENQTT QKGQKNSRER

       790        800        810        820        830        840
MKRIEEGIKE LGSQILKEHP VENTQLQNEK LYLYYLQNGR DMYVDQELDI NRLSDYDVDA

       850        860        870        880        890        900
IVPQSFLKDD SIDNKVLTRS DKNRGKSDNV PSEEVVKKMK NYWRQLLNAK LITQRKFDNL

       910        920        930        940        950        960
TKAERGGLSE LDKAGFIKRQ LVETRQITKH VAQILDSRMN TKYDENDKLI REVKVITLKS

       970        980        990       1000       1010       1020
KLVSDFRKDF QFYKVREINN YHHAHDAYLN AVVGTALIKK YPKLESEFVY GDYKVYDVRK

      1030       1040       1050       1060       1070       1080
MIAKSEQEIG KATAKYFFYS NIMNFFKTEI TLANGEIRKR PLIETNGETG EIVWDKGRDF

      1090       1100       1110       1120       1130       1140
ATVRKVLSMP QVNIVKKTEV QTGGFSKESI LPKRNSDKLI ARKKDWDPKK YGGFDSPTVA

      1150       1160       1170       1180       1190       1200
YSVLVVAKVE KGKSKKLKSV KELLGITIME RSSFEKNPID FLEAKGYKEV KKDLIIKLPK

      1210       1220       1230       1240       1250       1260
YSLFELENGR KRMLASAGEL QKGNELALPS KYVNFLYLAS HYEKLKGSPE DNEQKQLFVE

      1270       1280       1290       1300       1310       1320
QHKHYLDEII EQISEFSKRV ILADANLDKV LSAYNKHRDK PIREQAENII HLFTLTNLGA

      1330       1340       1350       1360
PAAFKYFDTT IDRKRYTSTK EVLDATLIHQ SITGLYETRI DLSQLGGD
```

In some embodiments, the Cas9 nuclease used herein is at least about 50% identical to the sequence of *S. pyogenes* Cas9, i.e., at least 50% identical to SEQ ID NO:13. In some embodiments, the nucleotide sequences are about 50%, 55%, 60%, 65%, 70%, 75%, 80%, 85%, 90%, 95%, 99% or 100% identical to SEQ ID NO:13.

In some embodiments, the catalytically inactive Cas9 used herein is at least about 50% identical to the sequence of the catalytically inactive *S. pyogenes* Cas9, i.e., at least 50%, 55%, 60%, 65%, 70%, 75%, 80%, 85%, 90%, 95%, 99% or 100% identical to SEQ ID NO:13, wherein the mutations at D10 and H840, e.g., D10A/D10N and H840A/H840N/H840Y are maintained.

In some embodiments, any differences from SEQ ID NO:13 are in non-conserved regions, as identified by sequence alignment of sequences set forth in Chylinski et al., RNA Biology 10:5, 1-12; 2013 (e.g., in supplementary FIG. 1 and supplementary table 1 thereof); Esvelt et al., Nat Methods. 2013 November; 10(11):1116-21 and Fonfara et al., Nucl. Acids Res. (2014) 42 (4): 2577-2590. [Epub ahead of print 2013 Nov. 22] doi:10.1093/nar/gkt1074, and wherein the mutations at D10 and H840, e.g., D10A/D10N and H840A/H840N/H840Y are maintained.

To determine the percent identity of two sequences, the sequences are aligned for optimal comparison purposes (gaps are introduced in one or both of a first and a second amino acid or nucleic acid sequence as required for optimal alignment, and non-homologous sequences can be disregarded for comparison purposes). The length of a reference sequence aligned for comparison purposes is at least 50% (in some embodiments, about 50%, 55%, 60%, 65%, 70%, 75%, 85%, 90%, 95%, or 100% of the length of the reference sequence) is aligned. The nucleotides or residues at corresponding positions are then compared. When a position in the first sequence is occupied by the same nucleotide or residue as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. For purposes of the present application, the percent identity between two amino acid sequences is determined using the Needleman and Wunsch ((1970) J. Mol. Biol. 48:444-453) algorithm which has been incorporated into the GAP program in the GCG software package, using a Blossum 62 scoring matrix with a gap penalty of 12, a gap extend penalty of 4, and a frameshift gap penalty of 5.

Heterologous Functional Domains

The transcriptional activation domains can be fused on the N or C terminus of the Cas9. In addition, although the present description exemplifies transcriptional activation domains, other heterologous functional domains (e.g., transcriptional repressors (e.g., KRAB, ERD, SID, and others, e.g., amino acids 473-530 of the ets2 repressor factor (ERF) repressor domain (ERD), amino acids 1-97 of the KRAB domain of KOX1, or amino acids 1-36 of the Mad mSIN3 interaction domain (SID); see Beerli et al., PNAS USA 95:14628-14633 (1998)) or silencers such as Heterochromatin Protein 1 (HP1, also known as swi6), e.g., HP1$\alpha$ or HP1$\beta$; proteins or peptides that could recruit long non-coding RNAs (lncRNAs) fused to a fixed RNA binding sequence such as those bound by the MS2 coat protein, endoribonuclease Csy4, or the lambda N protein; enzymes that modify the methylation state of DNA (e.g., DNA methyltransferase (DNMT) or TET proteins); or enzymes that modify histone subunits (e.g., histone acetyltransferases (HAT), histone deacetylases (HDAC), histone methyltransferases (e.g., for methylation of lysine or arginine residues) or histone demethylases (e.g., for demethylation of lysine or arginine residues)) as are known in the art can also be used. A number of sequences for such domains are known in the art, e.g., a domain that catalyzes hydroxylation of methylated cytosines in DNA. Exemplary proteins include the Ten-Eleven-Translocation (TET)1-3 family, enzymes that converts 5-methylcytosine (5-mC) to 5-hydroxymethylcytosine (5-hmC) in DNA.

Sequences for human TET1-3 are known in the art and are shown in the following table:

| | GenBank Accession Nos. | |
|---|---|---|
| Gene | Amino Acid | Nucleic Acid |
| TET1 | NP_085128.2 | NM_030625.2 |
| TET2* | NP_001120680.1 (var 1) | NM_001127208.2 |
| | NP_060098.3 (var2) | NM_017628.4 |
| TET3 | NP_659430.1 | NM_144993.1 |

*Variant (1) represents the longer transcript and encodes the longer isoform (a). Variant (2) differs in the 5' UTR and in the 3' UTR and coding sequence compared to variant 1. The resulting isoform (b) is shorter and has a distinct C-terminus compared to isoform a.

In some embodiments, all or part of the full-length sequence of the catalytic domain can be included, e.g., a catalytic module comprising the cysteine-rich extension and the 2OGFeDO domain encoded by 7 highly conserved exons, e.g., the Tet1 catalytic domain comprising amino acids 1580-2052, Tet2 comprising amino acids 1290-1905 and Tet3 comprising amino acids 966-1678. See, e.g., FIG. 1 of Iyer et al., Cell Cycle. 2009 Jun. 1; 8(11):1698-710. Epub 2009 Jun. 27, for an alignment illustrating the key catalytic residues in all three Tet proteins, and the supplementary materials thereof (available at ftp site ftp.ncbi.nih.gov/pub/aravind/DONS/supplementary material DONS.html) for full length sequences (see, e.g., seq 2c); in some embodiments, the sequence includes amino acids 1418-2136 of Tet1 or the corresponding region in Tet2/3.

Other catalytic modules can be from the proteins identified in Iyer et al., 2009.

In some embodiments, the heterologous functional domain is a biological tether, and comprises all or part of (e.g., DNA binding domain from) the MS2 coat protein, endoribonuclease Csy4, or the lambda N protein. These proteins can be used to recruit RNA molecules containing a specific stem-loop structure to a locale specified by the dCas9 gRNA targeting sequences. For example, a dCas9 fused to MS2 coat protein, endoribonuclease Csy4, or lambda N can be used to recruit a long non-coding RNA (lncRNA) such as XIST or HOTAIR; see, e.g., Keryer-Bibens et al., Biol. Cell 100:125-138 (2008), that is linked to the Csy4, MS2 or lambda N binding sequence. Alternatively, the Csy4, MS2 or lambda N protein binding sequence can be linked to another protein, e.g., as described in Keryer-Bibens et al., supra, and the protein can be targeted to the dCas9 binding site using the methods and compositions described herein. In some embodiments, the Csy4 is catalytically inactive.

In some embodiments, the fusion proteins include a linker between the dCas9 and the heterologous functional domains. Linkers that can be used in these fusion proteins (or between fusion proteins in a concatenated structure) can include any sequence that does not interfere with the function of the fusion proteins. In preferred embodiments, the linkers are short, e.g., 2-20 amino acids, and are typically flexible (i.e., comprising amino acids with a high degree of freedom such as glycine, alanine, and serine). In some embodiments, the linker comprises one or more units consisting of GGGS (SEQ ID NO:14) or GGGGS (SEQ ID NO:15), e.g., two, three, four, or more repeats of the GGGS (SEQ ID NO:14) or GGGGS (SEQ ID NO:15) unit. Other linker sequences can also be used.

Methods of Use

The described Cas9-HFD system is a useful and versatile tool for modifying the expression of endogenous genes. Current methods for achieving this require the generation of novel engineered DNA-binding proteins (such as engineered zinc finger or transcription activator-like effector DNA binding domains) for each site to be targeted. Because these methods demand expression of a large protein specifically engineered to bind each target site, they are limited in their capacity for multiplexing. Cas9-HFD, however, require expression of only a single Cas9-HFD protein, which can be targeted to multiple sites in the genome by expression of multiple short gRNAs. This system could therefore easily be used to simultaneously induce expression of a large number of genes or to recruit multiple Cas9-HFDs to a single gene, promoter, or enhancer. This capability will have broad utility, e.g., for basic biological research, where it can be used to study gene function and to manipulate the expression of multiple genes in a single pathway, and in synthetic biology, where it will enable researchers to create circuits in cell that are responsive to multiple input signals. The relative ease with which this technology can be implemented and adapted to multiplexing will make it a broadly useful technology with many wide-ranging applications.

The methods described herein include contacting cells with a nucleic acid encoding the Cas9-HFD described herein, and nucleic acids encoding one or more guide RNAs directed to a selected gene, to thereby modulate expression of that gene.

Guide RNAs (gRNAs)

Guide RNAs generally speaking come in two different systems: System 1, which uses separate crRNA and tracrRNAs that function together to guide cleavage by Cas9, and System 2, which uses a chimeric crRNA-tracrRNA hybrid that combines the two separate guide RNAs in a single system (referred to as a single guide RNA or sgRNA, see also Jinek et al., Science 2012; 337:816-821). The tracrRNA can be variably truncated and a range of lengths has been shown to function in both the separate system (system 1) and the chimeric gRNA system (system 2). For example, in some embodiments, tracrRNA may be truncated from its 3' end by at least 1, 2, 3, 4, 5, 6, 7, 8, 9, 10, 15, 20, 25, 30, 35 or 40 nts. In some embodiments, the tracrRNA molecule may be truncated from its 5' end by at least 1, 2, 3, 4, 5, 6, 7, 8, 9, 10, 15, 20, 25, 30, 35 or 40 nts. Alternatively, the tracrRNA molecule may be truncated from both the 5' and 3' end, e.g., by at least 1, 2, 3, 4, 5, 6, 7, 8, 9, 10, 15 or 20 nts on the 5' end and at least 1, 2, 3, 4, 5, 6, 7, 8, 9, 10, 15, 20, 25, 30, 35 or 40 nts on the 3' end. See, e.g., Jinek et al., Science 2012; 337:816-821; Mali et al., Science. 2013 Feb. 15; 339(6121):823-6; Cong et al., Science. 2013 Feb. 15; 339 (6121):819-23; and Hwang and Fu et al., Nat Biotechnol. 2013 March; 31(3):227-9; Jinek et al., Elife 2, e00471 (2013)). For System 2, generally the longer length chimeric gRNAs have shown greater on-target activity but the relative specificities of the various length gRNAs currently remain undefined and therefore it may be desirable in certain instances to use shorter gRNAs. In some embodiments, the gRNAs are complementary to a region that is within about 100-800 bp upstream of the transcription start site, e.g., is within about 500 bp upstream of the transcription start site, includes the transcription start site, or within about 100-800 bp, e.g., within about 500 bp, downstream of the transcription start site. In some embodiments, vectors (e.g., plasmids) encoding more than one gRNA are used, e.g., plasmids encoding, 2, 3, 4, 5, or more gRNAs directed to different sites in the same region of the target gene.

Cas9 nuclease can be guided to specific 17-20 nt genomic targets bearing an additional proximal protospacer adjacent motif (PAM), e.g., of sequence NGG using a guide RNA, e.g., a single gRNA or a tracrRNA/crRNA, bearing 17-20 nts at its 5' end that are complementary to the complementary strand of the genomic DNA target site. Thus, the present methods can include the use of a single guide RNA comprising a crRNA fused to a normally trans-encoded tracrRNA, e.g., a single Cas9 guide RNA as described in Mali et al., Science 2013 Feb. 15; 339(6121):823-6, with a sequence at the 5' end that is complementary to the target sequence, e.g., of 25-17, optionally 20 or fewer nucleotides (nts), e.g., 20, 19, 18, or 17 nts, preferably 17 or 18 nts, of the complementary strand to a target sequence immediately 5' of a protospacer adjacent motif (PAM), e.g., NGG, NAG; or NNGG In some embodiments, the single Cas9 guide RNA consists of the sequence:

(SEQ ID NO: 1)
$(X_{17-20})$GUUUUAGAGCUAGAAAUAGCAAGUUAAAAUAAGGCUAGUCCG $(X_N)$;

(SEQ ID NO: 2)
$(X_{17-20})$GUUUUAGAGCUAUGCUGAAAAGCAUAGCAAGUUAAAAUAAGGC UAGUCCGUUAUC$(X_N)$;

(SEQ ID NO: 3)
$(X_{17-20})$GUUUUAGAGCUAUGCUGUUUUGGAAACAAAACAGCAUAGCAAG UUAAAAUAAGGCUAGUCCGUUAUC$(X_N)$;

-continued (SEQ ID NO: 4)
$(X_{17-20})$GUUUUAGAGCUAGAAAUAGCAAGUUAAAAUAAGGCUAGUCCGU UAUCAACUUGAAAAAGUGGCACCGAGUCGGUGC$(X_N)$, (SEQ ID NO: 5)
$(X_{17-20})$GUUUAAGAGCUAGAAAUAGCAAGUUUAAAUAAGGCUAGUCCGU UAUCAACUUGAAAAAGUGGCACCGAGUCGGUGC;

(SEQ ID NO: 6)
$(X_{17-20})$GUUUUAGAGCUAUGCUGGAAACAGCAUAGCAAGUUUAAAUAAG GCUAGUCCGUUAUCAACUUGAAAAAGUGGCACCGAGUCGGUGC;
or (SEQ ID NO: 7)
$(X_{17-20})$GUUUAAGAGCUAUGCUGGAAACAGCAUAGCAAGUUUAAAUAAG GCUAGUCCGUUAUCAACUUGAAAAAGUGGCACCGAGUCGGUGC;

wherein $X_{17-20}$ is the nucleotide sequence complementary to 17-20 consecutive nucleotides of the target sequence. DNAs encoding the single guide RNAs have been described previously in the literature (Jinek et al., Science. 337(6096): 816-21 (2012) and Jinek et al., Elife. 2:e00471 (2013)).

The guide RNAs can include $X_N$ which can be any sequence, wherein N (in the RNA) can be 0-200, e.g., 0-100, 0-50, or 0-20, that does not interfere with the binding of the ribonucleic acid to Cas9.

In some embodiments, the guide RNA includes one or more Adenine (A) or Uracil (U) nucleotides on the 3' end. In some embodiments the RNA includes one or more U, e.g., 1 to 8 or more Us (e.g., U, UU, UUU, UUUU, UUUUU, UUUUUU, UUUUUUU, UUUUUUUU) at the 3' end of the molecule, as a result of the optional presence of one or more Ts used as a termination signal to terminate RNA PolIII transcription.

Although some of the examples described herein utilize a single gRNA, the methods can also be used with dual gRNAs (e.g., the crRNA and tracrRNA found in naturally occurring systems). In this case, a single tracrRNA would be used in conjunction with multiple different crRNAs expressed using the present system, e.g., the following:
$(X_{17-20})$GUUUUAGAGCUA (SEQ ID NO:102);
$(X_{17-20})$ GUUUUAGAGCUAUGCUGUUUUG (SEQ ID NO:103); or
$(X_{17-20})$GUUUUAGAGCUAUGCU (SEQ ID NO:104); and a tracrRNA sequence. In this case, the crRNA is used as the guide RNA in the methods and molecules described herein, and the tracrRNA can be expressed from the same or a different DNA molecule. In some embodiments, the methods include contacting the cell with a tracrRNA comprising or consisting of the sequence GGAACCAUUCAAAACAG-CAUAGCAAGUUAAAAUAAGGCUAGU-CCGUUAUCA ACUUGAAAAAGUGGCACCGAGUCG-GUGC (SEQ ID NO:8) or an active portion thereof (an active portion is one that retains the ability to form complexes with Cas9 or dCas9). In some embodiments, the tracrRNA molecule may be truncated from its 3' end by at least 1, 2, 3, 4, 5, 6, 7, 8, 9, 10, 15, 20, 25, 30, 35 or 40 nts. In another embodiment, the tracrRNA molecule may be truncated from its 5' end by at least 1, 2, 3, 4, 5, 6, 7, 8, 9, 10, 15, 20, 25, 30, 35 or 40 nts. Alternatively, the tracrRNA molecule may be truncated from both the 5' and 3' end, e.g., by at least 1, 2, 3, 4, 5, 6, 7, 8, 9, 10, 15 or 20 nts on the 5' end and at least 1, 2, 3, 4, 5, 6, 7, 8, 9, 10, 15, 20, 25, 30, 35 or 40 nts on the 3' end.

Exemplary tracrRNA sequences in addition to SEQ ID NO:8 include the following:

UAGCAAGUUAAAAUAAGGCUAGUCCGUUAUCAACUUGAAAAAGUGGCACCG AGUCGGUGC (SEQ ID NO:105) or an active portion thereof; or AGCAUAGCAAGUUAAAAUAAGGCUAGUCCGUUAUCAACUUGAAAAAGUGGC ACCGAGUCGGUGC (SEQ ID NO:106) or an active portion thereof.

In some embodiments when $(X_{17-20})$GUUUUAGAGCUAUGCUGUUUUG (SEQ ID NO:102) is used as a crRNA, the following tracrRNA is used: GGAACCAUUCAAAACAGCAUAGCAAGUUAAAAUAAGGCUAGUCCGUUAUCA ACUUGAAAAAGUGGCACCGAGUCGGUGC (SEQ ID NO:8) or an active portion thereof.

In some embodiments when $(X_{17-20})$GUUUUAGAGCUA (SEQ ID NO:102) is used as a crRNA, the following tracrRNA is used: UAGCAAGUUAAAAUAAGGCUAGUCCGUUAUCAACUUGAAAAAGUGGCACCG AGUCGGUGC (SEQ ID NO:105) or an active portion thereof.

In some embodiments when $(X_{17-20})$ GUUUUAGAGCUAUGCU (SEQ ID NO:104) is used as a crRNA, the following tracrRNA is used: AGCAUAGCAAGUUAAAAUAAGGCUAGUCCGUUAUCAACUUGAAAAAGUGGC ACCGAGUCGGUGC (SEQ ID NO:106) or an active portion thereof.

In some embodiments, the gRNA is targeted to a site that is at least three or more mismatches different from any sequence in the rest of the genome in order to minimize off-target effects.

Modified RNA oligonucleotides such as locked nucleic acids (LNAs) have been demonstrated to increase the specificity of RNA-DNA hybridization by locking the modified oligonucleotides in a more favorable (stable) conformation. For example, 2'-O-methyl RNA is a modified base where there is an additional covalent linkage between the 2' oxygen and 4' carbon which when incorporated into oligonucleotides can improve overall thermal stability and selectivity (Formula I).

Formula I

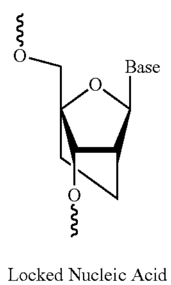

Locked Nucleic Acid

Thus in some embodiments, the tru-gRNAs disclosed herein may comprise one or more modified RNA oligonucleotides. For example, the truncated guide RNAs molecules described herein can have one, some or all of the region of the guideRNA complementary to the target sequence are modified, e.g., locked (2'-O-4'-C methylene bridge), 5'-methylcytidine, 2'-O-methyl-pseudouridine, or in which the ribose phosphate backbone has been replaced by a polyamide chain (peptide nucleic acid), e.g., a synthetic ribonucleic acid.

In other embodiments, one, some or all of the nucleotides of the tru-gRNA sequence may be modified, e.g., locked (2'-O-4'-C methylene bridge), 5'-methylcytidine, 2'-O-methyl-pseudouridine, or in which the ribose phosphate backbone has been replaced by a polyamide chain (peptide nucleic acid), e.g., a synthetic ribonucleic acid.

In some embodiments, the single guide RNAs and/or crRNAs and/or tracrRNAs can include one or more Adenine (A) or Uracil (U) nucleotides on the 3' end.

Existing Cas9-based RGNs use gRNA-DNA heteroduplex formation to guide targeting to genomic sites of interest. However, RNA-DNA heteroduplexes can form a more promiscuous range of structures than their DNA-DNA counterparts. In effect, DNA-DNA duplexes are more sensitive to mismatches, suggesting that a DNA-guided nuclease may not bind as readily to off-target sequences, making them comparatively more specific than RNA-guided nucleases. Thus, the guide RNAs usable in the methods described herein can be hybrids, i.e., wherein one or more deoxyribonucleotides, e.g., a short DNA oligonucleotide, replaces all or part of the gRNA, e.g., all or part of the complementarity region of a gRNA. This DNA-based molecule could replace either all or part of the gRNA in a single gRNA system or alternatively might replace all of part of the crRNA and/or tracrRNA in a dual crRNA/tracrRNA system. Such a system that incorporates DNA into the complementarity region should more reliably target the intended genomic DNA sequences due to the general intolerance of DNA-DNA duplexes to mismatching compared to RNA-DNA duplexes. Methods for making such duplexes are known in the art, See, e.g., Barker et al., BMC Genomics. 2005 Apr. 22; 6:57; and Sugimoto et al., Biochemistry. 2000 Sep. 19; 39(37):11270-81.

In addition, in a system that uses separate crRNA and tracrRNA, one or both can be synthetic and include one or more modified (e.g., locked) nucleotides or deoxyribonucleotides.

In a cellular context, complexes of Cas9 with these synthetic gRNAs could be used to improve the genome-wide specificity of the CRISPR/Cas9 nuclease system.

The methods described can include expressing in a cell, or contacting the cell with, a Cas9 gRNA plus a fusion protein as described herein.

Expression Systems

In order to use the fusion proteins and guide RNAs described herein, it may be desirable to express them from a nucleic acid that encodes them. This can be performed in a variety of ways. For example, a nucleic acid encoding a guide RNA or fusion protein can be cloned into an intermediate vector for transformation into prokaryotic or eukaryotic cells for replication and/or expression. Intermediate vectors are typically prokaryote vectors, e.g., plasmids, or shuttle vectors, or insect vectors, for storage or manipulation of the nucleic acid encoding the fusion protein or for production of the fusion protein. The nucleic acid encoding the guide RNA or fusion protein can also be cloned into an expression vector, for administration to a plant cell, animal cell, preferably a mammalian cell or a human cell, fungal cell, bacterial cell, or protozoan cell.

To obtain expression, a sequence encoding a guide RNA or fusion protein is typically subcloned into an expression vector that contains a promoter to direct transcription. Suitable bacterial and eukaryotic promoters are well known in the art and described, e.g., in Sambrook et al., Molecular Cloning, A Laboratory Manual (3d ed. 2001); Kriegler, Gene Transfer and Expression: A Laboratory Manual (1990); and Current Protocols in Molecular Biology (Ausubel et al., eds., 2010). Bacterial expression systems for expressing the engineered protein are available in, e.g., *E. coli, Bacillus* sp., and *Salmonella* (Palva et al., 1983, Gene 22:229-235). Kits for such expression systems are commercially available.

Eukaryotic expression systems for mammalian cells, yeast, and insect cells are well known in the art and are also commercially available.

The promoter used to direct expression of the nucleic acid depends on the particular application. For example, a strong constitutive promoter is typically used for expression and purification of fusion proteins. In contrast, when the fusion protein is to be administered in vivo for gene regulation, either a constitutive or an inducible promoter can be used, depending on the particular use of the fusion protein. In addition, a preferred promoter for administration of the fusion protein can be a weak promoter, such as HSV TK or a promoter having similar activity. The promoter can also include elements that are responsive to transactivation, e.g., hypoxia response elements, Gal4 response elements, lac repressor response element, and small molecule control systems such as tetracycline-regulated systems and the RU-486 system (see, e.g., Gossen & Bujard, 1992, Proc. Natl. Acad. Sci. USA, 89:5547; Oligino et al., 1998, Gene Ther., 5:491-496; Wang et al., 1997, Gene Ther., 4:432-441; Neering et al., 1996, Blood, 88:1147-55; and Rendahl et al., 1998, Nat. Biotechnol., 16:757-761).

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to the nucleic acid sequence encoding the fusion protein, and any signals required, e.g., for efficient polyadenylation of the transcript, transcriptional termination, ribosome binding sites, or translation termination. Additional elements of the cassette may include, e.g., enhancers, and heterologous spliced intronic signals.

The particular expression vector used to transport the genetic information into the cell is selected with regard to the intended use of the fusion protein, e.g., expression in plants, animals, bacteria, fungus, protozoa, etc. Standard bacterial expression vectors include plasmids such as pBR322 based plasmids, pSKF, pET23D, and commercially available tag-fusion expression systems such as GST and LacZ. A preferred tag-fusion protein is the maltose binding protein (MBP). Such tag-fusion proteins can be used for purification of the engineered TALE repeat protein. Epitope tags can also be added to recombinant proteins to provide convenient methods of isolation, for monitoring expression, and for monitoring cellular and subcellular localization, e.g., c-myc or FLAG Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

The vectors for expressing the guide RNAs can include RNA Pol III promoters to drive expression of the guide RNAs, e.g., the H1, U6 or 7SK promoters. These human promoters allow for expression of gRNAs in mammalian cells following plasmid transfection. Alternatively, a T7 promoter may be used, e.g., for in vitro transcription, and the RNA can be transcribed in vitro and purified. Vectors suitable for the expression of short RNAs, e.g., siRNAs, shRNAs, or other small RNAs, can be used.

Some expression systems have markers for selection of stably transfected cell lines such as thymidine kinase, hygromycin B phosphotransferase, and dihydrofolate reductase. High yield expression systems are also suitable, such as using a baculovirus vector in insect cells, with the fusion protein encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of recombinant sequences.

Standard transfection methods are used to produce bacterial, mammalian, yeast or insect cell lines that express large quantities of protein, which are then purified using standard techniques (see, e.g., Colley et al., 1989, J. Biol. Chem., 264:17619-22; Guide to Protein Purification, in Methods in Enzymology, vol. 182 (Deutscher, ed., 1990)). Transformation of eukaryotic and prokaryotic cells are performed according to standard techniques (see, e.g., Morrison, 1977, J. Bacteriol. 132:349-351; Clark-Curtiss & Curtiss, Methods in Enzymology 101:347-362 (Wu et al., eds, 1983).

Any of the known procedures for introducing foreign nucleotide sequences into host cells may be used. These include the use of calcium phosphate transfection, polybrene, protoplast fusion, electroporation, nucleofection, liposomes, microinjection, naked DNA, plasmid vectors, viral vectors, both episomal and integrative, and any of the other well-known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

In some embodiments, the fusion protein includes a nuclear localization domain which provides for the protein to be translocated to the nucleus. Several nuclear localization sequences (NLS) are known, and any suitable NLS can be used. For example, many NLSs have a plurality of basic amino acids, referred to as a bipartite basic repeats (reviewed in Garcia-Bustos et al, 1991, Biochim. Biophys. Acta, 1071:83-101). An NLS containing bipartite basic repeats can be placed in any portion of chimeric protein and results in the chimeric protein being localized inside the nucleus. In preferred embodiments a nuclear localization domain is incorporated into the final fusion protein, as the ultimate functions of the fusion proteins described herein will typically require the proteins to be localized in the nucleus. However, it may not be necessary to add a separate nuclear localization domain in cases where the DBD domain itself, or another functional domain within the final chimeric protein, has intrinsic nuclear translocation function.

The present invention includes the vectors and cells comprising the vectors.

EXAMPLES

The invention is further described in the following examples, which do not limit the scope of the invention described in the claims.

Example 1. Engineering CRISPR/Cas Activator System

Figure 1D:
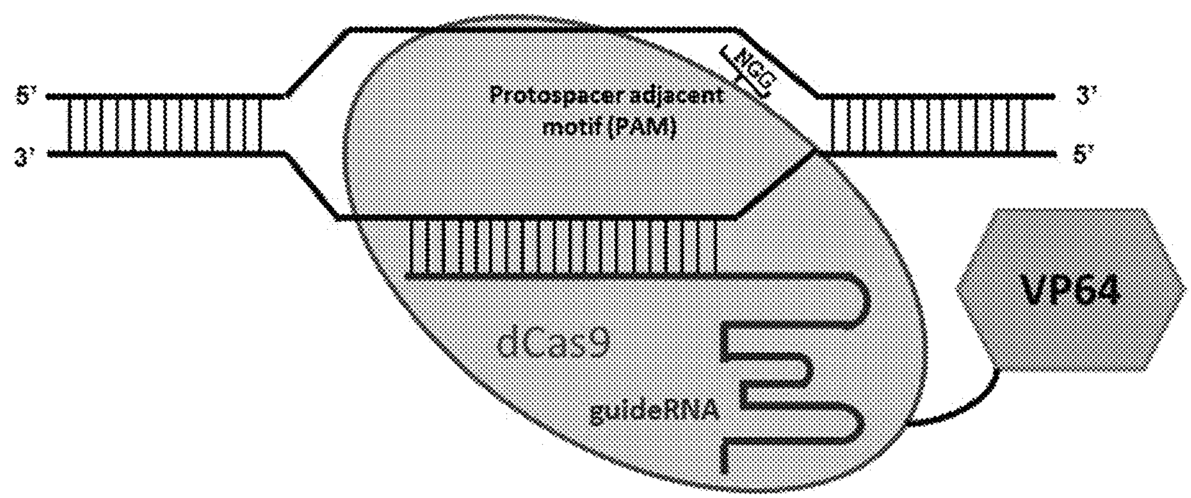
FIG. 1D is a schematic depicting recruitment of dCas9-VP64 fusion protein to a specific genomic target sequence by a chimeric sgRNA.

It was hypothesized that RNA-guided transcriptional activators could be created by fusing the strong synthetic VP64 activation domain (Beerli et al., Proc Natl Acad Sci USA 95, 14628-14633 (1998)) to the carboxy-terminus of the catalytically inactivated dCas9 protein (FIG. 1D).

To express guide RNAs (gRNAs) in human cells, a vector was engineered that would express the full length chimeric gRNA (a fusion of crRNA and tracrRNA originally described by Jinek et al. (Science 2012)) driven by a U6 promoter. Construction of the gRNA expression plasmids was performed as follows. Pairs of DNA oligonucleotides encoding the variable 20 nt gRNA targeting sequences were annealed together to generate short double-strand DNA fragments with 4 bp overhangs (Table 1).

TABLE 1

VEGFA and NTF3 gene target sites and associated oligonucleotides used to construct gRNA expression plasmids.

| gRNA | Target Site (including PAM) | SEQ ID NO: |
|---|---|---|
| V1 | GTGTGCAGACGGCAGTCACTAGG | 16. |
| V2 | GAGCAGCGTCTTCGAGAGTGAGG | 17. |
| V3 | GGTGAGTGAGTGTGTGCGTGTGG | 18. |
| V4 | GTTGGAGCGGGGAGAAGGCCAGG | 19. |
| V5 | GGGTGGGGGGAGTTTGCTCCTGG | 20. |
| V6 | GGCTTTGGAAAGGGGGTGGGGGG | 21. |
| V7 | GGGGCGGGGTCCCGGCGGGGCGG | 22. |
| V8 | GCTCGGAGGTCGTGGCGCTGGGG | 23. |
| V9 | GACTCACCGGCCAGGGCGCTCGG | 24. |
| V10 | GGCGCAGCGGTTAGGTGGACCGG | 25. |
| V11 | GGCGCATGGCTCCGCCCCGCCGG | 26. |
| V12 | GCCACGACCTCCGAGCTACCCGG | 27. |
| V13 | GCGGCGTGAGCCCTCCCCCTTGG | 28. |
| V14 | GGAGGCGGGGTGGAGGGGGTCGG | 29. |
| V15 | GGGCTCACGCCGCGCTCCGGCGG | 30. |
| V16 | GACCCCCTCCACCCCGCCTCCGG | 31. |
| N1 | GAGCGCGGAGCCATCTGGCCGGG | 32. |
| N2 | GCGCGGCGCGGAAGGGGTTAAGG | 33. |
| N3 | GCGGCGCGGCGCGGGCCGGCGGG | 34. |
| N4 | GCCGCGCCGCCCTCCCCCGCCGG | 35. |
| N5 | GCGGTTATAACCAGCCAACCCGG | 36. |
| N6 | GTGCGCGGAGCTGTTCGGAAGGG | 37. |
| **gRNA** | **top oligo** | **SEQ ID NO:** |
| V1 | ACACCGTGTGCAGACGGCAGTCACTG | 38. |
| V2 | ACACCGAGCAGCGTCTTCGAGAGTGG | 39. |
| V3 | ACACCGGTGAGTGAGTGTGTGCGTGG | 40. |
| V4 | ACACCGTTGGAGCGGGGAGAAGGCCG | 41. |
| V5 | ACACCGGGTGGGGGGAGTTTGCTCCG | 42. |
| V6 | ACACCGGCTTTGGAAAGGGGGTGGGG | 43. |

TABLE 1-continued

VEGFA and NTF3 gene target sites and associated oligonucleotides used to construct gRNA expression plasmids.

| gRNA | top oligo | SEQ ID NO: |
|---|---|---|
| V7 | ACACCGGGGCGGGGTCCCGGCGGGG | 44. |
| V8 | ACACCGCTCGGAGGTCGTGGCGCTGG | 45. |
| V9 | ACACCGACTCACCGGCCAGGGCGCTG | 46. |
| V10 | ACACCGGCGCAGCGGTTAGGTGGACG | 47. |
| V11 | ACACCGGCGCATGGCTCCGCCCCGCG | 48. |
| V12 | ACACCGCCACGACCTCCGAGCTACCG | 49. |
| V13 | ACACCGCGGCGTGAGCCCTCCCCCTG | 50. |
| V14 | ACACCGGAGGCGGGGTGGAGGGGGTG | 51. |
| V15 | ACACCGGGCTCACGCCGCGCTCCGGG | 52. |
| V16 | ACACCGACCCCCTCCACCCCGCCTCG | 53. |
| N1 | ACACCGAGCGCGGAGCCATCTGGCCG | 54. |
| N2 | ACACCGCGCGGCGCGGAAGGGGTTAG | 55. |
| N3 | ACACCGCGGCGCGGCGCGGGCCGGCG | 56. |
| N4 | ACACCGCCGCGCCGCCCTCCCCCGCG | 57. |
| N5 | ACACCGCGGTTATAACCAGCCAACCG | 58. |
| N6 | ACACCGTGCGCGGAGCTGTTCGGAAG | 59. |
| **gRNA** | **bottom oligo** | **SEQ ID NO:** |
| V1 | AAAACAGTGACTGCCGTCTGCACACG | 60. |
| V2 | AAAACCACTCTCGAAGACGCTGCTCG | 61. |
| V3 | AAAACCACGCACACACTCACTCACCG | 62. |
| V4 | AAAACGGCCTTCTCCCCGCTCCAACG | 63. |
| V5 | AAAACGGAGCAAACTCCCCCCACCCG | 64. |
| V6 | AAAACCCCACCCCCTTTCCAAAGCCG | 65. |
| V7 | AAAACCCCCGCCGGGACCCCGCCCCG | 66. |
| V8 | AAAACCAGCGCCACGACCTCCGAGCG | 67. |
| V9 | AAAACAGCGCCCTGGCCGGTGAGTCG | 68. |
| V10 | AAAACGTCCACCTAACCGCTGCGCCG | 69. |
| V11 | AAAACGCGGGGCGGAGCCATGCGCCG | 70. |
| V12 | AAAACGGTAGCTCGGAGGTCGTGGCG | 71. |
| V13 | AAAACAGGGGGAGGGCTCACGCCGCG | 72. |
| V14 | AAAACACCCCCTCCACCCCGCCTCCG | 73. |
| V15 | AAAACCCGGAGCGCGGCGTGAGCCCG | 74. |
| V16 | AAAACGAGGCGGGGTGGAGGGGGTCG | 75. |
| N1 | AAAACGGCCAGATGGCTCCGCGCTCG | 76. |
| N2 | AAAACTAACCCCTTCCGCGCCGCGCG | 77. |
| N3 | AAAACGCCGGCCCGCGCCGCGCCGCG | 78. |
| N4 | AAAACGCGGGGGAGGGCGGCGCGGCG | 79. |

TABLE 1-continued

| VEGFA and NTF3 gene target sites and associated oligonucleotides used to construct gRNA expression plasmids. | | |
|---|---|---|
| N5 | AAAACGGTTGGCTGGTTATAACCGCG | 80. |
| N6 | AAAACTTCCGAACAGCTCCGCGCACG | 81. |

These fragments were ligated into BsmBI-digested plasmid pMLM3636 to yield DNA encoding a chimeric ~102 nt single-chain guide RNA (Mali et al., Science. 2013 Feb. 15; 339(6121):823-6; Hwang et al., Nat Biotechnol. 2013 March; 31(3):227-9) expressed by a human U6 promoter. The pMLM3636 plasmid and its full DNA sequence are available from Addgene. See FIG. 4.

To engineer a Cas9-activator the D10A, H840A catalytic mutations (previously described in Jinek et al., 2012; and Qi et al., 2013) were introduced into either the wild-type or a codon-optimized Cas9 sequence (FIG. 5). These mutations render the Cas9 catalytically inactive so that it will no longer induce double-strand breaks. In one construct, a triple flag tag, nuclear localization signal and the VP64 activation domain were fused to the C-terminus of the inactive Cas9 (FIG. 6). Expression of this fusion protein was driven by the CMV promoter.

Construction of dCas-VP64 expression plasmids was performed as follows. DNA encoding the Cas9 nuclease harboring inactivating D10A/H840A mutations (dCas9) was amplified by PCR from plasmid pMJ841 (Addgene plasmid #39318) using primers that add a T7 promoter site 5' to the start codon and a nuclear localization signal at the carboxy-terminal end of the Cas9 coding sequences and cloned into a plasmid containing a CMV promoter as previously described (Hwang et al., Nat Biotechnol 31, 227-229 (2013)) to yield plasmid pMLM3629. Oligonucleotides encoding a triple FLAG epitope were annealed and cloned into XhoI and PstI sites in plasmid pMLM3629 to generate plasmid pMLM3647 expressing dCas9 with a C-terminal flag FLAG tag. DNA sequence encoding a $Gly_4Ser$ linker followed by the synthetic VP64 activation domain was introduced downstream of the FLAG-tagged dCas9 in plasmid pMLM3647 to yield plasmid pSL690. The D10A/H840A mutations were also introduced by QuikChange site-directed mutagenesis (Agilent) into plasmid pJDS247, which encodes a FLAG-tagged Cas9 sequence that has been codon optimized for expression in human cells, to yield plasmid pMLM3668. DNA sequence encoding the $Gly_4Ser$ linker and the VP64 activation domain were then cloned into pMLM3668 to yield a codon-optimized dCas9-VP64 expression vector named pMLM3705.

Cell Culture, Transfection and ELISA Assays were performed as follows. Flp-In T-Rex 293 cells were maintained in Advanced DMEM supplemented with 10% FBS, 1% penstrep and 1% Glutamax (Invitrogen). Cells were transfected by Lipofectamine LTX (Invitrogen) according to manufacturer's instructions. Briefly, 160,000 293 cells were seeded in 24-well plates and transfected the following day with 250 ng gRNA plasmid, 250 ng Cas9-VP64 plasmid, 30 ng pmaxGFP plasmid (Lonza), 0.5 µl Plus Reagent and 1.65 µl Lipofectamine LTX. Tissue culture media from transfected 293 cells was harvested 40 hours after transfection, and secreted VEGF-A protein assayed using R&D System's Human VEGF-A ELISA kit "Human VEGF Immunoassay."

Figure 1E:
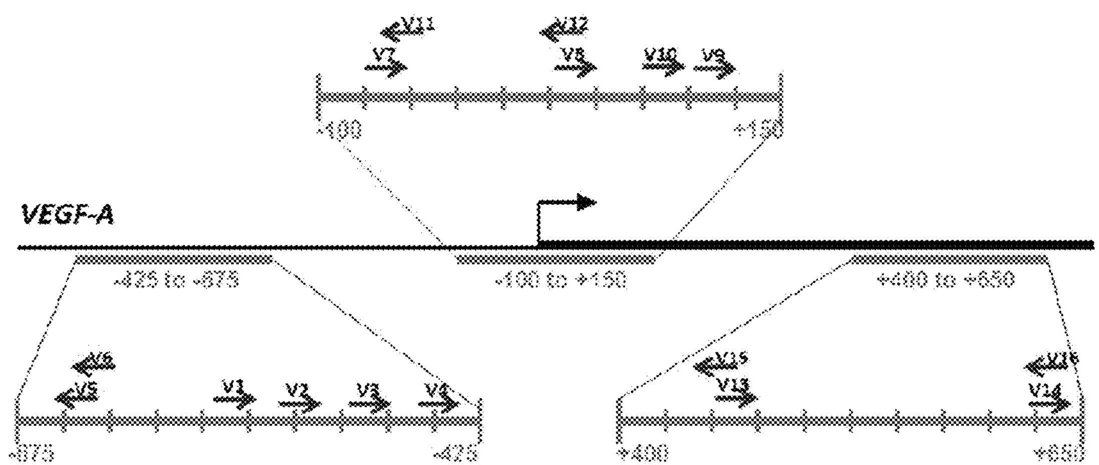
FIG. 1E is a diagram illustrating the positions and orientations of 16 sgRNAs targeted to the endogenous human VEGFA gene promoter. Small horizontal arrows represent the first 20 nts of the gRNA complementary to the genomic DNA sequence with the arrow pointing 5' to 3'. Grey bars indicate DNaseI hypersensitive sites previously defined in human 293 cells (Liu et al., J Biol Chem. 2001 Apr. 6; 276(14):11323-34), numbered relative to the transcription start site (right-angle arrow).

16 sgRNAs were constructed for target sequences within three DNase I hyper-sensitive sites (HSSs) located upstream, downstream or at the transcription start site of the human VEGFA gene in 293 cells (FIG. 1E).

Before testing the abilities of the 16 VEGFA-targeted gRNAs to recruit a novel dCas9-VP64 fusion protein, each of these gRNAs was first assessed for its ability to direct Cas9 nuclease to its intended target site in human 293 cells. For this purpose, gRNA and Cas9 expression vectors were transfected in a 1:3 ratio because previous optimization experiments demonstrated a high level of Cas9-induced DNA cleavage in U2OS cells using this ratio of plasmids.

Transfections of 293 cells were performed as described above for the dCas9-VP16 VEGFA experiments except that cells were transfected with 125 ng of plasmid encoding VEGFA-targeted gRNAs and 375 ng of plasmid encoding active Cas9 nuclease (pMLM3639). 40 hours post-transfection, genomic DNA was isolated using the QIAamp DNA Blood Mini kit (Qiagen) according to manufacturer's instructions. PCR amplification of the three different targeted regions in the VEGFA promoter was performed using Phusion Hot Start II high-fidelity DNA polymerase (NEB) with 3% DMSO and the following touchdown PCR cycle: 10 cycles of 98° C., 10 s; 72-62° C., −1° C./cycle, 15 s; 72° C., 30 s, followed by 25 cycles of 98° C., 10 s; 62° C., 15 s; 72° C., 30 s. The −500 region was amplified using primers oFYF434 (5'-TCCAGATGGCACATTGTCAG-3' (SEQ ID NO:82)) and oFYF435 (5'-AGGGAGCAGGAAAGTGAGGT-3' (SEQ ID NO:83)). The region around the transcription start site was amplified using primers oFYF438 (5'-GCACGTAACCTCACTTTCCT-3' (SEQ ID NO:84)) and oFYF439 (5'-CTTGCTACCTCTTTCCTCTTTCT-3' (SEQ ID NO:85)). The +500 region was amplified using primers oFYF444 (5'-AGAGAAGTCGAGGAAGAGAGAG-3' (SEQ ID NO:86)) and oFYF445 (5'-CAGCAGAAAGTTCATGGTTTCG-3' (SEQ ID NO:87)). PCR products were purified using Ampure XP beads (Agencourt) and T7 Endonuclease I assays were performed and analyzed on a QIAXCEL capillary electrophoresis system as previously described (Reyon et al., Nat Biotech 30, 460-465 (2012)).

All 16 gRNAs were able to mediate the efficient introduction of Cas9 nuclease-induced indel mutations at their respective target sites as assessed using a previously described T7E1 genotyping assay (Table 2). Thus all 16 gRNAs can complex with Cas9 nuclease and direct its activity to specific target genomic sites in human cells.

TABLE 2

Frequencies of indel mutations induced by VEGFA-targeted gRNAs and Cas9 nuclease

| gRNA | Mean Indel Mutation Frequency (%) ± SEM |
|---|---|
| V1 | 18.05 ± 0.47 |
| V2 | 41.48 ± 0.62 |
| V3 | 33.22 ± 1.05 |
| V4 | 16.97 ± 0.06 |
| V5 | 7.46 ± 0.50 |
| V6 | 16.99 ± 0.51 |
| V7 | 1.42 ± 0.11 |
| V8 | 34.07 ± 0.90 |
| V9 | 24.53 ± 1.40 |
| V10 | 35.65 ± 1.35 |
| V11 | 4.45 ± 0.22 |
| V12 | 23.95 ± 0.41 |
| V13 | 9.45 ± 0.74 |
| V14 | 12,17 ± 0.36 |
| V15 | 14.28 ± 0.54 |
| V16 | 18.82 ± 1.48 |

To test whether dCas9-VP64 protein could also be targeted to specific genomic sites in human cells by these same gRNAs, Enzyme-Linked Immunoblot Assays of VEGFA protein were performed as follows. Culture medium of Flp-In T-Rex HEK293 cells transfected with plasmids encoding VEGFA-targeted sgRNA and dCas9-VP64 was harvested 40 hours post-transfection and VEGFA protein expression was measured by ELISA as previously described (Maeder et al., Nat Methods 10, 243-245 (2013)). Fold-activation of VEGFA expression was calculated by dividing the concentration of VEGFA protein in media from cells in which both a sgRNA and dCas9-VP64 were expressed by the concentration of VEGFA protein in media from cells in which an off-target sgRNA (targeted to a sequence in the EGFP reporter gene) and dCas9-VP64 were expressed.

Figure 2A:
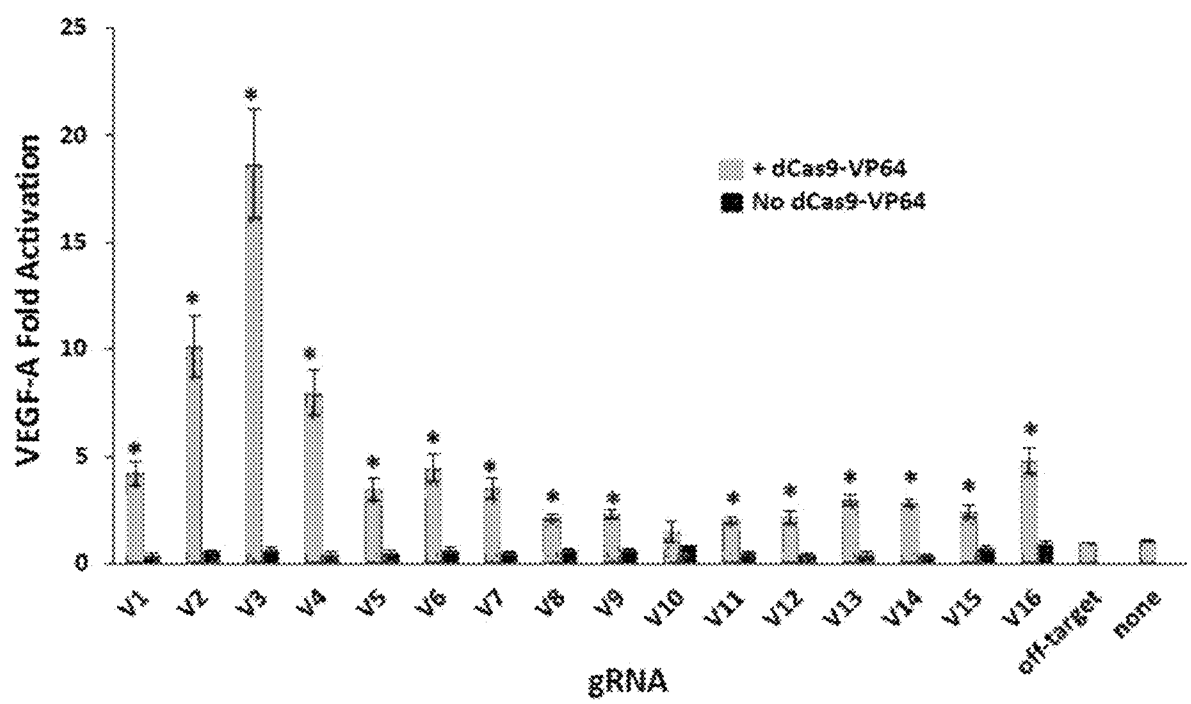
FIG. 2A is a bar graph showing activation of VEGFA protein expression in 293 cells by various sgRNAs, each expressed with (grey bars) or without (black bars) dCas9-VP64. Fold-activation of VEGFA was calculated relative to the off-target sgRNA control as described in Methods. Each experiment was performed in triplicate and error bars represent standard errors of the mean. Asterisks indicate samples that are significantly elevated above the off-target control as determined by a paired, one-sided t-test ($p<0.05$).

15 of the 16 gRNAs tested induced significant increases in VEGFA protein expression when co-expressed with dCas9-VP64 in human 293 cells (FIG. 2A). The magnitude of VEGFA induction observed ranged from two- to 18.7-fold-activation with a mean of five-fold-activation. Control experiments revealed that expression of each of the 16 gRNAs alone, dCas9-VP64 alone, and dCas9-VP64 together with an "off-target" gRNA designed to bind an EGFP reporter gene sequence all failed to induce elevated VEGFA expression (FIG. 2A), demonstrating that co-expression of a specific gRNA and the dCas9-VP64 protein are both required for promoter activation. Thus dCas9-VP64 is stably expressed and can be directed by gRNAs to activate transcription of specific genomic loci in human cells. The greatest increase in VEGFA was observed in cells transfected with gRNA3, which induced protein expression by 18.7-fold. Interestingly, the three best gRNAs, and 6 of the 9 gRNAs capable of inducing expression by 3-fold or more, target the −500 region (~500 bp upstream of the transcription start site).

Figure 2B:
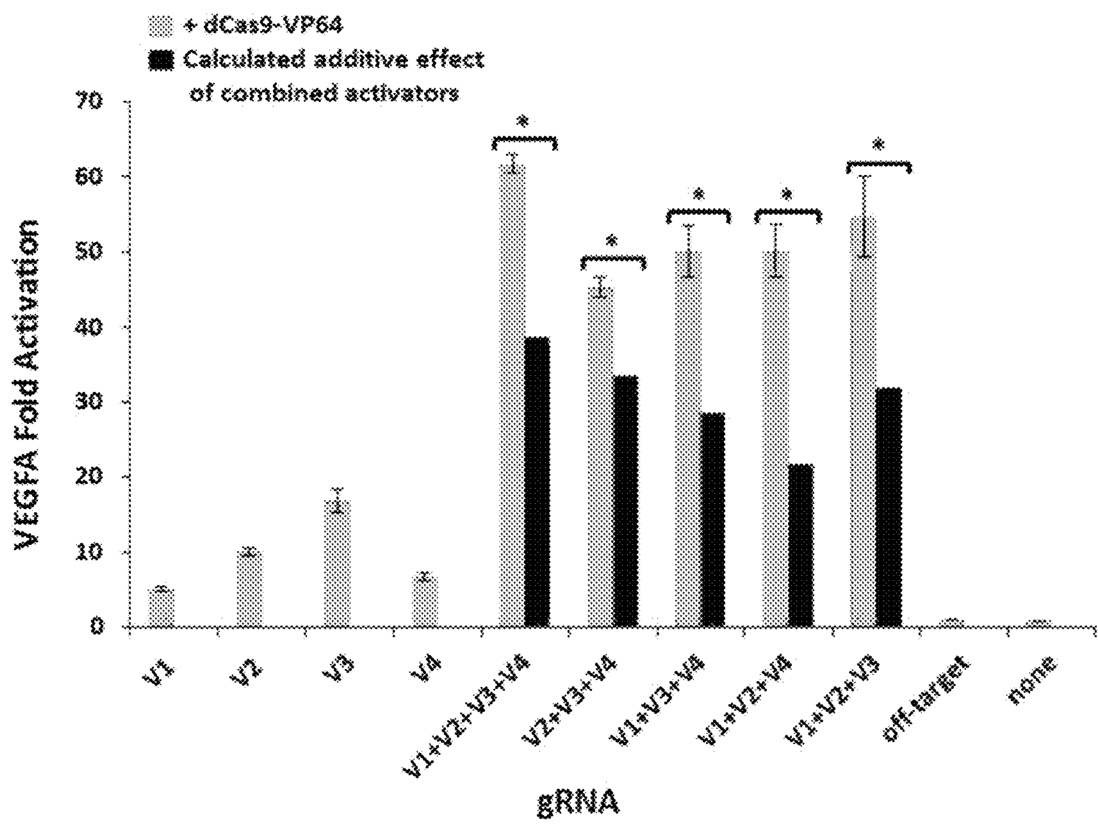
FIG. 2B is a bar graph showing multiplex sgRNA expression induces synergistic activation of VEGFA protein expression by dCas9-VP64 protein. Fold-activation of VEGFA protein in 293 cells in which the indicated combinations of sgRNAs were co-expressed with dCas9-VP64 is shown. Note that in all of these experiments the amount of each individual sgRNA expression plasmid used for transfection was the same. Fold-activation values were calculated as described in 2A and shown as grey bars. The calculated sum of mean fold-activation values induced by individual sgRNAs is shown for each combination as black bars. Asterisks indicate all combinations that were found to be significantly greater than the expected sum as determined by an analysis of variance (ANOVA) ($p<0.05$).

Because in one aspect the system described herein uses variable gRNAs to recruit a common dCas9-VP64 activator fusion, one can envision that the expression of multiple guide RNAs in a single cell might enable multiplex or combinatorial activation of endogenous gene targets. To test this possibility, 293 cells were transfected with dCas9-VP64 expression plasmid together with expression plasmids for four gRNAs (V1, V2, V3, and V4) that each individually induced expression from the VEGFA promoter. Co-expression of all four gRNAs with dCas9-VP64 induced synergistic activation of VEGFA protein expression (i.e., a fold-activation greater than the expected additive effects of each individual activator) (FIG. 2B). In addition, various combinations of three of these four activators also activated the VEGFA promoter synergistically (FIG. 2B). Because synergistic activation of transcription is believed to result from the recruitment of multiple activator domains to a single promoter, multiple gRNA/dCas9-VP64 complexes are likely to be simultaneously binding to the VEGFA promoter in these experiments.

These experiments demonstrate that co-expression of a Cas9-HFD, e.g., a Cas9-activator protein (harboring the VP64 transcriptional activation domain) and a sgRNA with 20 nt of sequence complementarity to sites in the human VEGF-A promoter in human HEK293 cells can result in upregulation of VEGF-A expression. Increases in VEGF-A protein were measured by ELISA assay and it was found that individual gRNAs can function together with a Cas9-activator fusion protein to increase VEGF-A protein levels by up to −18-fold (FIG. 2A). Additionally, it was possible to achieve even greater increases in activation through transcriptional synergy by introducing multiple gRNAs targeting various sites in the same promoter together with Cas9-activator fusion proteins (FIG. 2B).

Figure 3A:
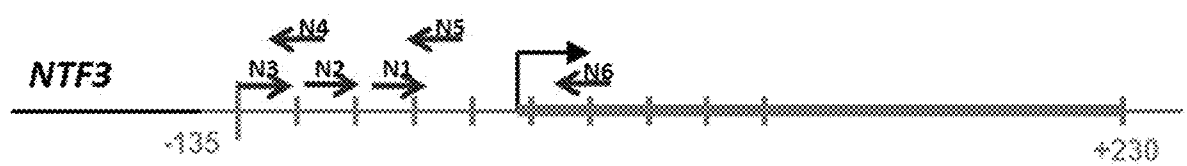
FIG. 3A is a diagram illustrating the positions and orientations of six sgRNAs targeted to the endogenous human NTF3 gene promoter. Horizontal arrows represent the first 20 nts of the sgRNA complementary to the genomic DNA sequence with the arrow pointing 5' to 3'. Grey line indicates region of potential open chromatin identified from the ENCODE DNaseI hypersensitivity track on the UCSC genome browser with the thicker part of the bar indicating the first transcribed exon. Numbering shown is relative to the transcription start site (+1, right-angle arrow).

Example 2. Engineering CRISPR/Cas Activator System Targeting the Endogenous Human NTF3 Gene To extend the generality of the present findings, we tested whether the RNA-guided activator platform could be used to induce the expression of the human NTF3 gene. To do this, six sgRNAs were designed to a predicted DNase I hypersensitive site (HSS) in the human NTF3 promoter and plasmids expressing each of these gRNAs were co-transfected with a plasmid encoding dCas9-VP64 protein that had been codon optimized for human cell expression (FIG. 3A).

Figure 3B:
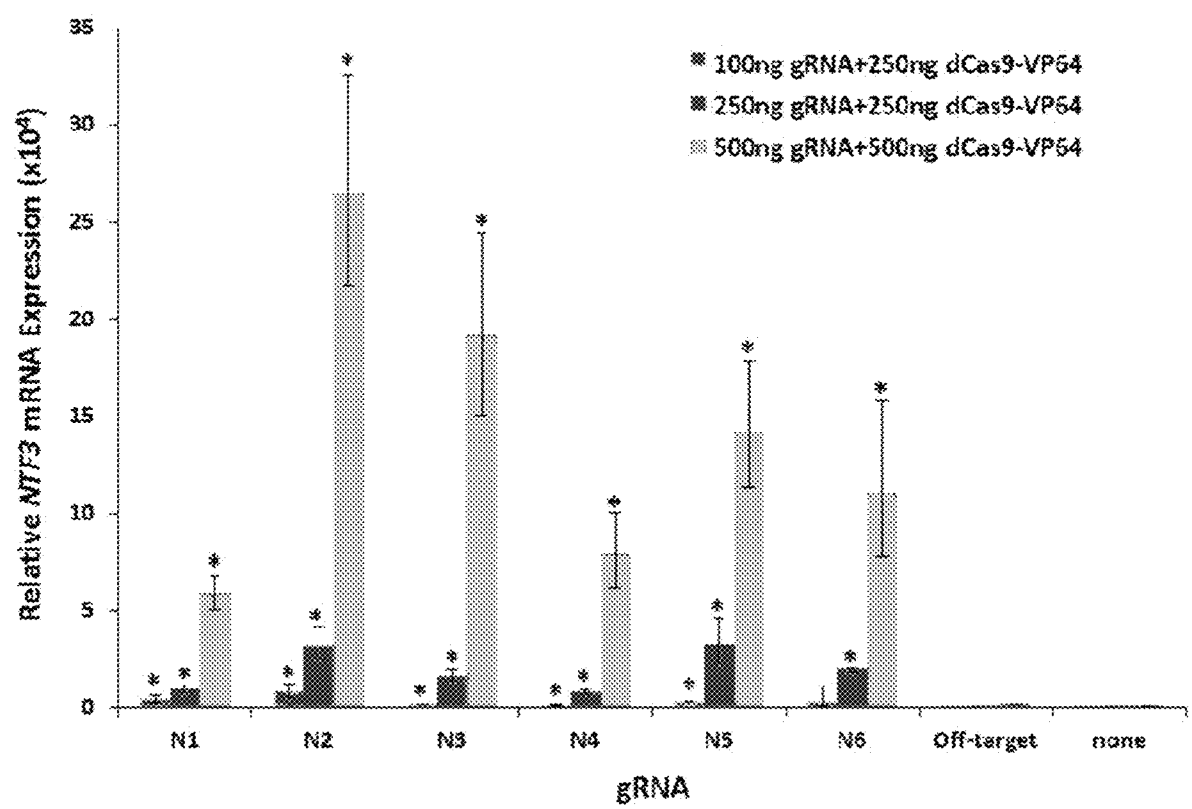
FIG. 3B is a bar graph showing activation of NTF3 gene expression by sgRNA-guided dCas9-VP64 in 293 cells. Relative expression of NTF3 mRNA, detected by quantitative RT-PCR and normalized to a GAPDH control (deltaCt$\times 10^4$), is shown for 293 cells co-transfected with the indicated amounts of dCas9-VP64 and NTF3-targeted sgRNA expression plasmids. All experiments were performed in triplicate with error bars representing standard errors of the mean. Asterisks indicate samples that are significantly greater than the off-target gRNA control as determined by a paired, one-sided T-test ($P<0.05$).
Figure 3C:
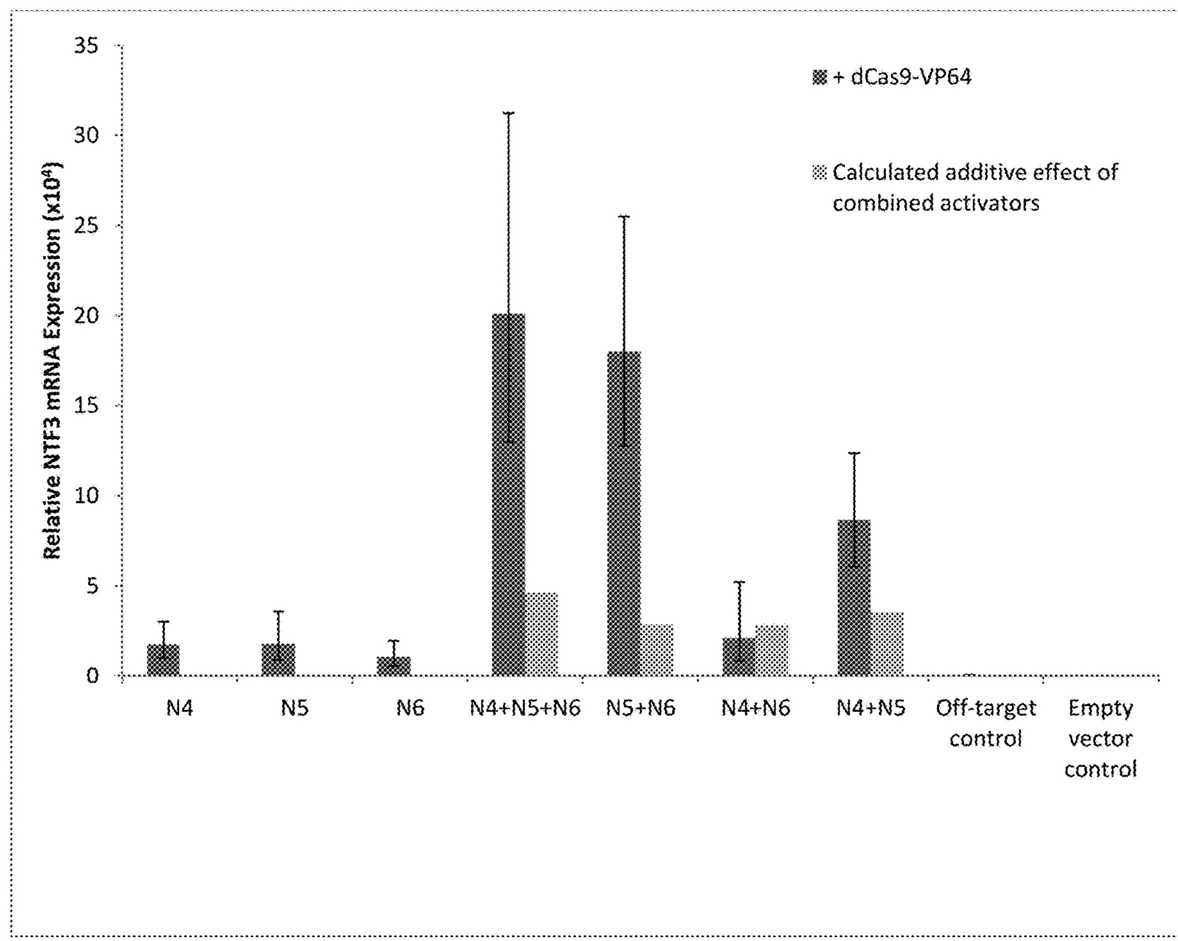
FIG. 3C is a bar graph showing multiplex gRNA expression induces synergistic activation of NTF3 mRNA expression by dCas9-VP64 protein. Relative expression of NTF3 mRNA, detected by quantitative RT-PCR and normalized to a GAPDH control (deltaCt×104), is shown for 293 cells co-transfected with dCas9-VP64 and the indicated combinations of NTF3-targeted gRNA expression plasmids. Note that in all of these experiments the amount of each individual gRNA expression plasmid used for transfection was the same. All experiments were performed in triplicate with error bars representing standard errors of the mean. The calculated sum of mean fold-activation values induced by individual gRNAs is shown for each combination.

All six gRNAs tested induced significant increases in NTF3 transcript levels as detected by quantitative RT-PCR (FIG. 3B). Although fold-activation values for these six RNA-guided activators could not be accurately calculated (because basal levels of transcript were essentially undetectable), the mean levels of activated NTF3 mRNA expression varied over a four-fold range. Decreasing the amounts of gRNA and dCas9-VP64 expression plasmids transfected resulted in less activation of the NTF3 gene (FIG. 3B), demonstrating a clear dose-dependent effect.

In addition, 293 cells were co-transfected with dCas9-VP64 and NTF3-targeted gRNA expression plasmids alone and in single and double combinations. Relative expression of NTF3 mRNA was detected by quantitative RT-PCR and normalized to a GAPDH control (deltaCt×$10^4$). In all of these experiments the amount of each individual gRNA expression plasmid used for transfection was the same. FIG. 3B shows that this multiplex gRNA expression induced synergistic activation of NTF3 mRNA expression by dCas9-VP64 protein.

Example 3. Engineering CRISPR/Cas-MS2, -Csy4 and -Lambda N Fusion Systems—Creating Biological Tethers Fusion proteins are made in which an MS2 coat protein, Csy4 nuclease (preferably catalytically inactive Csy4, e.g., the H29A mutant described in Haurwitz et al. 329(5997): 1355-8 (2010)), or the lambda N are fused to the N- or C-terminus of the inactivated dCas9. MS2 and lambda N are bacteriophage proteins that bind to a specific RNA sequence, and thus can be used as adapters to tether to the dCas9 protein a heterologous RNA sequence tagged with the specific MS2 or lambda N RNA binding sequence. dCas9-MS2 fusions or dCas9-lambda N fusions are co-expressed with chimeric long non-coding RNAs (lncRNAs) fused to the MS2 or lambda N stem loop recognition sequence on either their 5' or 3' end. Chimeric Xist or chimeric RepA lncRNAs will be specifically recruited by the dCas9 fusions and the ability of this strategy to induce targeted silencing will be assayed by measuring target gene expression. The system will be optimized by testing various alterations to the coat proteins and chimeric RNAs. The N55K and deltaFG mutations to the MS2 coat protein have been previously demonstrated to prevent protein aggregation and increase affinity for the stem-loop RNA. Additionally, we will test the high-affinity C-loop RNA mutant reported to increase affinity for the MS2 coat protein. Exemplary sequences for the MS2 and lambda N proteins are given below; the MS2 functions as a dimer, therefore the MS2 protein can include a fused single chain dimer sequence.

1. Exemplary Sequences for Fusions of Single MS2 Coat Protein (Wt, N55K or deltaFG) to the N-Terminus or C-Terminus of the dCas9.

MS2 coat protein amino acid sequence:
(SEQ ID NO: 88)
MASNFTQFVLVDNGGTGDVTVAPSNFANGVAEWISSNSRSQAYKVTCSV
RQSSAQNRKYTIKVEVPKVATQTVGGVELPVAAWRSYLNMELTIPIFAT
NSDCELIVKAMQGLLKDGNPIPSAIAANSGIY MS2 N55K:
(SEQ ID NO: 89)
MASNFTQFVLVDNGGTGDVTVAPSNFANGVAEWISSNSRSQAYKVTCSV
RQSSAQKRKYTIKVEVPKVATQTVGGVELPVAAWRSYLNMELTIPIFAT
NSDCELIVKAMQGLLKDGNPIPSAIAANSGIY MS2deltaFG:
(SEQ ID NO: 90)
MASNFTQFVLVDNGGTGDVTVAPSNFANGIAEWISSNSRSQAYKVTCSV
RQSSAQNRKYTIKVEVPKGAWRSYLNMELTIPIFATNSDCELIVKAMQG
LLKDGNPIPSAIAANSGIY 2. Exemplary Sequences for Fusions of Fused Dimeric MS2 Coat Protein (Wt, N55K or deltaFG) to the N-Terminus or C-Terminus of dCas9.

Dimeric MS2 coat protein:
(SEQ ID NO: 91
MASNFTQFVLVDNGGTGDVTVAPSNFANGVAEWISSNSRSQAYKVTCSV

RQSSAQNRKYTIKVEVPKVATQTVGGVELPVAAWRSYLNMELTIPIFAT

NSDCELIVKAMQGLLKDGNPIPSAIAANSGLYGAMASNFTQFVLVDNGG

TGDVTVAPSNFANGVAEWISSNSRSQAYKVTCSVRQSSAQNRKYTIKVE

VPKVATQTVGGVELPVAAWRSYLNMELTIPIFATNSDCELIVKAMQGLL

KDGNPIPSAIAANSLIN (SEQ ID NO: 92)
MASNFTQFVLVDNGGTGDVTVAPSNFANGVAEWISSNSRSQAYKVTCSV

RQSSAQKRKYTIKVEVPKVATQTVGGVELPVAAWRSYLNMELTIPIFAT

NSDCELIVKAMQGLLKDGNPIPSAIAANSGLYGAMASNFTQFVLVDNGG

TGDVTVAPSNFANGVAEWISSNSRSQAYKVTCSVRQSSAQKRKYTIKVE

VPKVATQTVGGVELPVAAWRSYLNMELTIPIFATNSDCELIVKAMQGLL

KDGNPIPSAIAANSLIN

Dimeric MS2deltaFG:
(SEQ ID NO: 93)
MASNFTQFVLVDNGGTGDVTVAPSNFANGVAEWISSNSRSQAYKVTCSV

RQSSAQKRKYTIKVEVPKGAWRSYLNMELTIPIFATNSDCELIVKAMQG

LLKDGNPIPSAIAANSGLYGAMASNFTQFVLVDNGGTGDVTVAPSNFAN

GVAEWISSNSRSQAYKVTCSVRQSSAQKRKYTIKVEVPKGAWRSYLNME

LTIPIFATNSDCELIVKAMQGLLKDGNPIPSAIAANSLIN

3. Exemplary Sequences for Fusions of Lambda N to N-Terminus or C-Terminus of dCas9.

Lambda N amino acid sequence:
(SEQ ID NO: 94)
MDAQTRRRERRAEKQAQWKAAN
or (SEQ ID NO: 95)
MDAQTRRRERRAEKQAQWKAANPLLVGVSAKPVNRPILSLNRKPKSRVE
SALNPIDLTVLAEYHKQIESNLQRIERKNQRTWYSKPGERGITCSGRQK
IKGKSIPLI 4. Exemplary Sequence for Fusions of Csy4 to N-Terminus or C-Terminus of dCas9

Exemplary sequences for Cys4 are given in Haurwitz et al. 329(5997):1355-8 (2010), e.g., the inactivated form.

The constructs are expressed in cells also expressing a regulatory RNA, e.g., a long non-coding RNA (lncRNA) such as HOTAIR, HOTTIP, XIST or XIST RepA, that has been fused with the cognate stem-loop recognition sequence for the lambda N or MS2 on either its 5' or 3' end. The wild type and high-affinity sequences for MS2 are AAACAUGAGGAUUACCCAUGUCG (SEQ ID NO:96) and AAACAUGAGGAUCACCCAUGUCG (SEQ ID NO:97), respectively (see Keryer-Bibens et al., supra, FIG. 2); the nutL and nutR BoxB sequences to which lambda N binds are GCCCUGAAGAAGGGC (SEQ ID NO:98) and GCCCUGAAAAAGGGC (SEQ ID NO:99), respectively. The sequence to which Csy4 binds is (truncated 20 nt)
(SEQ ID NO: 100)
GTTCACTGCCGTATAGGCAG
or (SEQ ID NO: 101)
GUUCACUGCCGUAUAGGCAGCUAAGAAA.

The binding of the dCas9/MS2 to a target site in a cell expressing an MS2-binding sequence tagged lncRNA recruits that lncRNA to the dCas9 binding site; where the lncRNA is a repressor, e.g., XIST, genes near the dCas9 binding site are repressed. Similarly, binding of the dCas9/lambdaN to a target site in a cell expressing an lambdaN-binding sequence tagged lncRNA recruits that lncRNA to the dCas9 binding site.

Example 4. Engineering CRISPR/Cas-HP1 Fusion Systems—Sequence-Specific Silencing The dCas9 fusion proteins described herein can also be used to target silencing domains, e.g., Heterochromatin Protein 1 (HP1, also known as swi6), e.g., HP1α or HP10. Truncated versions of HP1α or HP1β in which the chromodomain has been removed can be targeted to specific loci to induce heterochromatin formation and gene silencing. Exemplary sequences of truncated HP1 fused to dCas9 are shown in FIGS. 8A-8B. The HP1 sequences can be fused to the N- or C-terminus of the inactivated dCas9 as described above.

Example 5. Engineering CRISPR/Cas-TET Fusion Systems—Sequence-Specific Demethylation The dCas9 fusion proteins described herein can also be used to target enzymes that modify the methylation state of DNA (e.g., DNA methyltransferase (DNMT) or TET proteins). Truncated versions of TET1 can be targeted to specific loci to catalyze DNA demethylation. Exemplary sequences of truncated TET1 fused to dCas9 are shown in FIG. 9. The TET1 sequence can be fused to the N- or C-terminus of the inactivated dCas9 as described above.

Example 6. Engineering Optimized CRISPR/Cas-VP64 Fusions

Figure 10:
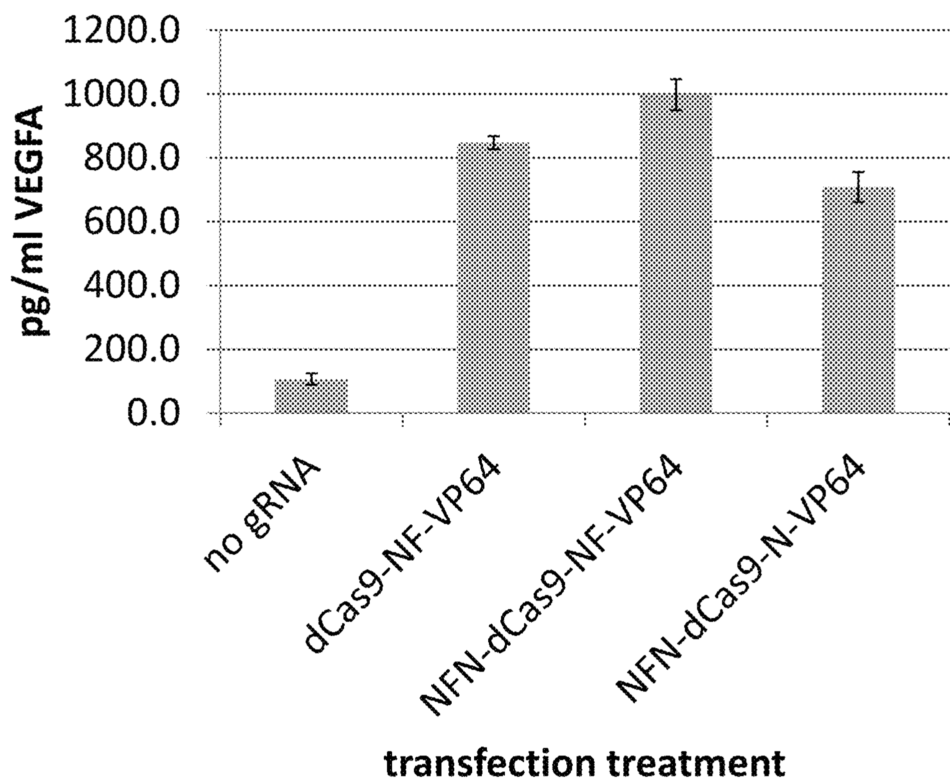
FIG. 10 is a bar graph showing results obtained with various dCas9-VP64 fusion constructs. Of those tested, the optimized dCas9-VP64 architecture included an N-terminal NLS (NFN) and an additional NLS (N) or FLAG tag/NLS (NF) placed between dCas9 and VP64. Expression of the VEGFA gene in human HEK293 cells was activated by transcriptional activation mediated by RNA-guided dCas9-VP64 fusions. Expression plasmids encoding variants of dCas9-VP64 were co-transfected with a plasmid that expressed three gRNAs that targeted sites in a region upstream of the VEGFA start codon (in this experiment, the gRNAs were expressed from a single gRNA and processed out by the Csy4 endoribonuclease). VEGFA protein expression is measured by ELISA, and the mean of two replicates is shown with error bars indicating standard errors of the mean.

The activities of dCas9-based transcription activators harboring the VP64 activation domain were optimized by varying the number and position of the nuclear localization signal(s) (NLS) and 3xFLAG-tags within these fusions (FIG. 10). dCas9-VP64 fusions that contain both an N-terminal NLS and an NLS that lies between the dCas9 and VP64 sequences consistently induce higher levels of target gene activation, perhaps resulting from enhanced nuclear localization of the activator (FIG. 10). Furthermore, even greater levels of activation were observed when a 3xFLAG tag was placed between the C-terminal end of dCas9 and the N-terminal end of VP64. The 3xFLAG tag may act as an artificial linker, providing necessary spacing between dCas9 and VP64 and perhaps allowing for better folding of the VP64 domain (that may not be possible when constrained near dCas9) or better recognition of VP64 by transcriptional mediator complexes that recruit RNA polymerase II. Alternatively, the negatively charged 3xFLAG tag might also function as a fortuitous transcriptional activation domain, enhancing the effects of the VP64 domain.

Example 7. Optimized CatalyticallyCatlytically Inactive Cas9 Proteins (dCas9)

Figure 11A:
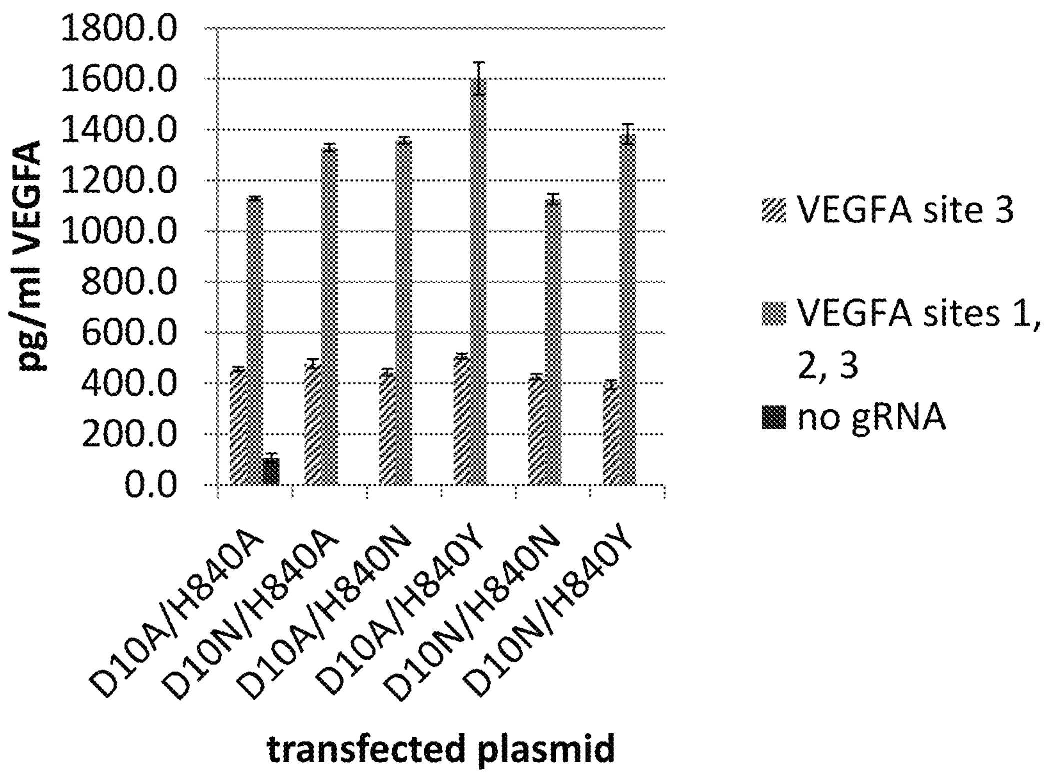
FIGS. 11A-B are bar graphs showing the activities of dCas9-VP64 activators bearing alternative substitution mutations to catalytically inactivate Cas9 function. (11A) Plasmids expressing dCas9-VP64 proteins bearing various Cas9 inactivating substitutions to residues D10 and H840 were each co-transfected into HEK293 cells with either a single gRNA or three distinctly targeted gRNAs targeting the VEGFA upstream region (blue and red bars, respectively). (11B) Plasmids expressing these dCas9-VP64 variants were also transfected into a HEK293 cell-line that stably expresses a single VEGFA-targeted gRNA. VEGFA protein levels were determined by ELISA with mean of two replicates and standard errors of the mean (error bars) shown.
Figure 11B:
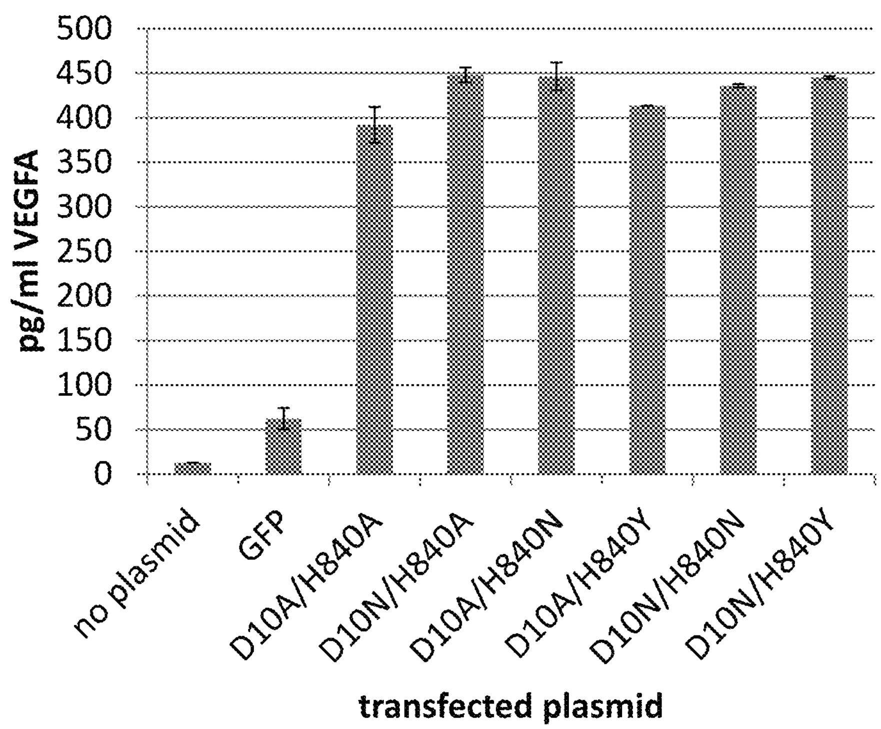

Additional optimization of the activities of dCas9-VP64 activators was performed by changing the nature of the inactivating mutations that abolish the nuclease activity of Cas9 in the dCas9 domain (FIG. 11A-B). In published studies to date, the catalytic residues D10 and H840 were mutated to alanine (D10A and H840A) to disrupt the active site networks that mediate the hydrolysis of DNA. It was hypothesized that alanine substitutions at these positions might result in destabilization of dCas9 and therefore sub-optimal activity. Therefore, more structurally conservative substitutions at D10 or H840 (for example, to asparagine or tyrosine residues: D1 ON, H840N, and H840Y) were tested to see if they might lead to greater gene activation by dCas9-VP64 fusions bearing these different mutations. When dCas9-VP64 variants bearing these variant substitutions were co-transfected into HEK293 cells with three gRNAs targeting upstream regions of the endogenous human VEGFA gene, greater VEGFA protein expression was observed for all but one of these variants (FIG. 11A). However, this effect was not as significant when the dCas9-VP64 variants were co-transfected with only one of these gRNAs (FIG. 11A), or when transfected into a HEK293 derivative cell-line that expresses a single VEGFA-targeted gRNA (FIG. 11B).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of silencing or repressing expression of a target gene in a cell, the method comprising expressing (i) a fusion protein comprising catalytically inactive CRISPR associated 9 (dCas9) protein linked to a heterologous functional domain, wherein the heterologous functional domain is a Heterochromatin Protein 1 (HP1), and (ii) one or more guide RNAs directed to the target gene.

2. The method of claim 1, wherein the catalytically inactive Cas9 protein is from *S. pyogenes*.

3. The method of claim 2, wherein the catalytically inactive Cas9 protein comprises mutations at D10, E762, H983, or D986; and at H840 or N863.

4. The method of claim 3, wherein the mutations are:

(i) D10A or D10N, and (ii) H840A, H840N, or H840Y.

5. The method of claim 1, wherein the heterologous functional domain is linked to the N terminus or C terminus of the catalytically inactive Cas9 protein, with an optional intervening linker, wherein the linker does not interfere with activity of the fusion protein.

6. The method of claim 1, further comprising one or both of a nuclear localization sequence and one or more epitope tags on the N-terminus, C-terminus, and/or in between the catalytically inactive CRISPR associated 9 (Cas9) protein and the heterologous functional domain, optionally with one or more intervening linkers.

7. The method of claim 6, wherein the epitope tag is c-myc, 6His, or FLAG.

* * * * *

SEQUENCE LISTING

```
<160> NUMBER OF SEQ ID NOS: 113

<210> SEQ ID NO 1
<211> LENGTH: 262
<212> TYPE: RNA
<213> ORGANISM: Artificial Sequence
<220> FEATURE:
<223> OTHER INFORMATION: Description of Artificial Sequence: Synthetic
      guide polynucleotide
<220> FEATURE:
<221> NAME/KEY: modified_base
<222> LOCATION: (1)..(20)
<223> OTHER INFORMATION: a, c, u, g, unknown or other and this region
      may encompass 17-20 nucleotides, wherein some positions may be
      absent
<220> FEATURE:
<221> NAME/KEY: modified_base
<222> LOCATION: (63)..(262)
<223> OTHER INFORMATION: a, c, u, g, unknown or other and this region
      may encompass 0-200 nucleotides, wherein some positions may be
      absent

<400> SEQUENCE: 1

nnnnnnnnnn nnnnnnnnnn guuuuagagc uagaaauagc aaguuaaaau aaggcuaguc      60

cgnnnnnnnn nnnnnnnnnn nnnnnnnnnn nnnnnnnnnn nnnnnnnnnn nnnnnnnnnn     120

nnnnnnnnnn nnnnnnnnnn nnnnnnnnnn nnnnnnnnnn nnnnnnnnnn nnnnnnnnnn     180

nnnnnnnnnn nnnnnnnnnn nnnnnnnnnn nnnnnnnnnn nnnnnnnnnn nnnnnnnnnn     240

nnnnnnnnnn nnnnnnnnnn nn                                              262


<210> SEQ ID NO 2
<211> LENGTH: 275
<212> TYPE: RNA
<213> ORGANISM: Artificial Sequence
<220> FEATURE:
<223> OTHER INFORMATION: Description of Artificial Sequence: Synthetic
      guide polynucleotide
<220> FEATURE:
```

<221> NAME/KEY: modified_base
<222> LOCATION: (1)..(20)
<223> OTHER INFORMATION: a, c, u, g, unknown or other and this region may encompass 17-20 nucleotides, wherein some positions may be absent
<220> FEATURE:
<221> NAME/KEY: modified_base
<222> LOCATION: (76)..(275)
<223> OTHER INFORMATION: a, c, u, g, unknown or other and this region may encompass 0-200 nucleotides, wherein some positions may be absent

<400> SEQUENCE: 2

```
nnnnnnnnnn nnnnnnnnnn guuuuagagc uaugcugaaa agcauagcaa guuaaaauaa     60

ggcuaguccg uuaucnnnnn nnnnnnnnnn nnnnnnnnnn nnnnnnnnnn nnnnnnnnnn    120

nnnnnnnnnn nnnnnnnnnn nnnnnnnnnn nnnnnnnnnn nnnnnnnnnn nnnnnnnnnn    180

nnnnnnnnnn nnnnnnnnnn nnnnnnnnnn nnnnnnnnnn nnnnnnnnnn nnnnnnnnnn    240

nnnnnnnnnn nnnnnnnnnn nnnnnnnnnn nnnnn                                275
```

<210> SEQ ID NO 3
<211> LENGTH: 287
<212> TYPE: RNA
<213> ORGANISM: Artificial Sequence
<220> FEATURE:
<223> OTHER INFORMATION: Description of Artificial Sequence: Synthetic guide polynucleotide
<220> FEATURE:
<221> NAME/KEY: modified_base
<222> LOCATION: (1)..(20)
<223> OTHER INFORMATION: a, c, u, g, unknown or other and this region may encompass 17-20 nucleotides, wherein some positions may be absent
<220> FEATURE:
<221> NAME/KEY: modified_base
<222> LOCATION: (88)..(287)
<223> OTHER INFORMATION: a, c, u, g, unknown or other and this region may encompass 0-200 nucleotides, wherein some positions may be absent

<400> SEQUENCE: 3

```
nnnnnnnnnn nnnnnnnnnn guuuuagagc uaugcuguuu uggaaacaaa acagcauagc     60

aaguuaaaau aaggcuaguc cguuaucnnn nnnnnnnnnn nnnnnnnnnn nnnnnnnnnn    120

nnnnnnnnnn nnnnnnnnnn nnnnnnnnnn nnnnnnnnnn nnnnnnnnnn nnnnnnnnnn    180

nnnnnnnnnn nnnnnnnnnn nnnnnnnnnn nnnnnnnnnn nnnnnnnnnn nnnnnnnnnn    240

nnnnnnnnnn nnnnnnnnnn nnnnnnnnnn nnnnnnnnnn nnnnnnn                   287
```

<210> SEQ ID NO 4
<211> LENGTH: 296
<212> TYPE: RNA
<213> ORGANISM: Artificial Sequence
<220> FEATURE:
<223> OTHER INFORMATION: Description of Artificial Sequence: Synthetic guide polynucleotide
<220> FEATURE:
<221> NAME/KEY: modified_base
<222> LOCATION: (1)..(20)
<223> OTHER INFORMATION: a, c, u, g, unknown or other and this region may encompass 17-20 nucleotides, wherein some positions may be absent
<220> FEATURE:
<221> NAME/KEY: modified_base
<222> LOCATION: (97)..(296)
<223> OTHER INFORMATION: a, c, u, g, unknown or other and this region may encompass 0-200 nucleotides, wherein some positions may be absent

<400> SEQUENCE: 4

-continued

```
nnnnnnnnnn nnnnnnnnnn guuuuagagc uagaaauagc aaguuaaaau aaggcuaguc     60

cguuaucaac uugaaaaagu ggcaccgagu cggugcnnnn nnnnnnnnnn nnnnnnnnnn    120

nnnnnnnnnn nnnnnnnnnn nnnnnnnnnn nnnnnnnnnn nnnnnnnnnn nnnnnnnnnn    180

nnnnnnnnnn nnnnnnnnnn nnnnnnnnnn nnnnnnnnnn nnnnnnnnnn nnnnnnnnnn    240

nnnnnnnnnn nnnnnnnnnn nnnnnnnnnn nnnnnnnnnn nnnnnnnnnn nnnnnn        296


<210> SEQ ID NO 5
<211> LENGTH: 96
<212> TYPE: RNA
<213> ORGANISM: Artificial Sequence
<220> FEATURE:
<223> OTHER INFORMATION: Description of Artificial Sequence: Synthetic
      guide oligonucleotide
<220> FEATURE:
<221> NAME/KEY: modified_base
<222> LOCATION: (1)..(20)
<223> OTHER INFORMATION: a, c, u, g, unknown or other and this region
      may encompass 17-20 nucleotides, wherein some positions may be
      absent

<400> SEQUENCE: 5

nnnnnnnnnn nnnnnnnnnn guuuaagagc uagaaauagc aaguuuaaau aaggcuaguc     60

cguuaucaac uugaaaaagu ggcaccgagu cggugc                               96


<210> SEQ ID NO 6
<211> LENGTH: 106
<212> TYPE: RNA
<213> ORGANISM: Artificial Sequence
<220> FEATURE:
<223> OTHER INFORMATION: Description of Artificial Sequence: Synthetic
      guide polynucleotide
<220> FEATURE:
<221> NAME/KEY: modified_base
<222> LOCATION: (1)..(20)
<223> OTHER INFORMATION: a, c, u, g, unknown or other and this region
      may encompass 17-20 nucleotides, wherein some positions may be
      absent

<400> SEQUENCE: 6

nnnnnnnnnn nnnnnnnnnn guuuuagagc uaugcuggaa acagcauagc aaguuuaaau     60

aaggcuaguc cguuaucaac uugaaaaagu ggcaccgagu cggugc                   106


<210> SEQ ID NO 7
<211> LENGTH: 106
<212> TYPE: RNA
<213> ORGANISM: Artificial Sequence
<220> FEATURE:
<223> OTHER INFORMATION: Description of Artificial Sequence: Synthetic
      guide polynucleotide
<220> FEATURE:
<221> NAME/KEY: modified_base
<222> LOCATION: (1)..(20)
<223> OTHER INFORMATION: a, c, u, g, unknown or other and this region
      may encompass 17-20 nucleotides, wherein some positions may be
      absent

<400> SEQUENCE: 7

nnnnnnnnnn nnnnnnnnnn guuuaagagc uaugcuggaa acagcauagc aaguuuaaau     60

aaggcuaguc cguuaucaac uugaaaaagu ggcaccgagu cggugc                   106


<210> SEQ ID NO 8
<211> LENGTH: 79
<212> TYPE: RNA
<213> ORGANISM: Artificial Sequence
```

<220> FEATURE:
<223> OTHER INFORMATION: Description of Artificial Sequence: Synthetic guide oligonucleotide

<400> SEQUENCE: 8

```
ggaaccauuc aaaacagcau agcaaguuaa aauaaggcua guccguuauc aacuugaaaa     60

aguggcaccg agucggugc                                                  79
```

<210> SEQ ID NO 9
<211> LENGTH: 62
<212> TYPE: RNA
<213> ORGANISM: Artificial Sequence
<220> FEATURE:
<223> OTHER INFORMATION: Description of Artificial Sequence: Synthetic guide oligonucleotide

<400> SEQUENCE: 9

```
ggagcgagcg gagcgguaca guuuuagagc uagaaauagc aaguuaaaau aaggcuaguc     60

cg                                                                    62
```

<210> SEQ ID NO 10
<211> LENGTH: 100
<212> TYPE: RNA
<213> ORGANISM: Artificial Sequence
<220> FEATURE:
<223> OTHER INFORMATION: Description of Artificial Sequence: Synthetic guide polynucleotide

<400> SEQUENCE: 10

```
ggagcgagcg gagcgguaca guuuuagagc uagaaauagc aaguuaaaau aaggcuaguc     60

cguuaucaac uugaaaaagu ggcaccgagu cggugcuuuu                          100
```

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic nuclear localization signal peptide

<400> SEQUENCE: 11

```
Pro Lys Lys Lys Arg Lys Val Ser
1               5
```

<210> SEQ ID NO 12
<211> LENGTH: 50
<212> TYPE: PRT
<213> ORGANISM: Artificial Sequence
<220> FEATURE:
<223> OTHER INFORMATION: Description of Artificial Sequence: Synthetic VP64 domain polypeptide

<400> SEQUENCE: 12

```
Asp Ala Leu Asp Asp Phe Asp Leu Asp Met Leu Gly Ser Asp Ala Leu
1               5                   10                  15

Asp Asp Phe Asp Leu Asp Met Leu Gly Ser Asp Ala Leu Asp Asp Phe
            20                  25                  30

Asp Leu Asp Met Leu Gly Ser Asp Ala Leu Asp Asp Phe Asp Leu Asp
        35                  40                  45

Met Leu
    50
```

<210> SEQ ID NO 13

```
<211> LENGTH: 1368
<212> TYPE: PRT
<213> ORGANISM: Streptococcus pyogenes

<400> SEQUENCE: 13

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
```

-continued

```
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815
```

```
Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110

Arg Asn  Ser Asp Lys Leu Ile  Ala Arg Lys Lys Asp  Trp Asp Pro
    1115                1120                1125

Lys Lys  Tyr Gly Gly Phe Asp  Ser Pro Thr Val Ala  Tyr Ser Val
    1130                1135                1140

Leu Val  Val Ala Lys Val Glu  Lys Gly Lys Ser Lys  Lys Leu Lys
    1145                1150                1155

Ser Val  Lys Glu Leu Leu Gly  Ile Thr Ile Met Glu  Arg Ser Ser
    1160                1165                1170

Phe Glu  Lys Asn Pro Ile Asp  Phe Leu Glu Ala Lys  Gly Tyr Lys
    1175                1180                1185

Glu Val  Lys Lys Asp Leu Ile  Ile Lys Leu Pro Lys  Tyr Ser Leu
    1190                1195                1200

Phe Glu  Leu Glu Asn Gly Arg  Lys Arg Met Leu Ala  Ser Ala Gly
    1205                1210                1215
```

```
Glu Leu  Gln Lys Gly Asn Glu  Leu Ala Leu Pro Ser  Lys Tyr Val
    1220                 1225                 1230

Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365
```

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic linker peptide

<400> SEQUENCE: 14

```
Gly Gly Gly Ser
1
```

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic linker peptide

<400> SEQUENCE: 15

```
Gly Gly Gly Gly Ser
1               5
```

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 16

```
gtgtgcagac ggcagtcact agg                                          23
```

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 17
gagcagcgtc ttcgagagtg agg 23

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 18
ggtgagtgag tgtgtgcgtg tgg 23

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 19
gttggagcgg ggagaaggcc agg 23

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 20
gggtgggggg agtttgctcc tgg 23

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 21
ggctttggaa agggggtggg ggg 23

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 22
ggggcggggt cccggcgggg cgg 23

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 23
gctcggaggt cgtggcgctg ggg 23

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 24
gactcaccgg ccagggcgct cgg 23

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 25
ggcgcagcgg ttaggtggac cgg 23

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 26
ggcgcatggc tccgccccgc cgg 23

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 27
gccacgacct ccgagctacc cgg 23

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 28
gcggcgtgag ccctccccct tgg 23

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 29
ggaggcgggg tggagggggt cgg 23

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 30
gggctcacgc cgcgctccgg cgg 23

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 31
gaccccctcc accccgcctc cgg 23

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 32
gagcgcggag ccatctggcc ggg 23

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 33
gcgcggcgcg gaaggggtta agg 23

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 34
gcggcgcggc gcgggccggc ggg 23

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 35
gccgcgccgc cctcccccgc cgg 23

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 36
gcggttataa ccagccaacc cgg 23

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 37
gtgcgcggag ctgttcggaa ggg 23

<210> SEQ ID NO 38
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 38
acaccgtgtg cagacggcag tcactg 26

<210> SEQ ID NO 39
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 39
acaccgagca gcgtcttcga gagtgg 26

<210> SEQ ID NO 40
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 40
acaccggtga gtgagtgtgt gcgtgg 26

<210> SEQ ID NO 41
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 41
acaccgttgg agcggggaga aggccg 26

<210> SEQ ID NO 42
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 42
acaccgggtg gggggagttt gctccg 26

<210> SEQ ID NO 43
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 43
acaccggctt tggaaagggg gtgggg 26

<210> SEQ ID NO 44
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 44
acaccggggc ggggtcccgg cggggg 26

<210> SEQ ID NO 45
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 45
acaccgctcg gaggtcgtgg cgctgg 26

<210> SEQ ID NO 46
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 46
acaccgactc accggccagg gcgctg 26

<210> SEQ ID NO 47
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 47
acaccggcgc agcggttagg tggacg 26

<210> SEQ ID NO 48
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 48
acaccggcgc atggctccgc cccgcg 26

<210> SEQ ID NO 49
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 49
acaccgccac gacctccgag ctaccg 26

<210> SEQ ID NO 50
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 50
acaccgcggc gtgagccctc cccctg 26

<210> SEQ ID NO 51
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 51
acaccggagg cggggtggag ggggtg 26

<210> SEQ ID NO 52
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 52
acaccgggct cacgccgcgc tccggg 26

<210> SEQ ID NO 53
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 53
acaccgaccc cctccacccc gcctcg 26

<210> SEQ ID NO 54
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 54
acaccgagcg cggagccatc tggccg 26

<210> SEQ ID NO 55
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 55
acaccgcgcg gcgcggaagg ggttag 26

<210> SEQ ID NO 56
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 56
acaccgcggc gcggcgcggg ccggcg 26

<210> SEQ ID NO 57
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 57
acaccgccgc gccgccctcc cccgcg 26

<210> SEQ ID NO 58
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 58
acaccgcggt tataaccagc caaccg 26

<210> SEQ ID NO 59
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 59
acaccgtgcg cggagctgtt cggaag 26

<210> SEQ ID NO 60

<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 60
aaaacagtga ctgccgtctg cacacg 26

<210> SEQ ID NO 61
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 61
aaaaccactc tcgaagacgc tgctcg 26

<210> SEQ ID NO 62
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 62
aaaaccacgc acacactcac tcaccg 26

<210> SEQ ID NO 63
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 63
aaaacggcct tctccccgct ccaacg 26

<210> SEQ ID NO 64
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 64
aaaacggagc aaactccccc cacccg 26

<210> SEQ ID NO 65
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 65
aaaaccccac cccctttcca aagccg 26

<210> SEQ ID NO 66
<211> LENGTH: 26

<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 66 aaaaccccg ccgggacccc gccccg 26

<210> SEQ ID NO 67
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 67
aaaaccagcg ccacgacctc cgagcg 26

<210> SEQ ID NO 68
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 68
aaaacagcgc cctggccggt gagtcg 26

<210> SEQ ID NO 69
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 69
aaaacgtcca cctaaccgct gcgccg 26

<210> SEQ ID NO 70
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 70
aaaacgcggg gcggagccat gcgccg 26

<210> SEQ ID NO 71
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 71
aaaacggtag ctcggaggtc gtggcg 26

<210> SEQ ID NO 72
<211> LENGTH: 26
<212> TYPE: DNA

<213> ORGANISM: Artificial Sequence
<220> FEATURE:
<223> OTHER INFORMATION: Description of Artificial Sequence: Synthetic target binding site oligonucleotide

<400> SEQUENCE: 72
aaaacagggg gagggctcac gccgcg 26

<210> SEQ ID NO 73
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 73
aaaacacccc ctccaccccg cctccg 26

<210> SEQ ID NO 74
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 74
aaaacccgga gcgcggcgtg agcccg 26

<210> SEQ ID NO 75
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 75
aaaacgaggc ggggtggagg gggtcg 26

<210> SEQ ID NO 76
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 76
aaaacggcca gatggctccg cgctcg 26

<210> SEQ ID NO 77
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 77
aaaactaacc ccttccgcgc cgcgcg 26

<210> SEQ ID NO 78
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 78
aaaacgccgg cccgcgccgc gccgcg 26

<210> SEQ ID NO 79
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 79
aaaacgcggg ggagggcggc gcggcg 26

<210> SEQ ID NO 80
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 80
aaaacggttg gctggttata accgcg 26

<210> SEQ ID NO 81
<211> LENGTH: 26
<212> TYPE: DNA
<213> ORGANISM: Artificial Sequence
<220> FEATURE:
<223> OTHER INFORMATION: Description of Artificial Sequence: Synthetic target binding site oligonucleotide

<400> SEQUENCE: 81
aaaacttccg aacagctccg cgcacg 26

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 82
tccagatggc acattgtcag 20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 83
agggagcagg aaagtgaggt 20

<210> SEQ ID NO 84
<211> LENGTH: 20
<212> TYPE: DNA
<213> ORGANISM: Artificial Sequence
<220> FEATURE:

<223> OTHER INFORMATION: Description of Artificial Sequence: Synthetic primer

<400> SEQUENCE: 84
gcacgtaacc tcactttcct 20

<210> SEQ ID NO 85
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 85
cttgctacct ctttcctctt tct 23

<210> SEQ ID NO 86
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 86
agagaagtcg aggaagagag ag 22

<210> SEQ ID NO 87
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 87
cagcagaaag ttcatggttt cg 22

<210> SEQ ID NO 88
<211> LENGTH: 130
<212> TYPE: PRT
<213> ORGANISM: Enterobacteria phage lambda

<400> SEQUENCE: 88

```
Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Asn Arg Lys Tyr Thr Ile Lys Val Glu
    50                  55                  60

Val Pro Lys Val Ala Thr Gln Thr Val Gly Gly Val Glu Leu Pro Val
65                  70                  75                  80

Ala Ala Trp Arg Ser Tyr Leu Asn Met Glu Leu Thr Ile Pro Ile Phe
                85                  90                  95

Ala Thr Asn Ser Asp Cys Glu Leu Ile Val Lys Ala Met Gln Gly Leu
            100                 105                 110

Leu Lys Asp Gly Asn Pro Ile Pro Ser Ala Ile Ala Ala Asn Ser Gly
        115                 120                 125

Ile Tyr
```

130

<210> SEQ ID NO 89
<211> LENGTH: 130
<212> TYPE: PRT
<213> ORGANISM: Artificial Sequence
<220> FEATURE:
<223> OTHER INFORMATION: Description of Artificial Sequence: Synthetic lambda bacteriophage MS2 N55K mutant polypeptide

<400> SEQUENCE: 89

```
Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Lys Arg Lys Tyr Thr Ile Lys Val Glu
    50                  55                  60

Val Pro Lys Val Ala Thr Gln Thr Val Gly Gly Val Glu Leu Pro Val
65                  70                  75                  80

Ala Ala Trp Arg Ser Tyr Leu Asn Met Glu Leu Thr Ile Pro Ile Phe
                85                  90                  95

Ala Thr Asn Ser Asp Cys Glu Leu Ile Val Lys Ala Met Gln Gly Leu
            100                 105                 110

Leu Lys Asp Gly Asn Pro Ile Pro Ser Ala Ile Ala Ala Asn Ser Gly
        115                 120                 125

Ile Tyr
    130
```

<210> SEQ ID NO 90
<211> LENGTH: 117
<212> TYPE: PRT
<213> ORGANISM: Artificial Sequence
<220> FEATURE:
<223> OTHER INFORMATION: Description of Artificial Sequence: Synthetic lambda bacteriophage MS2 deltaFG mutant polypeptide

<400> SEQUENCE: 90

```
Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Ile Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Asn Arg Lys Tyr Thr Ile Lys Val Glu
    50                  55                  60

Val Pro Lys Gly Ala Trp Arg Ser Tyr Leu Asn Met Glu Leu Thr Ile
65                  70                  75                  80

Pro Ile Phe Ala Thr Asn Ser Asp Cys Glu Leu Ile Val Lys Ala Met
                85                  90                  95

Gln Gly Leu Leu Lys Asp Gly Asn Pro Ile Pro Ser Ala Ile Ala Ala
            100                 105                 110

Asn Ser Gly Ile Tyr
        115
```

<210> SEQ ID NO 91
<211> LENGTH: 262
<212> TYPE: PRT

```
<213> ORGANISM: Artificial Sequence
<220> FEATURE:
<223> OTHER INFORMATION: Description of Artificial Sequence: Synthetic
      dimeric MS2 coat polypeptide

<400> SEQUENCE: 91

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Asn Arg Lys Tyr Thr Ile Lys Val Glu
    50                  55                  60

Val Pro Lys Val Ala Thr Gln Thr Val Gly Gly Val Glu Leu Pro Val
65                  70                  75                  80

Ala Ala Trp Arg Ser Tyr Leu Asn Met Glu Leu Thr Ile Pro Ile Phe
                85                  90                  95

Ala Thr Asn Ser Asp Cys Glu Leu Ile Val Lys Ala Met Gln Gly Leu
            100                 105                 110

Leu Lys Asp Gly Asn Pro Ile Pro Ser Ala Ile Ala Ala Asn Ser Gly
        115                 120                 125

Leu Tyr Gly Ala Met Ala Ser Asn Phe Thr Gln Phe Val Leu Val Asp
    130                 135                 140

Asn Gly Gly Thr Gly Asp Val Thr Val Ala Pro Ser Asn Phe Ala Asn
145                 150                 155                 160

Gly Val Ala Glu Trp Ile Ser Ser Asn Ser Arg Ser Gln Ala Tyr Lys
                165                 170                 175

Val Thr Cys Ser Val Arg Gln Ser Ser Ala Gln Asn Arg Lys Tyr Thr
            180                 185                 190

Ile Lys Val Glu Val Pro Lys Val Ala Thr Gln Thr Val Gly Gly Val
        195                 200                 205

Glu Leu Pro Val Ala Ala Trp Arg Ser Tyr Leu Asn Met Glu Leu Thr
    210                 215                 220

Ile Pro Ile Phe Ala Thr Asn Ser Asp Cys Glu Leu Ile Val Lys Ala
225                 230                 235                 240

Met Gln Gly Leu Leu Lys Asp Gly Asn Pro Ile Pro Ser Ala Ile Ala
                245                 250                 255

Ala Asn Ser Leu Ile Asn
            260


<210> SEQ ID NO 92
<211> LENGTH: 262
<212> TYPE: PRT
<213> ORGANISM: Artificial Sequence
<220> FEATURE:
<223> OTHER INFORMATION: Description of Artificial Sequence: Synthetic
      dimeric MS2 N55K mutant coat polypeptide

<400> SEQUENCE: 92

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Lys Arg Lys Tyr Thr Ile Lys Val Glu
```

```
    50                  55                  60

Val Pro Lys Val Ala Thr Gln Thr Val Gly Gly Val Glu Leu Pro Val
65                  70                  75                  80

Ala Ala Trp Arg Ser Tyr Leu Asn Met Glu Leu Thr Ile Pro Ile Phe
                85                  90                  95

Ala Thr Asn Ser Asp Cys Glu Leu Ile Val Lys Ala Met Gln Gly Leu
            100                 105                 110

Leu Lys Asp Gly Asn Pro Ile Pro Ser Ala Ile Ala Ala Asn Ser Gly
        115                 120                 125

Leu Tyr Gly Ala Met Ala Ser Asn Phe Thr Gln Phe Val Leu Val Asp
    130                 135                 140

Asn Gly Gly Thr Gly Asp Val Thr Val Ala Pro Ser Asn Phe Ala Asn
145                 150                 155                 160

Gly Val Ala Glu Trp Ile Ser Ser Asn Ser Arg Ser Gln Ala Tyr Lys
                165                 170                 175

Val Thr Cys Ser Val Arg Gln Ser Ser Ala Gln Lys Arg Lys Tyr Thr
            180                 185                 190

Ile Lys Val Glu Val Pro Lys Val Ala Thr Gln Thr Val Gly Gly Val
        195                 200                 205

Glu Leu Pro Val Ala Ala Trp Arg Ser Tyr Leu Asn Met Glu Leu Thr
    210                 215                 220

Ile Pro Ile Phe Ala Thr Asn Ser Asp Cys Glu Leu Ile Val Lys Ala
225                 230                 235                 240

Met Gln Gly Leu Leu Lys Asp Gly Asn Pro Ile Pro Ser Ala Ile Ala
                245                 250                 255

Ala Asn Ser Leu Ile Asn
            260


<210> SEQ ID NO 93
<211> LENGTH: 236
<212> TYPE: PRT
<213> ORGANISM: Artificial Sequence
<220> FEATURE:
<223> OTHER INFORMATION: Description of Artificial Sequence: Synthetic
      dimeric MS2 deltaFG mutant coat polypeptide

<400> SEQUENCE: 93

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Lys Arg Lys Tyr Thr Ile Lys Val Glu
    50                  55                  60

Val Pro Lys Gly Ala Trp Arg Ser Tyr Leu Asn Met Glu Leu Thr Ile
65                  70                  75                  80

Pro Ile Phe Ala Thr Asn Ser Asp Cys Glu Leu Ile Val Lys Ala Met
                85                  90                  95

Gln Gly Leu Leu Lys Asp Gly Asn Pro Ile Pro Ser Ala Ile Ala Ala
            100                 105                 110

Asn Ser Gly Leu Tyr Gly Ala Met Ala Ser Asn Phe Thr Gln Phe Val
        115                 120                 125

Leu Val Asp Asn Gly Gly Thr Gly Asp Val Thr Val Ala Pro Ser Asn
    130                 135                 140
```

```
Phe Ala Asn Gly Val Ala Glu Trp Ile Ser Ser Asn Ser Arg Ser Gln
145                 150                 155                 160

Ala Tyr Lys Val Thr Cys Ser Val Arg Gln Ser Ser Ala Gln Lys Arg
                165                 170                 175

Lys Tyr Thr Ile Lys Val Glu Val Pro Lys Gly Ala Trp Arg Ser Tyr
            180                 185                 190

Leu Asn Met Glu Leu Thr Ile Pro Ile Phe Ala Thr Asn Ser Asp Cys
        195                 200                 205

Glu Leu Ile Val Lys Ala Met Gln Gly Leu Leu Lys Asp Gly Asn Pro
    210                 215                 220

Ile Pro Ser Ala Ile Ala Ala Asn Ser Leu Ile Asn
225                 230                 235


<210> SEQ ID NO 94
<211> LENGTH: 22
<212> TYPE: PRT
<213> ORGANISM: Enterobacteria phage lambda

<400> SEQUENCE: 94

Met Asp Ala Gln Thr Arg Arg Arg Glu Arg Arg Ala Glu Lys Gln Ala
1               5                   10                  15

Gln Trp Lys Ala Ala Asn
            20


<210> SEQ ID NO 95
<211> LENGTH: 107
<212> TYPE: PRT
<213> ORGANISM: Enterobacteria phage lambda

<400> SEQUENCE: 95

Met Asp Ala Gln Thr Arg Arg Arg Glu Arg Arg Ala Glu Lys Gln Ala
1               5                   10                  15

Gln Trp Lys Ala Ala Asn Pro Leu Leu Val Gly Val Ser Ala Lys Pro
            20                  25                  30

Val Asn Arg Pro Ile Leu Ser Leu Asn Arg Lys Pro Lys Ser Arg Val
        35                  40                  45

Glu Ser Ala Leu Asn Pro Ile Asp Leu Thr Val Leu Ala Glu Tyr His
    50                  55                  60

Lys Gln Ile Glu Ser Asn Leu Gln Arg Ile Glu Arg Lys Asn Gln Arg
65                  70                  75                  80

Thr Trp Tyr Ser Lys Pro Gly Glu Arg Gly Ile Thr Cys Ser Gly Arg
                85                  90                  95

Gln Lys Ile Lys Gly Lys Ser Ile Pro Leu Ile
            100                 105


<210> SEQ ID NO 96
<211> LENGTH: 23
<212> TYPE: RNA
<213> ORGANISM: Enterobacteria phage lambda

<400> SEQUENCE: 96

aaacaugagg auuacccaug ucg                                              23


<210> SEQ ID NO 97
<211> LENGTH: 23
<212> TYPE: RNA
<213> ORGANISM: Artificial Sequence
<220> FEATURE:
<223> OTHER INFORMATION: Description of Artificial Sequence: Synthetic
      high affinity MS2 binding oligonucleotide
```

<400> SEQUENCE: 97
aaacaugagg aucacccaug ucg 23

<210> SEQ ID NO 98
<211> LENGTH: 15
<212> TYPE: RNA
<213> ORGANISM: Enterobacteria phage lambda

<400> SEQUENCE: 98
gcccugaaga agggc 15

<210> SEQ ID NO 99
<211> LENGTH: 15
<212> TYPE: RNA
<213> ORGANISM: Enterobacteria phage lambda

<400> SEQUENCE: 99
gcccugaaaa agggc 15

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic truncated Csy4 binding site oligonucleotide
<220> FEATURE:
<223> OTHER INFORMATION: Description of combined DNA/RNA molecule: Synthetic truncated Csy4 binding site oligonucleotide

<400> SEQUENCE: 100
gttcactgcc gtataggcag 20

<210> SEQ ID NO 101
<211> LENGTH: 28
<212> TYPE: RNA
<213> ORGANISM: Artificial Sequence
<220> FEATURE:
<223> OTHER INFORMATION: Description of Artificial Sequence: Synthetic Csy4 binding site oligonucleotide

<400> SEQUENCE: 101
guucacugcc guauaggcag cuaagaaa 28

<210> SEQ ID NO 102
<211> LENGTH: 32
<212> TYPE: RNA
<213> ORGANISM: Artificial Sequence
<220> FEATURE:
<223> OTHER INFORMATION: Description of Artificial Sequence: Synthetic crRNA oligonucleotide
<220> FEATURE:
<221> NAME/KEY: modified_base
<222> LOCATION: (1)..(20)
<223> OTHER INFORMATION: a, c, u, g, unknown or other and this region may encompass 17-20 nucleotides, wherein some positions may be absent

<400> SEQUENCE: 102
nnnnnnnnnn nnnnnnnnnn guuuuagagc ua 32

<210> SEQ ID NO 103
<211> LENGTH: 42
<212> TYPE: RNA
<213> ORGANISM: Artificial Sequence
<220> FEATURE:

<223> OTHER INFORMATION: Description of Artificial Sequence: Synthetic crRNA oligonucleotide
<220> FEATURE:
<221> NAME/KEY: modified_base
<222> LOCATION: (1)..(20)
<223> OTHER INFORMATION: a, c, u, g, unknown or other and this region may encompass 17-20 nucleotides, wherein some positions may be absent

<400> SEQUENCE: 103
nnnnnnnnnn nnnnnnnnnn guuuuagagc uaugcuguuu ug 42

<210> SEQ ID NO 104
<211> LENGTH: 36
<212> TYPE: RNA
<213> ORGANISM: Artificial Sequence
<220> FEATURE:
<223> OTHER INFORMATION: Description of Artificial Sequence: Synthetic crRNA oligonucleotide
<220> FEATURE:
<221> NAME/KEY: modified_base
<222> LOCATION: (1)..(20)
<223> OTHER INFORMATION: a, c, u, g, unknown or other and this region may encompass 17-20 nucleotides, wherein some positions may be absent

<400> SEQUENCE: 104
nnnnnnnnnn nnnnnnnnnn guuuuagagc uaugcu 36

<210> SEQ ID NO 105
<211> LENGTH: 60
<212> TYPE: RNA
<213> ORGANISM: Artificial Sequence
<220> FEATURE:
<223> OTHER INFORMATION: Description of Artificial Sequence: Synthetic tracrRNA oligonucleotide

<400> SEQUENCE: 105
uagcaaguua aaauaaggcu aguccguuau caacuugaaa aaguggcacc gagucggugc 60

<210> SEQ ID NO 106
<211> LENGTH: 64
<212> TYPE: RNA
<213> ORGANISM: Artificial Sequence
<220> FEATURE:
<223> OTHER INFORMATION: Description of Artificial Sequence: Synthetic tracrRNA oligonucleotide

<400> SEQUENCE: 106
agcauagcaa guuaaaauaa ggcuaguccg uuaucaacuu gaaaaagugg caccgagucg 60
gugc 64

<210> SEQ ID NO 107
<211> LENGTH: 2279
<212> TYPE: DNA
<213> ORGANISM: Artificial Sequence
<220> FEATURE:
<223> OTHER INFORMATION: Description of Artificial Sequence: Synthetic RNA expression vector polynucleotide
<220> FEATURE:
<221> NAME/KEY: modified_base
<222> LOCATION: (331)..(350)
<223> OTHER INFORMATION: a, c, t, g, unknown or other

<400> SEQUENCE: 107
gacgtcgcta gctgtacaaa aaagcaggct ttaaaggaac caattcagtc gactggatcc 60
ggtaccaagg tcgggcagga agagggccta tttcccatga ttccttcata tttgcatata 120

```
cgatacaagg ctgttagaga gataattaga attaatttga ctgtaaacac aaagatatta    180
gtacaaaata cgtgacgtag aaagtaataa tttcttgggt agtttgcagt tttaaaatta    240
tgttttaaaa tggactatca tatgcttacc gtaacttgaa agtatttcga tttcttggct    300
ttatatatct tgtggaaagg acgaaacacc nnnnnnnnnn nnnnnnnnnn gttttagagc    360
tagaaatagc aagttaaaat aaggctagtc cgttatcaac ttgaaaaagt ggcaccgagt    420
cggtgctttt tttaagcttg ggccgctcga ggtacctctc tacatatgac atgtgagcaa    480
aaggccagca aaaggccagg aaccgtaaaa aggccgcgtt gctggcgttt ttccataggc    540
tccgcccccc tgacgagcat cacaaaaatc gacgctcaag tcagaggtgg cgaaacccga    600
caggactata aagataccag gcgtttcccc ctggaagctc cctcgtgcgc tctcctgttc    660
cgaccctgcc gcttaccgga tacctgtccg cctttctccc ttcgggaagc gtggcgcttt    720
ctcatagctc acgctgtagg tatctcagtt cggtgtaggt cgttcgctcc aagctgggct    780
gtgtgcacga accccccgtt cagcccgacc gctgcgcctt atccggtaac tatcgtcttg    840
agtccaaccc ggtaagacac gacttatcgc cactggcagc agccactggt aacaggatta    900
gcagagcgag gtatgtaggc ggtgctacag agttcttgaa gtggtggcct aactacggct    960
acactagaag aacagtattt ggtatctgcg ctctgctgaa gccagttacc ttcggaaaaa   1020
gagttggtag ctcttgatcc ggcaaacaaa ccaccgctgg tagcggtggt ttttttgttt   1080
gcaagcagca gattacgcgc agaaaaaaag gatctcaaga agatcctttg atcttttcta   1140
cggggtctga cgctcagtgg aacgaaaact cacgttaagg gattttggtc atgagattat   1200
caaaaaggat cttcacctag atccttttaa attaaaaatg aagttttaaa tcaatctaaa   1260
gtatatatga gtaaacttgg tctgacagtt accaatgctt aatcagtgag gcacctatct   1320
cagcgatctg tctatttcgt tcatccatag ttgcctgact ccccgtcgtg tagataacta   1380
cgatacggga gggcttacca tctggcccca gtgctgcaat gataccgcga gacccacgct   1440
caccggctcc agatttatca gcaataaacc agccagccgg aagggccgag cgcagaagtg   1500
gtcctgcaac tttatccgcc tccatccagt ctattaattg ttgccgggaa gctagagtaa   1560
gtagttcgcc agttaatagt ttgcgcaacg ttgttgccat tgctacaggc atcgtggtgt   1620
cacgctcgtc gtttggtatg gcttcattca gctccggttc ccaacgatca aggcgagtta   1680
catgatcccc catgttgtgc aaaaaagcgg ttagctcctt cggtcctccg atcgttgtca   1740
gaagtaagtt ggccgcagtg ttatcactca tggttatggc agcactgcat aattctctta   1800
ctgtcatgcc atccgtaaga tgcttttctg tgactggtga gtactcaacc aagtcattct   1860
gagaatagtg tatgcggcga ccgagttgct cttgcccggc gtcaatacgg gataataccg   1920
cgccacatag cagaacttta aaagtgctca tcattggaaa acgttcttcg gggcgaaaac   1980
tctcaaggat cttaccgctg ttgagatcca gttcgatgta acccactcgt gcacccaact   2040
gatcttcagc atcttttact ttcaccagcg tttctgggtg agcaaaaaca ggaaggcaaa   2100
atgccgcaaa aaagggaata agggcgacac ggaaatgttg aatactcata ctcttccttt   2160
ttcaatatta ttgaagcatt tatcagggtt attgtctcat gagcggatac atatttgaat   2220
gtatttagaa aaataaacaa ataggggttc cgcgcacatt tccccgaaaa gtgccacct    2279
```

<210> SEQ ID NO 108
<211> LENGTH: 7786
<212> TYPE: DNA
<213> ORGANISM: Artificial Sequence
<220> FEATURE:
<223> OTHER INFORMATION: Description of Artificial Sequence: Synthetic CMV-T7-Cas9 D10A/H840A-3xFlag-VP64 polynucleotide

<400> SEQUENCE: 108

```
atatgccaag tacgccccct attgacgtca atgacggtaa atggcccgcc tggcattatg      60
cccagtacat gaccttatgg gactttccta cttggcagta catctacgta ttagtcatcg     120
ctattaccat ggtgatgcgg ttttggcagt acatcaatgg gcgtggatag cggtttgact     180
cacggggatt tccaagtctc caccccattg acgtcaatgg gagtttgttt tggcaccaaa     240
atcaacggga ctttccaaaa tgtcgtaaca actccgcccc attgacgcaa atgggcggta     300
ggcgtgtacg gtgggaggtc tatataagca gagctggttt agtgaaccgt cagatccgct     360
agagatccgc ggccgctaat acgactcact atagggagag ccgccaccat ggataagaaa     420
tactcaatag gcttagctat cggcacaaat agcgtcggat gggcggtgat cactgatgaa     480
tataaggttc cgtctaaaaa gttcaaggtt ctgggaaata cagaccgcca cagtatcaaa     540
aaaaatctta taggggctct tttatttgac agtggagaga cagcggaagc gactcgtctc     600
aaacggacag ctcgtagaag gtatacacgt cggaagaatc gtatttgtta tctacaggag     660
atttttcaa atgagatggc gaaagtagat gatagtttct ttcatcgact tgaagagtct      720
tttttggtgg aagaagacaa gaagcatgaa cgtcatccta tttttggaaa tatagtagat     780
gaagttgctt atcatgagaa atatccaact atctatcatc tgcgaaaaaa attggtagat     840
tctactgata aagcggattt gcgcttaatc tatttggcct tagcgcatat gattaagttt     900
cgtggtcatt ttttgattga gggagattta aatcctgata atagtgatgt ggacaaacta     960
tttatccagt tggtacaaac ctacaatcaa ttatttgaag aaaaccctat taacgcaagt    1020
ggagtagatg ctaaagcgat tctttctgca cgattgagta aatcaagacg attagaaaat    1080
ctcattgctc agctccccgg tgagaagaaa aatggcttat ttgggaatct cattgctttg    1140
tcattgggtt tgacccctaa ttttaaatca aattttgatt tggcagaaga tgctaaatta    1200
cagctttcaa aagatactta cgatgatgat ttagataatt tattggcgca aattggagat    1260
caatatgctg atttgttttt ggcagctaag aatttatcag atgctatttt actttcagat    1320
atcctaagag taaatactga aataactaag gctcccctat cagcttcaat gattaaacgc    1380
tacgatgaac atcatcaaga cttgactctt ttaaaagctt tagttcgaca acaacttcca    1440
gaaaagtata aagaaatctt ttttgatcaa tcaaaaaacg gatatgcagg ttatattgat    1500
gggggagcta gccaagaaga attttataaa tttatcaaac caattttaga aaaaatggat    1560
ggtactgagg aattattggt gaaactaaat cgtgaagatt tgctgcgcaa gcaacggacc    1620
tttgacaacg gctctattcc ccatcaaatt cacttgggtg agctgcatgc tattttgaga    1680
agacaagaag acttttatcc atttttaaaa gacaatcgtg agaagattga aaaaatcttg    1740
acttttcgaa ttccttatta tgttggtcca ttggcgcgtg gcaatagtcg ttttgcatgg    1800
atgactcgga agtctgaaga aacaattacc ccatggaatt ttgaagaagt tgtcgataaa    1860
ggtgcttcag ctcaatcatt tattgaacgc atgacaaact ttgataaaaa tcttccaaat    1920
gaaaaagtac taccaaaaca tagtttgctt tatgagtatt ttacggttta taacgaattg    1980
acaaaggtca aatatgttac tgaaggaatg cgaaaaccag catttctttc aggtgaacag    2040
aagaaagcca ttgttgattt actcttcaaa acaaatcgaa aagtaaccgt taagcaatta    2100
aaagaagatt atttcaaaaa aatagaatgt tttgatagtg ttgaaatttc aggagttgaa    2160
gatagattta atgcttcatt aggtacctac catgatttgc taaaaattat taaagataaa    2220
gatttttgg ataatgaaga aaatgaagat atcttagagg atattgtttt aacattgacc     2280
```

```
ttatttgaag atagggagat gattgaggaa agacttaaaa catatgctca cctctttgat   2340

gataaggtga tgaaacagct taaacgtcgc cgttatactg gttggggacg tttgtctcga   2400

aaattgatta atggtattag ggataagcaa tctggcaaaa caatattaga tttttttgaaa   2460

tcagatggtt ttgccaatcg caattttatg cagctgatcc atgatgatag tttgacattt   2520

aaagaagaca ttcaaaaagc acaagtgtct ggacaaggcg atagtttaca tgaacatatt   2580

gcaaatttag ctggtagccc tgctattaaa aaaggtattt tacagactgt aaaagttgtt   2640

gatgaattgg tcaaagtaat ggggcggcat aagccagaaa atatcgttat tgaaatggca   2700

cgtgaaaatc agacaactca aaagggccag aaaaattcgc gagagcgtat gaaacgaatc   2760

gaagaaggta tcaaagaatt aggaagtcag attcttaaag agcatcctgt tgaaaatact   2820

caattgcaaa atgaaaagct ctatctctat tatctccaaa atggaagaga catgtatgtg   2880

gaccaagaat tagatattaa tcgtttaagt gattatgatg tcgatgccat tgttccacaa   2940

agtttcctta aagacgattc aatagacaat aaggtcttaa cgcgttctga taaaaatcgt   3000

ggtaaatcgg ataacgttcc aagtgaagaa gtagtcaaaa agatgaaaaa ctattggaga   3060

caacttctaa acgccaagtt aatcactcaa cgtaagtttg ataatttaac gaaagctgaa   3120

cgtggaggtt tgagtgaact tgataaagct ggttttatca aacgccaatt ggttgaaact   3180

cgccaaatca ctaagcatgt ggcacaaatt ttggatagtc gcatgaatac taaatacgat   3240

gaaaatgata aacttattcg agaggttaaa gtgattacct taaaatctaa attagtttct   3300

gacttccgaa aagatttcca attctataaa gtacgtgaga ttaacaatta ccatcatgcc   3360

catgatgcgt atctaaatgc cgtcgttgga actgctttga ttaagaaata tccaaaactt   3420

gaatcggagt ttgtctatgg tgattataaa gtttatgatg ttcgtaaaat gattgctaag   3480

tctgagcaag aaataggcaa agcaaccgca aaatatttct tttactctaa tatcatgaac   3540

ttcttcaaaa cagaaattac acttgcaaat ggagagattc gcaaacgccc tctaatcgaa   3600

actaatgggg aaactggaga aattgtctgg gataaagggc gagattttgc cacagtgcgc   3660

aaagtattgt ccatgcccca agtcaatatt gtcaagaaaa cagaagtaca gacaggcgga   3720

ttctccaagg agtcaatttt accaaaaaga aattcggaca agcttattgc tcgtaaaaaa   3780

gactgggatc caaaaaaata tggtggtttt gatagtccaa cggtagctta ttcagtccta   3840

gtggttgcta aggtggaaaa agggaaatcg aagaagttaa aatccgttaa agagttacta   3900

gggatcacaa ttatggaaag aagttccttt gaaaaaaatc cgattgactt tttagaagct   3960

aaaggatata aggaagttaa aaaagactta atcattaaac tacctaaata tagtcttttt   4020

gagttagaaa acggtcgtaa acggatgctg gctagtgccg gagaattaca aaaaggaaat   4080

gagctggctc tgccaagcaa atatgtgaat tttttatatt tagctagtca ttatgaaaag   4140

ttgaagggta gtccagaaga taacgaacaa aaacaattgt ttgtggagca gcataagcat   4200

tatttagatg agattattga gcaaatcagt gaattttcta agcgtgttat tttagcagat   4260

gccaatttag ataaagttct tagtgcatat aacaaacata gagacaaacc aatacgtgaa   4320

caagcagaaa atattattca tttatttacg ttgacgaatc ttggagctcc cgctgctttt   4380

aaatattttg atacaacaat tgatcgtaaa cgatatacgt ctacaaaaga agttttagat   4440

gccactctta tccatcaatc catcactggt ctttatgaaa cacgcattga tttgagtcag   4500

ctaggaggtg acggttctcc caagaagaag aggaaagtct cgagcgacta caaagaccat   4560

gacggtgatt ataaagatca tgacatcgat tacaaggatg acgatgacaa ggctgcagga   4620
```

-continued

```
ggcggtggaa gcgggcgcgc cgacgcgctg gacgatttcg atctcgacat gctgggttct   4680
gatgccctcg atgactttga cctggatatg ttgggaagcg acgcattgga tgactttgat   4740
ctggacatgc tcggctccga tgctctggac gatttcgatc tcgatatgtt ataaccggtc   4800
atcatcacca tcaccattga gtttaaaccc gctgatcagc ctcgactgtg ccttctagtt   4860
gccagccatc tgttgtttgc ccctcccccg tgccttcctt gaccctggaa ggtgccactc   4920
ccactgtcct ttcctaataa aatgaggaaa ttgcatcgca ttgtctgagt aggtgtcatt   4980
ctattctggg gggtggggtg gggcaggaca gcaaggggga ggattgggaa gacaatagca   5040
ggcatgctgg ggatgcggtg ggctctatgg cttctgaggc ggaaagaacc agctggggct   5100
cgataccgtc gacctctagc tagagcttgg cgtaatcatg gtcatagctg tttcctgtgt   5160
gaaattgtta tccgctcaca attccacaca acatacgagc cggaagcata aagtgtaaag   5220
cctagggtgc ctaatgagtg agctaactca cattaattgc gttgcgctca ctgcccgctt   5280
tccagtcggg aaacctgtcg tgccagctgc attaatgaat cggccaacgc gcggggagag   5340
gcggtttgcg tattgggcgc tcttccgctt cctcgctcac tgactcgctg cgctcggtcg   5400
ttcggctgcg gcgagcggta tcagctcact caaaggcggt aatacggtta tccacagaat   5460
caggggataa cgcaggaaag aacatgtgag caaaaggcca gcaaaaggcc aggaaccgta   5520
aaaaggccgc gttgctggcg tttttccata ggctccgccc ccctgacgag catcacaaaa   5580
atcgacgctc aagtcagagg tggcgaaacc cgacaggact ataaagatac caggcgtttc   5640
cccctggaag ctccctcgtg cgctctcctg ttccgaccct gccgcttacc ggatacctgt   5700
ccgcctttct cccttcggga agcgtggcgc tttctcaatg ctcacgctgt aggtatctca   5760
gttcggtgta ggtcgttcgc tccaagctgg gctgtgtgca cgaacccccc gttcagcccg   5820
accgctgcgc cttatccggt aactatcgtc ttgagtccaa cccggtaaga cacgacttat   5880
cgccactggc agcagccact ggtaacagga ttagcagagc gaggtatgta ggcggtgcta   5940
cagagttctt gaagtggtgg cctaactacg gctacactag aaggacagta tttggtatct   6000
gcgctctgct gaagccagtt accttcggaa aaagagttgg tagctcttga tccggcaaac   6060
aaaccaccgc tggtagcggt ggtttttttg tttgcaagca gcagattacg cgcagaaaaa   6120
aaggatctca agaagatcct ttgatctttt ctacggggtc tgacgctcag tggaacgaaa   6180
actcacgtta agggattttg gtcatgagat tatcaaaaag gatcttcacc tagatccttt   6240
taaattaaaa atgaagtttt aaatcaatct aaagtatata tgagtaaact tggtctgaca   6300
gttaccaatg cttaatcagt gaggcaccta tctcagcgat ctgtctattt cgttcatcca   6360
tagttgcctg actccccgtc gtgtagataa ctacgatacg ggagggctta ccatctggcc   6420
ccagtgctgc aatgataccg cgagacccac gctcaccggc tccagattta tcagcaataa   6480
accagccagc cggaagggcc gagcgcagaa gtggtcctgc aactttatcc gcctccatcc   6540
agtctattaa ttgttgccgg gaagctagag taagtagttc gccagttaat agtttgcgca   6600
acgttgttgc cattgctaca ggcatcgtgg tgtcacgctc gtcgtttggt atggcttcat   6660
tcagctccgg ttcccaacga tcaaggcgag ttacatgatc ccccatgttg tgcaaaaaag   6720
cggttagctc cttcggtcct ccgatcgttg tcagaagtaa gttggccgca gtgttatcac   6780
tcatggttat ggcagcactg cataattctc ttactgtcat gccatccgta agatgctttt   6840
ctgtgactgg tgagtactca accaagtcat tctgagaata gtgtatgcgg cgaccgagtt   6900
gctcttgccc ggcgtcaata cgggataata ccgcgccaca tagcagaact ttaaaagtgc   6960
tcatcattgg aaaacgttct tcggggcgaa aactctcaag gatcttaccg ctgttgagat   7020
```

ccagttcgat gtaacccact cgtgcaccca actgatcttc agcatctttt actttcacca 7080
gcgtttctgg gtgagcaaaa acaggaaggc aaaatgccgc aaaaaaggga ataagggcga 7140
cacggaaatg ttgaatactc atactcttcc tttttcaata ttattgaagc atttatcagg 7200
gttattgtct catgagcgga tacatatttg aatgtattta gaaaaataaa caaatagggg 7260
ttccgcgcac atttccccga aaagtgccac ctgacgtcga cggatcggga gatcgatctc 7320
ccgatcccct agggtcgact ctcagtacaa tctgctctga tgccgcatag ttaagccagt 7380
atctgctccc tgcttgtgtg ttggaggtcg ctgagtagtg cgcgagcaaa atttaagcta 7440
caacaaggca aggcttgacc gacaattgca tgaagaatct gcttagggtt aggcgttttg 7500
cgctgcttcg cgatgtacgg gccagatata cgcgttgaca ttgattattg actagttatt 7560
aatagtaatc aattacgggg tcattagttc atagcccata tatggagttc cgcgttacat 7620
aacttacggt aaatggcccg cctggctgac cgcccaacga cccccgccca ttgacgtcaa 7680
taatgacgta tgttcccata gtaacgccaa tagggacttt ccattgacgt caatgggtgg 7740
actatttacg gtaaactgcc cacttggcag tacatcaagt gtatcc 7786

<210> SEQ ID NO 109
<211> LENGTH: 7785
<212> TYPE: DNA
<213> ORGANISM: Artificial Sequence
<220> FEATURE:
<223> OTHER INFORMATION: Description of Artificial Sequence: Synthetic
MV-T7-Cas9 recoded D10A/H840A-3xFLAG-VP64 polynucleotide

<400> SEQUENCE: 109
atatgccaag tacgccccct attgacgtca atgacggtaa atggcccgcc tggcattatg 60
cccagtacat gaccttatgg gactttccta cttggcagta catctacgta ttagtcatcg 120
ctattaccat ggtgatgcgg ttttggcagt acatcaatgg gcgtggatag cggtttgact 180
cacggggatt tccaagtctc caccccattg acgtcaatgg gagtttgttt tggcaccaaa 240
atcaacggga ctttccaaaa tgtcgtaaca actccgcccc attgacgcaa atgggcggta 300
ggcgtgtacg gtgggaggtc tatataagca gagctggttt agtgaaccgt cagatccgct 360
agagatccgc ggccgctaat acgactcact atagggagag ccgccaccat ggataaaaag 420
tattctattg gtttagccat cggcactaat tccgttggat gggctgtcat aaccgatgaa 480
tacaaagtac cttcaaagaa atttaaggtg ttggggaaca cagaccgtca ttcgattaaa 540
aagaatctta tcggtgccct cctattcgat agtggcgaaa cggcagaggc gactcgcctg 600
aaacgaaccg ctcggagaag gtatacacgt cgcaagaacc gaatatgtta cttacaagaa 660
atttttagca atgagatggc caaagttgac gattctttct ttcaccgttt ggaagagtcc 720
ttccttgtcg aagaggacaa gaaacatgaa cggcacccca tctttggaaa catagtagat 780
gaggtggcat atcatgaaaa gtacccaacg atttatcacc tcagaaaaaa gctagttgac 840
tcaactgata aagcggacct gaggttaatc tacttggctc ttgcccatat gataaagttc 900
cgtgggcact ttctcattga gggtgatcta aatccggaca actcggatgt cgacaaactg 960
ttcatccagt tagtacaaac ctataatcag ttgtttgaag agaaccctat aaatgcaagt 1020
ggcgtggatg cgaaggctat tcttagcgcc cgcctctcta aatcccgacg gctagaaaac 1080
ctgatcgcac aattacccgg agagaagaaa aatgggttgt tcggtaacct tatagcgctc 1140
tcactaggcc tgacaccaaa ttttaagtcg aacttcgact tagctgaaga tgccaaattg 1200
cagcttagta aggacacgta cgatgacgat ctcgacaatc tactggcaca aattggagat 1260

-continued

```
cagtatgcgg acttattttt ggctgccaaa aaccttagcg atgcaatcct cctatctgac   1320
atactgagag ttaatactga gattaccaag gcgccgttat ccgcttcaat gatcaaaagg   1380
tacgatgaac atcaccaaga cttgacactt ctcaaggccc tagtccgtca gcaactgcct   1440
gagaaatata aggaaatatt ctttgatcag tcgaaaaacg ggtacgcagg ttatattgac   1500
ggcggagcga gtcaagagga attctacaag tttatcaaac ccatattaga gaagatggat   1560
gggacggaag agttgcttgt aaaactcaat cgcgaagatc tactgcgaaa gcagcggact   1620
ttcgacaacg gtagcattcc acatcaaatc cacttaggcg aattgcatgc tatacttaga   1680
aggcaggagg atttttatcc gttcctcaaa gacaatcgtg aaaagattga gaaaatccta   1740
acctttcgca taccttacta tgtgggaccc ctggcccgag ggaactctcg gttcgcatgg   1800
atgacaagaa agtccgaaga aacgattact ccatggaatt ttgaggaagt tgtcgataaa   1860
ggtgcgtcag ctcaatcgtt catcgagagg atgaccaact ttgacaagaa tttaccgaac   1920
gaaaaagtat tgcctaagca cagtttactt tacgagtatt tcacagtgta caatgaactc   1980
acgaaagtta agtatgtcac tgagggcatg cgtaaacccg cctttctaag cggagaacag   2040
aagaaagcaa tagtagatct gttattcaag accaaccgca aagtgacagt taagcaattg   2100
aaagaggact actttaagaa aattgaatgc ttcgattctg tcgagatctc cggggtagaa   2160
gatcgattta atgcgtcact tggtacgtat catgacctcc taaagataat taaagataag   2220
gacttcctgg ataacgaaga gaatgaagat atcttagaag atatagtgtt gactcttacc   2280
ctctttgaag atcgggaaat gattgaggaa agactaaaaa catacgctca cctgttcgac   2340
gataaggtta tgaaacagtt aaagaggcgt cgctatacgg gctggggacg attgtcgcgg   2400
aaacttatca acgggataag agacaagcaa agtggtaaaa ctattctcga ttttctaaag   2460
agcgacggct tcgccaatag gaactttatg cagctgatcc atgatgactc tttaaccttc   2520
aaagaggata tacaaaaggc acaggtttcc ggacaagggg actcattgca cgaacatatt   2580
gcgaatcttg ctggttcgcc agccatcaaa aagggcatac tccagacagt caaagtagtg   2640
gatgagctag ttaaggtcat gggacgtcac aaaccggaaa acattgtaat cgagatggca   2700
cgcgaaaatc aaacgactca gaaggggcaa aaaaacagtc gagagcggat gaagagaata   2760
gaagagggta ttaaagaact gggcagccag atcttaaagg agcatcctgt ggaaaatacc   2820
caattgcaga acgagaaact ttacctctat tacctacaaa atggaaggga catgtatgtt   2880
gatcaggaac tggacataaa ccgtttatct gattacgacg tcgatgccat tgtaccccaa   2940
tcctttttga aggacgattc aatcgacaat aaagtgctta cacgctcgga taagaaccga   3000
gggaaaagtg acaatgttcc aagcgaggaa gtcgtaaaga aaatgaagaa ctattggcgg   3060
cagctcctaa atgcgaaact gataacgcaa agaaagttcg ataacttaac taaagctgag   3120
aggggtggct tgtctgaact tgacaaggcc ggatttatta aacgtcagct cgtggaaacc   3180
cgccaaatca caaagcatgt tgcacagata ctagattccc gaatgaatac gaaatacgac   3240
gagaacgata agctgattcg ggaagtcaaa gtaatcactt taaagtcaaa attggtgtcg   3300
gacttcagaa aggattttca attctataaa gttagggaga taaataacta ccaccatgcg   3360
cacgacgctt atcttaatgc cgtcgtaggg accgcactca ttaagaaata cccgaagcta   3420
gaaagtgagt ttgtgtatgg tgattacaaa gtttatgacg tccgtaagat gatcgcgaaa   3480
agcgaacagg agataggcaa ggctacagcc aaatacttct tttattctaa cattatgaat   3540
ttctttaaga cggaaatcac tctggcaaac ggagagatac gcaaacgacc tttaattgaa   3600
```

```
accaatgggg agacaggtga aatcgtatgg gataagggcc gggacttcgc gacggtgaga   3660
aaagttttgt ccatgcccca agtcaacata gtaaagaaaa ctgaggtgca gaccggaggg   3720
ttttcaaagg aatcgattct tccaaaaagg aatagtgata agctcatcgc tcgtaaaaag   3780
gactgggacc cgaaaaagta cggtggcttc gatagcccta cagttgccta ttctgtccta   3840
gtagtggcaa aagttgagaa gggaaaatcc aagaaactga agtcagtcaa agaattattg   3900
gggataacga ttatggagcg ctcgtctttt gaaaagaacc ccatcgactt ccttgaggcg   3960
aaaggttaca aggaagtaaa aaaggatctc ataattaaac taccaaagta tagtctgttt   4020
gagttagaaa atggccgaaa acggatgttg gctagcgccg gagagcttca aaaggggaac   4080
gaactcgcac taccgtctaa atacgtgaat ttcctgtatt tagcgtccca ttacgagaag   4140
ttgaaaggtt cacctgaaga taacgaacag aagcaacttt ttgttgagca gcacaaacat   4200
tatctcgacg aaatcataga gcaaatttcg gaattcagta agagagtcat cctagctgat   4260
gccaatctgg acaaagtatt aagcgcatac aacaagcaca gggataaacc catacgtgag   4320
caggcggaaa atattatcca tttgtttact cttaccaacc tcggcgctcc agccgcattc   4380
aagtattttg acacaacgat agatcgcaaa cgatacactt ctaccaagga ggtgctagac   4440
gcgacactga ttcaccaatc catcacggga ttatatgaaa ctcggataga tttgtcacag   4500
cttgggggtg acggatcccc caagaagaag aggaaagtct cgagcgacta caaagaccat   4560
gacggtgatt ataaagatca tgacatcgat tacaaggatg acgatgacaa ggctgcagga   4620
ggcggtggaa gcgggcgcgc cgacgcgctg gacgatttcg atctcgacat gctgggttct   4680
gatgccctcg atgactttga cctggatatg ttgggaagcg acgcattgga tgactttgat   4740
ctggacatgc tcggctccga tgctctggac gatttcgatc tcgatatgtt ataaccggtc   4800
atcatcacca tcaccattga gtttaaaccc gctgatcagc ctcgactgtg ccttctagtt   4860
gccagccatc tgttgtttgc ccctcccccg tgccttcctt gaccctggaa ggtgccactc   4920
ccactgtcct ttcctaataa aatgaggaaa ttgcatcgca ttgtctgagt aggtgtcatt   4980
ctattctggg gggtggggtg gggcaggaca gcaaggggga ggattgggaa gacaatagca   5040
ggcatgctgg ggatgcggtg ggctctatgg cttctgaggc ggaaagaacc agctggggct   5100
cgataccgtc gacctctagc tagagcttgg cgtaatcatg gtcatagctg tttcctgtgt   5160
gaaattgtta tccgctcaca attccacaca acatacgagc cggaagcata aagtgtaaag   5220
cctagggtgc ctaatgagtg agctaactca cattaattgc gttgcgctca ctgcccgctt   5280
tccagtcggg aaacctgtcg tgccagctgc attaatgaat cggccaacgc gcggggagag   5340
gcggtttgcg tattgggcgc tcttccgctt cctcgctcac tgactcgctg cgctcggtcg   5400
ttcggctgcg gcgagcggta tcagctcact caaaggcggt aatacggtta tccacagaat   5460
caggggataa cgcaggaaag aacatgtgag caaaaggcca gcaaaaggcc aggaaccgta   5520
aaaaggccgc gttgctggcg tttttccata ggctccgccc ccctgacgag catcacaaaa   5580
atcgacgctc aagtcagagg tggcgaaacc cgacaggact ataaagatac caggcgtttc   5640
cccctggaag ctccctcgtg cgctctcctg ttccgaccct gccgcttacc ggatacctgt   5700
ccgcctttct cccttcggga agcgtggcgc tttctcaatg ctcacgctgt aggtatctca   5760
gttcggtgta ggtcgttcgc tccaagctgg gctgtgtgca cgaacccccc gttcagcccg   5820
accgctgcgc cttatccggt aactatcgtc ttgagtccaa cccggtaaga cacgacttat   5880
cgccactggc agcagccact ggtaacagga ttagcagagc gaggtatgta ggcggtgcta   5940
cagagttctt gaagtggtgg cctaactacg gctacactag aaggacagta tttggtatct   6000
```

```
gcgctctgct gaagccagtt accttcggaa aaagagttgg tagctcttga tccggcaaac   6060

aaaccaccgc tggtagcggt ggtttttttg tttgcaagca gcagattacg cgcagaaaaa   6120

aaggatctca agaagatcct ttgatctttt ctacggggtc tgacgctcag tggaacgaaa   6180

actcacgtta agggattttg gtcatgagat tatcaaaaag gatcttcacc tagatccttt   6240

taaattaaaa atgaagtttt aaatcaatct aaagtatata tgagtaaact tggtctgaca   6300

gttaccaatg cttaatcagt gaggcaccta tctcagcgat ctgtctattt cgttcatcca   6360

tagttgcctg actccccgtc gtgtagataa ctacgatacg ggagggctta ccatctggcc   6420

ccagtgctgc aatgataccg cgagacccac gctcaccggc tccagattta tcagcaataa   6480

accagccagc cggaagggcc gagcgcagaa gtggtcctgc aactttatcc gcctccatcc   6540

agtctattaa ttgttgccgg gaagctagag taagtagttc gccagttaat agtttgcgca   6600

acgttgttgc cattgctaca ggcatcgtgg tgtcacgctc gtcgtttggt atggcttcat   6660

tcagctccgg ttcccaacga tcaaggcgag ttacatgatc ccccatgttg tgcaaaaaag   6720

cggttagctc cttcggtcct ccgatcgttg tcagaagtaa gttggccgca gtgttatcac   6780

tcatggttat ggcagcactg cataattctc ttactgtcat gccatccgta agatgctttt   6840

ctgtgactgg tgagtactca accaagtcat tctgagaata gtgtatgcgg cgaccgagtt   6900

gctcttgccc ggcgtcaata cgggataata ccgcgccaca tagcagaact ttaaaagtgc   6960

tcatcattgg aaaacgttct tcggggcgaa aactctcaag gatcttaccg ctgttgagat   7020

ccagttcgat gtaacccact cgtgcaccca actgatcttc agcatctttt actttcacca   7080

gcgtttctgg gtgagcaaaa acaggaaggc aaaatgccgc aaaaaaggga ataagggcga   7140

cacggaaatg ttgaatactc atactcttcc tttttcaata ttattgaagc atttatcagg   7200

gttattgtct catgagcgga tacatatttg aatgtattta gaaaaataaa caaatagggg   7260

ttccgcgcac atttccccga aaagtgccac ctgacgtcga cggatcggga gatcgatctc   7320

ccgatcccct agggtcgact ctcagtacaa tctgctctga tgccgcatag ttaagccagt   7380

atctgctccc tgcttgtgtg ttggaggtcg ctgagtagtg cgcgagcaaa atttaagcta   7440

caacaaggca aggcttgacc gacaattgca tgaagaatct gcttagggtt aggcgttttg   7500

cgctgcttcg cgatgtacgg gccagatata cgcgttgaca ttgattattg actagttatt   7560

aatagtaatc aattacgggg tcattagttc atagcccata tatggagttc cgcgttacat   7620

aacttacggt aaatggcccg cctggctgac cgcccaacga cccccgccca ttgacgtcaa   7680

taatgacgta tgttcccata gtaacgccaa tagggacttt ccattgacgt caatgggtgg   7740

actatttacg gtaaactgcc cacttggcag tacatcaagt gtatc                   7785
```

<210> SEQ ID NO 110
<211> LENGTH: 1461
<212> TYPE: PRT
<213> ORGANISM: Artificial Sequence
<220> FEATURE:
<223> OTHER INFORMATION: Description of Artificial Sequence: Synthetic Cas9-activator polypeptide

<400> SEQUENCE: 110

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
```

-continued

```
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460
```

-continued

```
Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880
```

```
Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                 1015                1020

Lys Ser  Glu Gln Glu Ile Gly  Lys Ala Thr Ala Lys  Tyr Phe Phe
    1025                 1030                1035

Tyr Ser  Asn Ile Met Asn Phe  Phe Lys Thr Glu Ile  Thr Leu Ala
    1040                 1045                1050

Asn Gly  Glu Ile Arg Lys Arg  Pro Leu Ile Glu Thr  Asn Gly Glu
    1055                 1060                1065

Thr Gly  Glu Ile Val Trp Asp  Lys Gly Arg Asp Phe  Ala Thr Val
    1070                 1075                1080

Arg Lys  Val Leu Ser Met Pro  Gln Val Asn Ile Val  Lys Lys Thr
    1085                 1090                1095

Glu Val  Gln Thr Gly Gly Phe  Ser Lys Glu Ser Ile  Leu Pro Lys
    1100                 1105                1110

Arg Asn  Ser Asp Lys Leu Ile  Ala Arg Lys Lys Asp  Trp Asp Pro
    1115                 1120                1125

Lys Lys  Tyr Gly Gly Phe Asp  Ser Pro Thr Val Ala  Tyr Ser Val
    1130                 1135                1140

Leu Val  Val Ala Lys Val Glu  Lys Gly Lys Ser Lys  Lys Leu Lys
    1145                 1150                1155

Ser Val  Lys Glu Leu Leu Gly  Ile Thr Ile Met Glu  Arg Ser Ser
    1160                 1165                1170

Phe Glu  Lys Asn Pro Ile Asp  Phe Leu Glu Ala Lys  Gly Tyr Lys
    1175                 1180                1185

Glu Val  Lys Lys Asp Leu Ile  Ile Lys Leu Pro Lys  Tyr Ser Leu
    1190                 1195                1200

Phe Glu  Leu Glu Asn Gly Arg  Lys Arg Met Leu Ala  Ser Ala Gly
    1205                 1210                1215

Glu Leu  Gln Lys Gly Asn Glu  Leu Ala Leu Pro Ser  Lys Tyr Val
    1220                 1225                1230

Asn Phe  Leu Tyr Leu Ala Ser  His Tyr Glu Lys Leu  Lys Gly Ser
    1235                 1240                1245

Pro Glu  Asp Asn Glu Gln Lys  Gln Leu Phe Val Glu  Gln His Lys
    1250                 1255                1260

His Tyr  Leu Asp Glu Ile Ile  Glu Gln Ile Ser Glu  Phe Ser Lys
    1265                 1270                1275

Arg Val  Ile Leu Ala Asp Ala  Asn Leu Asp Lys Val  Leu Ser Ala
```

```
    1280                1285                1290

Tyr Asn  Lys His Arg Asp Lys  Pro Ile Arg Glu Gln  Ala Glu Asn
    1295                1300                1305

Ile Ile  His Leu Phe Thr Leu  Thr Asn Leu Gly Ala  Pro Ala Ala
    1310                1315                1320

Phe Lys  Tyr Phe Asp Thr Thr  Ile Asp Arg Lys Arg  Tyr Thr Ser
    1325                1330                1335

Thr Lys  Glu Val Leu Asp Ala  Thr Leu Ile His Gln  Ser Ile Thr
    1340                1345                1350

Gly Leu  Tyr Glu Thr Arg Ile  Asp Leu Ser Gln Leu  Gly Gly Asp
    1355                1360                1365

Gly Ser  Pro Lys Lys Lys Arg  Lys Val Ser Ser Asp  Tyr Lys Asp
    1370                1375                1380

His Asp  Gly Asp Tyr Lys Asp  His Asp Ile Asp Tyr  Lys Asp Asp
    1385                1390                1395

Asp Asp  Lys Ala Ala Gly Gly  Gly Gly Ser Gly Arg  Ala Asp Ala
    1400                1405                1410

Leu Asp  Asp Phe Asp Leu Asp  Met Leu Gly Ser Asp  Ala Leu Asp
    1415                1420                1425

Asp Phe  Asp Leu Asp Met Leu  Gly Ser Asp Ala Leu  Asp Asp Phe
    1430                1435                1440

Asp Leu  Asp Met Leu Gly Ser  Asp Ala Leu Asp Asp  Phe Asp Leu
    1445                1450                1455

Asp Met  Leu
    1460


<210> SEQ ID NO 111
<211> LENGTH: 1527
<212> TYPE: PRT
<213> ORGANISM: Artificial Sequence
<220> FEATURE:
<223> OTHER INFORMATION: Description of Artificial Sequence: Synthetic
      dCas9-NLS-3xFLAG-HP1alpha polypeptide

<400> SEQUENCE: 111

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160
```

-continued

```
Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
                180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
```

-continued

```
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005
```

```
Val Tyr  Gly Asp Tyr Lys Val  Tyr Asp Val Arg Lys  Met Ile Ala
    1010                 1015                 1020

Lys Ser  Glu Gln Glu Ile Gly  Lys Ala Thr Ala Lys  Tyr Phe Phe
    1025                 1030                 1035

Tyr Ser  Asn Ile Met Asn Phe  Phe Lys Thr Glu Ile  Thr Leu Ala
    1040                 1045                 1050

Asn Gly  Glu Ile Arg Lys Arg  Pro Leu Ile Glu Thr  Asn Gly Glu
    1055                 1060                 1065

Thr Gly  Glu Ile Val Trp Asp  Lys Gly Arg Asp Phe  Ala Thr Val
    1070                 1075                 1080

Arg Lys  Val Leu Ser Met Pro  Gln Val Asn Ile Val  Lys Lys Thr
    1085                 1090                 1095

Glu Val  Gln Thr Gly Gly Phe  Ser Lys Glu Ser Ile  Leu Pro Lys
    1100                 1105                 1110

Arg Asn  Ser Asp Lys Leu Ile  Ala Arg Lys Lys Asp  Trp Asp Pro
    1115                 1120                 1125

Lys Lys  Tyr Gly Gly Phe Asp  Ser Pro Thr Val Ala  Tyr Ser Val
    1130                 1135                 1140

Leu Val  Val Ala Lys Val Glu  Lys Gly Lys Ser Lys  Lys Leu Lys
    1145                 1150                 1155

Ser Val  Lys Glu Leu Leu Gly  Ile Thr Ile Met Glu  Arg Ser Ser
    1160                 1165                 1170

Phe Glu  Lys Asn Pro Ile Asp  Phe Leu Glu Ala Lys  Gly Tyr Lys
    1175                 1180                 1185

Glu Val  Lys Lys Asp Leu Ile  Ile Lys Leu Pro Lys  Tyr Ser Leu
    1190                 1195                 1200

Phe Glu  Leu Glu Asn Gly Arg  Lys Arg Met Leu Ala  Ser Ala Gly
    1205                 1210                 1215

Glu Leu  Gln Lys Gly Asn Glu  Leu Ala Leu Pro Ser  Lys Tyr Val
    1220                 1225                 1230

Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365

Gly Ser  Pro Lys Lys Lys Arg  Lys Val Ser Ser Asp  Tyr Lys Asp
    1370                 1375                 1380

His Asp  Gly Asp Tyr Lys Asp  His Asp Ile Asp Tyr  Lys Asp Asp
    1385                 1390                 1395
```

```
Asp Asp  Lys Ala Ala Gly Gly  Gly Gly Ser Met Lys  Glu Gly Glu
    1400                 1405                 1410

Asn Asn  Lys Pro Arg Glu Lys  Ser Glu Ser Asn Lys  Arg Lys Ser
    1415                 1420                 1425

Asn Phe  Ser Asn Ser Ala Asp  Asp Ile Lys Ser Lys  Lys Lys Arg
    1430                 1435                 1440

Glu Gln  Ser Asn Asp Ile Ala  Arg Gly Phe Glu Arg  Gly Leu Glu
    1445                 1450                 1455

Pro Glu  Lys Ile Ile Gly Ala  Thr Asp Ser Cys Gly  Asp Leu Met
    1460                 1465                 1470

Phe Leu  Met Lys Trp Lys Asp  Thr Asp Glu Ala Asp  Leu Val Leu
    1475                 1480                 1485

Ala Lys  Glu Ala Asn Val Lys  Cys Pro Gln Ile Val  Ile Ala Phe
    1490                 1495                 1500

Tyr Glu  Glu Arg Leu Thr Trp  His Ala Tyr Pro Glu  Asp Ala Glu
    1505                 1510                 1515

Asn Lys  Glu Lys Glu Thr Ala  Lys Ser
    1520                 1525


<210> SEQ ID NO 112
<211> LENGTH: 1521
<212> TYPE: PRT
<213> ORGANISM: Artificial Sequence
<220> FEATURE:
<223> OTHER INFORMATION: Description of Artificial Sequence: Synthetic
      dCas9-NLS-3xFLAG-HP1beta polypeptide

<400> SEQUENCE: 112

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220
```

```
Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640
```

```
His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
```

```
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110

Arg Asn  Ser Asp Lys Leu Ile  Ala Arg Lys Lys Asp  Trp Asp Pro
    1115                1120                1125

Lys Lys  Tyr Gly Gly Phe Asp  Ser Pro Thr Val Ala  Tyr Ser Val
    1130                1135                1140

Leu Val  Val Ala Lys Val Glu  Lys Gly Lys Ser Lys  Lys Leu Lys
    1145                1150                1155

Ser Val  Lys Glu Leu Leu Gly  Ile Thr Ile Met Glu  Arg Ser Ser
    1160                1165                1170

Phe Glu  Lys Asn Pro Ile Asp  Phe Leu Glu Ala Lys  Gly Tyr Lys
    1175                1180                1185

Glu Val  Lys Lys Asp Leu Ile  Ile Lys Leu Pro Lys  Tyr Ser Leu
    1190                1195                1200

Phe Glu  Leu Glu Asn Gly Arg  Lys Arg Met Leu Ala  Ser Ala Gly
    1205                1210                1215

Glu Leu  Gln Lys Gly Asn Glu  Leu Ala Leu Pro Ser  Lys Tyr Val
    1220                1225                1230

Asn Phe  Leu Tyr Leu Ala Ser  His Tyr Glu Lys Leu  Lys Gly Ser
    1235                1240                1245

Pro Glu  Asp Asn Glu Gln Lys  Gln Leu Phe Val Glu  Gln His Lys
    1250                1255                1260

His Tyr  Leu Asp Glu Ile Ile  Glu Gln Ile Ser Glu  Phe Ser Lys
    1265                1270                1275

Arg Val  Ile Leu Ala Asp Ala  Asn Leu Asp Lys Val  Leu Ser Ala
    1280                1285                1290

Tyr Asn  Lys His Arg Asp Lys  Pro Ile Arg Glu Gln  Ala Glu Asn
    1295                1300                1305

Ile Ile  His Leu Phe Thr Leu  Thr Asn Leu Gly Ala  Pro Ala Ala
    1310                1315                1320

Phe Lys  Tyr Phe Asp Thr Thr  Ile Asp Arg Lys Arg  Tyr Thr Ser
    1325                1330                1335

Thr Lys  Glu Val Leu Asp Ala  Thr Leu Ile His Gln  Ser Ile Thr
    1340                1345                1350

Gly Leu  Tyr Glu Thr Arg Ile  Asp Leu Ser Gln Leu  Gly Gly Asp
    1355                1360                1365

Gly Ser  Pro Lys Lys Lys Arg  Lys Val Ser Ser Asp  Tyr Lys Asp
    1370                1375                1380

His Asp  Gly Asp Tyr Lys Asp  His Asp Ile Asp Tyr  Lys Asp Asp
    1385                1390                1395

Asp Asp  Lys Ala Ala Gly Gly  Gly Gly Ser Thr Ala  His Glu Thr
    1400                1405                1410

Asp Lys  Ser Glu Gly Gly Lys  Arg Lys Ala Asp Ser  Asp Ser Glu
    1415                1420                1425

Asp Lys  Gly Glu Glu Ser Lys  Pro Lys Lys Lys Lys  Glu Glu Ser
    1430                1435                1440

Glu Lys  Pro Arg Gly Phe Ala  Arg Gly Leu Glu Pro  Glu Arg Ile
    1445                1450                1455
```

```
Ile Gly  Ala Thr Asp Ser Ser  Gly Glu Leu Met Phe  Leu Met Lys
    1460                 1465                 1470

Trp Lys  Asn Ser Asp Glu Ala  Asp Leu Val Pro Ala  Lys Glu Ala
    1475                 1480                 1485

Asn Val  Lys Cys Pro Gln Val  Val Ile Ser Phe Tyr  Glu Glu Arg
    1490                 1495                 1500

Leu Thr  Trp His Ser Tyr Pro  Ser Glu Asp Asp Asp  Lys Lys Asp
    1505                 1510                 1515

Asp Lys  Asn
    1520


<210> SEQ ID NO 113
<211> LENGTH: 2126
<212> TYPE: PRT
<213> ORGANISM: Artificial Sequence
<220> FEATURE:
<223> OTHER INFORMATION: Description of Artificial Sequence: Synthetic
      dCas9-3xFLAG-TET1CD polypeptide

<400> SEQUENCE: 113

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
```

```
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700
```

```
Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110
```

-continued

```
Arg Asn  Ser Asp Lys Leu Ile  Ala Arg Lys Lys Asp  Trp Asp Pro
    1115                 1120                 1125

Lys Lys  Tyr Gly Gly Phe Asp  Ser Pro Thr Val Ala  Tyr Ser Val
    1130                 1135                 1140

Leu Val  Val Ala Lys Val Glu  Lys Gly Lys Ser Lys  Lys Leu Lys
    1145                 1150                 1155

Ser Val  Lys Glu Leu Leu Gly  Ile Thr Ile Met Glu  Arg Ser Ser
    1160                 1165                 1170

Phe Glu  Lys Asn Pro Ile Asp  Phe Leu Glu Ala Lys  Gly Tyr Lys
    1175                 1180                 1185

Glu Val  Lys Lys Asp Leu Ile  Ile Lys Leu Pro Lys  Tyr Ser Leu
    1190                 1195                 1200

Phe Glu  Leu Glu Asn Gly Arg  Lys Arg Met Leu Ala  Ser Ala Gly
    1205                 1210                 1215

Glu Leu  Gln Lys Gly Asn Glu  Leu Ala Leu Pro Ser  Lys Tyr Val
    1220                 1225                 1230

Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365

Gly Ser  Pro Lys Lys Lys Arg  Lys Val Ser Ser Asp  Tyr Lys Asp
    1370                 1375                 1380

His Asp  Gly Asp Tyr Lys Asp  His Asp Ile Asp Tyr  Lys Asp Asp
    1385                 1390                 1395

Asp Asp  Lys Ala Ala Gly Gly  Gly Gly Ser Leu Pro  Thr Cys Ser
    1400                 1405                 1410

Cys Leu  Asp Arg Val Ile Gln  Lys Asp Lys Gly Pro  Tyr Tyr Thr
    1415                 1420                 1425

His Leu  Gly Ala Gly Pro Ser  Val Ala Ala Val Arg  Glu Ile Met
    1430                 1435                 1440

Glu Asn  Arg Tyr Gly Gln Lys  Gly Asn Ala Ile Arg  Ile Glu Ile
    1445                 1450                 1455

Val Val  Tyr Thr Gly Lys Glu  Gly Lys Ser Ser His  Gly Cys Pro
    1460                 1465                 1470

Ile Ala  Lys Trp Val Leu Arg  Arg Ser Ser Asp Glu  Glu Lys Val
    1475                 1480                 1485

Leu Cys  Leu Val Arg Gln Arg  Thr Gly His His Cys  Pro Thr Ala
    1490                 1495                 1500

Val Met  Val Val Leu Ile Met  Val Trp Asp Gly Ile  Pro Leu Pro
```

```
    1505                1510                1515

Met Ala  Asp Arg Leu Tyr Thr  Glu Leu Thr Glu Asn  Leu Lys Ser
    1520                1525                1530

Tyr Asn  Gly His Pro Thr Asp  Arg Arg Cys Thr Leu  Asn Glu Asn
    1535                1540                1545

Arg Thr  Cys Thr Cys Gln Gly  Ile Asp Pro Glu Thr  Cys Gly Ala
    1550                1555                1560

Ser Phe  Ser Phe Gly Cys Ser  Trp Ser Met Tyr Phe  Asn Gly Cys
    1565                1570                1575

Lys Phe  Gly Arg Ser Pro Ser  Pro Arg Arg Phe Arg  Ile Asp Pro
    1580                1585                1590

Ser Ser  Pro Leu His Glu Lys  Asn Leu Glu Asp Asn  Leu Gln Ser
    1595                1600                1605

Leu Ala  Thr Arg Leu Ala Pro  Ile Tyr Lys Gln Tyr  Ala Pro Val
    1610                1615                1620

Ala Tyr  Gln Asn Gln Val Glu  Tyr Glu Asn Val Ala  Arg Glu Cys
    1625                1630                1635

Arg Leu  Gly Ser Lys Glu Gly  Arg Pro Phe Ser Gly  Val Thr Ala
    1640                1645                1650

Cys Leu  Asp Phe Cys Ala His  Pro His Arg Asp Ile  His Asn Met
    1655                1660                1665

Asn Asn  Gly Ser Thr Val Val  Cys Thr Leu Thr Arg  Glu Asp Asn
    1670                1675                1680

Arg Ser  Leu Gly Val Ile Pro  Gln Asp Glu Gln Leu  His Val Leu
    1685                1690                1695

Pro Leu  Tyr Lys Leu Ser Asp  Thr Asp Glu Phe Gly  Ser Lys Glu
    1700                1705                1710

Gly Met  Glu Ala Lys Ile Lys  Ser Gly Ala Ile Glu  Val Leu Ala
    1715                1720                1725

Pro Arg  Arg Lys Lys Arg Thr  Cys Phe Thr Gln Pro  Val Pro Arg
    1730                1735                1740

Ser Gly  Lys Lys Arg Ala Ala  Met Met Thr Glu Val  Leu Ala His
    1745                1750                1755

Lys Ile  Arg Ala Val Glu Lys  Lys Pro Ile Pro Arg  Ile Lys Arg
    1760                1765                1770

Lys Asn  Asn Ser Thr Thr Thr  Asn Asn Ser Lys Pro  Ser Ser Leu
    1775                1780                1785

Pro Thr  Leu Gly Ser Asn Thr  Glu Thr Val Gln Pro  Glu Val Lys
    1790                1795                1800

Ser Glu  Thr Glu Pro His Phe  Ile Leu Lys Ser Ser  Asp Asn Thr
    1805                1810                1815

Lys Thr  Tyr Ser Leu Met Pro  Ser Ala Pro His Pro  Val Lys Glu
    1820                1825                1830

Ala Ser  Pro Gly Phe Ser Trp  Ser Pro Lys Thr Ala  Ser Ala Thr
    1835                1840                1845

Pro Ala  Pro Leu Lys Asn Asp  Ala Thr Ala Ser Cys  Gly Phe Ser
    1850                1855                1860

Glu Arg  Ser Ser Thr Pro His  Cys Thr Met Pro Ser  Gly Arg Leu
    1865                1870                1875

Ser Gly  Ala Asn Ala Ala Ala  Ala Asp Gly Pro Gly  Ile Ser Gln
    1880                1885                1890

Leu Gly  Glu Val Ala Pro Leu  Pro Thr Leu Ser Ala  Pro Val Met
    1895                1900                1905
```

```
Glu Pro  Leu Ile Asn Ser Glu  Pro Ser Thr Gly Val  Thr Glu Pro
    1910                 1915                 1920

Leu Thr  Pro His Gln Pro Asn  His Gln Pro Ser Phe  Leu Thr Ser
    1925                 1930                 1935

Pro Gln  Asp Leu Ala Ser Ser  Pro Met Glu Glu Asp  Glu Gln His
    1940                 1945                 1950

Ser Glu  Ala Asp Glu Pro Pro  Ser Asp Glu Pro Leu  Ser Asp Asp
    1955                 1960                 1965

Pro Leu  Ser Pro Ala Glu Glu  Lys Leu Pro His Ile  Asp Glu Tyr
    1970                 1975                 1980

Trp Ser  Asp Ser Glu His Ile  Phe Leu Asp Ala Asn  Ile Gly Gly
    1985                 1990                 1995

Val Ala  Ile Ala Pro Ala His  Gly Ser Val Leu Ile  Glu Cys Ala
    2000                 2005                 2010

Arg Arg  Glu Leu His Ala Thr  Thr Pro Val Glu His  Pro Asn Arg
    2015                 2020                 2025

Asn His  Pro Thr Arg Leu Ser  Leu Val Phe Tyr Gln  His Lys Asn
    2030                 2035                 2040

Leu Asn  Lys Pro Gln His Gly  Phe Glu Leu Asn Lys  Ile Lys Phe
    2045                 2050                 2055

Glu Ala  Lys Glu Ala Lys Asn  Lys Lys Met Lys Ala  Ser Glu Gln
    2060                 2065                 2070

Lys Asp  Gln Ala Ala Asn Glu  Gly Pro Glu Gln Ser  Ser Glu Val
    2075                 2080                 2085

Asn Glu  Leu Asn Gln Ile Pro  Ser His Lys Ala Leu  Thr Leu Thr
    2090                 2095                 2100

His Asp  Asn Val Val Thr Val  Ser Pro Tyr Ala Leu  Thr His Val
    2105                 2110                 2115

Ala Gly  Pro Tyr Asn His Trp  Val
    2120                 2125
```